(12) United States Patent
Ono et al.

(10) Patent No.: US 7,935,802 B2
(45) Date of Patent: May 3, 2011

(54) LIGNAN GLYCOSIDASE AND UTILIZATION OF THE SAME

(75) Inventors: Eiichiro Ono, Osaka (JP); Yoshikazu Tanaka, Osaka (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 460 days.

(21) Appl. No.: 11/666,157

(22) PCT Filed: Nov. 2, 2005

(86) PCT No.: PCT/JP2005/020495
§ 371 (c)(1),
(2), (4) Date: Mar. 18, 2008

(87) PCT Pub. No.: WO2006/049315
PCT Pub. Date: May 11, 2006

(65) Prior Publication Data
US 2008/0293099 A1 Nov. 27, 2008

(30) Foreign Application Priority Data

Nov. 2, 2004 (JP) ................................. 2004-319624

(51) Int. Cl.
*C07H 21/04* (2006.01)
*C12N 9/42* (2006.01)
*C12P 21/02* (2006.01)
*C07D 307/80* (2006.01)

(52) U.S. Cl. ........ 536/23.2; 435/69.1; 435/209; 549/435

(58) Field of Classification Search .................. 536/23.2; 435/69.1, 209; 549/435
See application file for complete search history.

(56) References Cited

FOREIGN PATENT DOCUMENTS

| JP | 10-7676 | 1/1998 |
|---|---|---|
| JP | 10-113184 | 5/1998 |
| JP | 2001-139579 | 5/2001 |
| JP | 2001-507931 | 6/2001 |
| JP | 2004-344113 | 12/2004 |
| WO | WO 99/55846 | 11/1999 |
| WO | 2004/018682 | 3/2004 |

OTHER PUBLICATIONS

Suzuki et al., "Stereochemical diversity in lignan biosynthesis of *Arctium lappa* L.," Biosci Biotechnol Biochem 66(6):1262-1269, 2002.*
Alignment of Seq Id No. 1 with NTGT1a gene of Taguchi et al. ("Molecular cloning and heterologous expression of novel glucosyltransferases from tobacco cultured cells that have broad substrate specificity and are induced by salicylic acid and auxin," Eur J Biochem 268(14):4086-4094, 2001, alignment performed Jan. 22, 2010.*
Claim set for corresponding EP Application No. 05803357.2, filed on Nov. 2, 2005.*
Norman G. Lewis, et al., "Stereo selectivity in Polyphenol Biosynthesis", Basic Life Science, 1992, vol. 59, pp. 73 to 95.

(Continued)

*Primary Examiner* — Karen Cochrane Carlson
*Assistant Examiner* — Rosanne Kosson
(74) *Attorney, Agent, or Firm* — Drinker Biddle & Reath LLP

(57) ABSTRACT

The present invention provides an enzyme having the lignan glycosidation activity by identifying the enzyme that is involved in the production of lignan glycosides, identifying the amino acid sequence of the enzyme polypeptide and the base sequence for a polynucleotide encoding the polypeptide, and based on the information of these sequences, preparing the transformants capable of producing the lignan glycosides.

8 Claims, 53 Drawing Sheets

OTHER PUBLICATIONS

Peter I. MacKenzie et al., "The UDP Glycosyltransferase Gene Superfamily: Recommend Nomenclature Update Based on Evolutionary Divergence", Pharmacogenetics, 1997, vol. 7, No. 4, pp. 255-269.

Yi Li Sandie Baldauf et al., "Phylogenetic Analysis of the UDP-glycosyltransferase Multigene Family of *Arabidopis thaliana*", Journal of Biological Chemistry, 2001, vol. 276, No. 6, Feb. 9, pp. 4338 to 4343.

Yoshiyuki Miyayara et al., "*Absidia corymbifera o* Riyo Shita Goma Dasshikasuchu ni Fukumareru Sasaminol eno Henkan", Journal of the Japanese Society for Food Science and Technology, 2001, vol. 48, No. 5, pp. 370 to 373. [English Abstract], Abstract only.

International Search Report mailed Dec. 13, 2005 of International PCT Application No. PCT/JP2005/020495.

Chiba et al., "Studies on the Chinese Crude Drug 'Forsythiae Fructus.' (III) on the Contituents of Fruits of *Forsythia veridissia* and *F. suspensa*," Shoyakugaku Zaashi, vol. 32, No. 1, Mar. 1978, pp. 194-197, Abstract only considered; article in Japanese.

Shinnosuke Sato et al., "Goma (*Sesamum indicum L.*) no Seiiku ni Tomonau Sesame Lingan no Dotai", Nissaku Tokai Shibuho, 2000, No. 129, pp. 29 to 30, particularly, p. 30, lines 8 to 9. [English Translation].

Taguchi et al., "Exogenously added naphthols induce three glucosyltransferases, and are accumulated as glucosides in tobacco cells," Plant Science, vol. 164, 2003, pp. 231-240.

Taguchi et al., "Molecular cloning and heterologous expression of novel glucosyltransferases from tobacco cultured cells that have broad substrate specificity and are induced by salicylic acid and auxin," Eur. J. Biochem, vol. 268, 2001, pp. 4086-4094, Blackwell Science, Berlin, Germany.

European Search Report issued Sep. 15, 2008, in European Application No. EP 05803357.

Xia et al., "Secoisolariciresinol Dehydrogenase Purification, Cloning, and Functional Expression" Journal of Biological Chemistry, vol. 276, No. 16, 2001, pp. 12614-12623.

Dinkova-Kostova et al., "(+)-Pinoresinol/(+)-Lariciresinol Reductase from *Forsythia intermedia*" Journal of Biological Chemistry, vol. 271, No. 46, 1996, pp. 29473-29482.

Fujita et al., "Recombinant Pinoresinol-Lariciresinol Reductases from Western Red Cedar (*Thuja plicata*) Catalyze Opposite Enantiospecific Conversions", Journal of Biological Chemistry, vol. 274, No. 2, 1999, pp. 618-627.

Cho et al., (+)-Larreatricin Hydroxylase, an Enantio-Specific Polyphenol Oxidase from the Creosote Bush (*Larrea tridentate*), Proceedings of National Academy of Sciences, vol. 100, No. 19, 2003, pp. 10641-10646.

Katsuzaki et al., "Structure of Novel Antioxidative Lignan Glucosides Isolated from Sesame Seed", Biosci. Biotech. Biochem. vol. 56, No. 12, 1992, pp. 2087-2088.

Toshihiko Osawa, "Plant Antioxidants as Anticarcinogens" Anticarcinogenesis and Radiation Protection 2, Plenum Press, New York, 1991, pp. 327-336.

Lewis et al., "Lignans" Biosynthesis and Function Comprehensive Nature Products Chemistry, Elsevier, 1999, pp. 639-712.

* cited by examiner

A. Growth stages of sesame in the order of youngest to oldest
B. Gene expression analysis by RT-PCR M: size marker
Sup: crude enzyme solution prior to column chromatography

Fig. 7E

Putative Physiological response

| | |
|---|---|
| A | Unknown |
| B | Seed/endosperm/embryo-related |
| C | Etiolation-related |
| D | Auxin-related |
| E | GA/amylase-related |
| F | ABA-related |
| G | Ethylen-related |
| H | Light-regulated |
| I | Pathogenesis-related |
| J | Circadian clock-regulated |
| K | Secondary metabolism-related |
| L | Pollen development |

Putative structure of target *trans*-factor

| | |
|---|---|
| A | Myc (bHLH class) |
| B | Myb |
| C | Zinc Finger (Dof class) |
| D | Homeobox |
| E | MADS |
| F | ARF |
| G | Leucine Zipper (TGA class) |
| H | bZIP (DPBF class) |
| I | WRKY |
| J | AP2-domain (RAV class) |

Fig. 8F

-510 DOF-core Zm [A] (C)
-513 GT1consensus [H]
-514 Pollen1 LeLAT52 [L]
-528 RAV1-A At [A] (J)
-535 CAAT-box [B]
-537 I-box core [HH]
-537 INR N.t psaD-B [H]
-584 GATA-box [H]
-598 GT1consensus [H]
-599 Pollen1 LeLAT52 [L]
-603 DOF-core Zm [A] (C)
-616 Pyrimidine-box HvEBP1 [E]
-624 ACGT Aterd1 [C]
-627 GATA-box [H]
-642 DOF-core Zm [A] (C)
-668 Circadian LeLHC [J]
-671 RAV1-A At [A] (J)
-675 SEF3motif Gm [B]
-679 AAC core osglub1 [B]
-680 RAV1-A At [A] (J)
-707 DOF-core Zm [A] (C)
-753 CAAT-box [AB]
-754 CAAT-box1 [AB]

LIGNAN GLYCOSIDASE AND UTILIZATION OF THE SAME

TECHNICAL FIELD

The present invention relates to enzymes having the activity to transfer sugars to lignans and utilization of the enzymes.

BACKGROUND ART

Sesame (*Sesamum indicum*) is an annual plant in the family Pedaliaceae belonging to the genus *Sesamum*. Sesame is said to be indigenous to Central Africa. Supposedly sesame is the oldest domesticated oil seed crop having about a 6000 year history and has been cultivated throughout the world. Sesame is a valuable food from ancient times and known as representing healthy foods. In particular, sesame seeds, oil pressed from sesame seeds and extracts from sesame seeds are utilized (see, e.g., Goma: SONO-KAGAKU-TO-KINOSEI (Sesame: Science and Function), edited by Mitsuo Namiki, Maruzen Planet Publishing Co. (1998)). The components contained in sesame seeds are about 50% of lipids and about 20% of proteins. The major components of lipids contained in sesame are essentially triglycerides mainly composed of oleic acid and linoleic acid. Furthermore, sesame contains vitamins B1, B2, E, etc. In addition to the components described above, secondary metabolites (e.g., sesamin, sesamolin, etc.) of plants collectively referred to as lignans are contained in sesame, and a sesame lignan is a distinctive component in sesame seeds (see, e.g., Bedigian, D., et al., Biochemical Systematics and Ecology, 13, 133-139 (1985)).

Lignans are compounds in which two phenylpropanoid molecules having the $C_6C_3$ skeleton are dimerized mostly through the 8-8' position (a 8,8'-linkage). Lignans are considered to contribute to biological defense mechanisms in plants.

Representative lignans include sesamin, sesaminol, sesamolin and sesamolinol contained in sesame (*Sesamum indicum*); (+)-pinoresinol, (−)-arctigenin and (−)-matairesinol contained in *Forsythia intermedia*; (−)-pinoresinol and (−)-lariciresinol contained in *Daphne tangutica*; (+)-secoisolariciresinol contained in *Linum usitatissimum*; etc. Molecular structures of these lignans are diverse.

Sesamin, which is one of sesame lignans, displays an abundance of biological activities and are effective for improving cholesterol metabolism, liver function and immune function (see, e.g., Goma: SONO-KAGAKU-TO-KINOSEI (Sesame: Science and Function), edited by Mitsuo Namiki, Maruzen Planet Publishing Co. (1998)). Methods for the separation and purification of sesamin from sesame seeds or sesame lees have already been launched (see, e.g., Japanese Patent Laid-open Publication (Kokai) No. 2001-139579 (laid open to public inspection on May 22, 2001) and Japanese Patent Laid-open Publication (Kokai) No. 10-7676 (laid open to public inspection on Jan. 13, 1998)), and sesamin-based liver function improvers/potentiators having an alcoholysis-promoting activity are commercially available (trade name: Sesamin, from sales agency Suntory, Ltd.). It is reported that lignans other than sesamin (see, e.g., sesaminol, sesamolin, etc.) also have biological activities (see, e.g., J. Bioscience, Biotechnology and Biochemistry, 76: 805-813 (2002)).

As to biosynthesis of lignans, reference is made to, e.g., Lignans: Biosynthesis and Function, Comprehensive Natural Products Chemistry, 1: 640-713 (1999). It is shown in Lignans: Biosynthesis and Function, Comprehensive Natural Products Chemistry, 1: 640-713 (1999) that pinoresinol synthesized by polymerization of coniferyl alcohol is the first lignan in the biosynthesis and a variety of lignans are synthesized from pinoresinol via biosynthetic pathways specific to individual plant species. General biosynthesis of lignans is illustratively shown in the schematic diagram below.

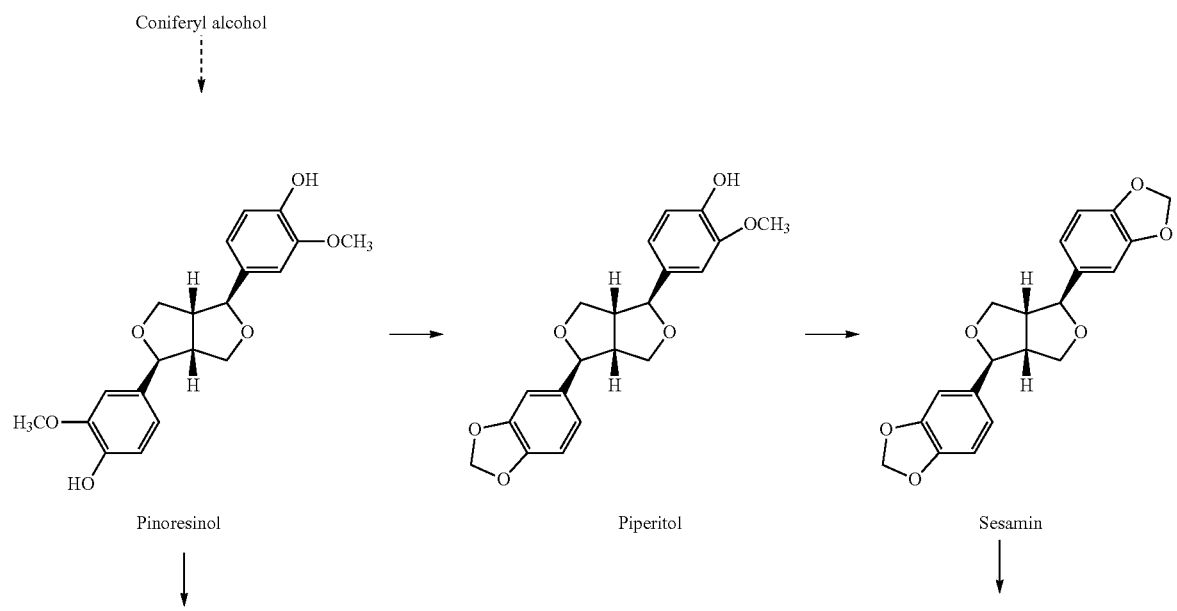

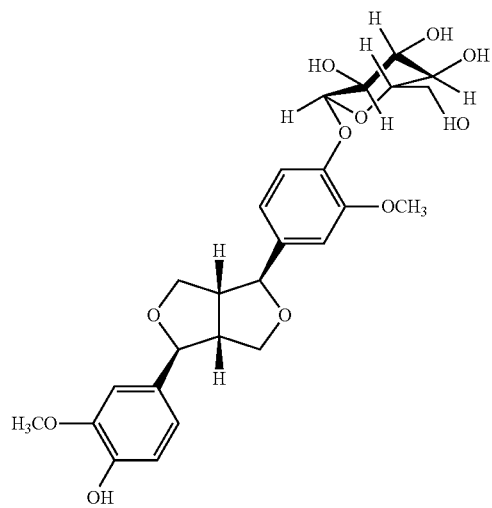

Pinoresinol glycoside

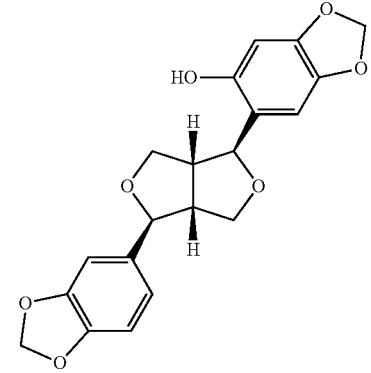

Sesaminol

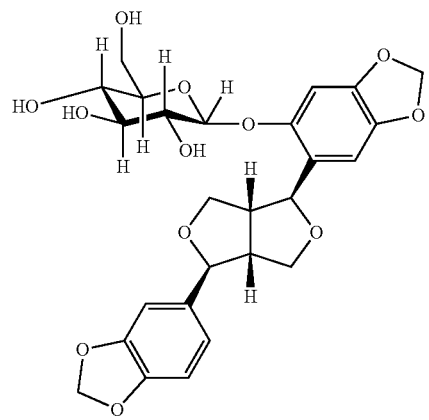

Sesaminol glycoside

Piperitol synthase acts on (+)-pinoresinol to synthesize piperitol. Next, sesamin synthase acts on this piperitol to synthesize sesamin.

As the enzymes involved in the biosynthesis of lignans, dirigent proteins which take part in pinoresinol synthesis are reported in *Forsythia intermedia*, etc. (see, e.g., Plant Physiol., 123: 453 (2000) and Japanese National Phase PCT Laid-open Publication No. 2001-507931 (laid open to public inspection on Jun. 19, 2001)). As genes for enzymes involved in the lignan biosynthesis and their utilization, there are further reported the gene for pinoresinol/lariciresinol reductase in *Forsythia intermedia* (see, e.g., J. Biol. Chem., 271:29473 (1996) and Japanese National Phase PCT Laid-open Publication No. 2001-507931 (laid open to public inspection on Jun. 19, 2001)), the gene for pinoresinol/lariciresinol reductase in *Thuja plicata* (see, e.g., J. Biol. Chem., 274: 618 (1999) and recombinant secoisolariciresinol dehydrogenase and the method of its use (see, e.g., J. Biol. Chem., 276 (16): 12614-23 (2001) and Japanese National Phase PCT Laid-open Publication No. 2002-512790 (laid open to public inspection on May 18, 2002)). Besides, the gene for larreatricin hydroxylase has been cloned from *Larrea tridentata* (see, e.g., Proc. Nat. Acad. Sci. USA, 100: 10641 (2003)).

Regarding the biosynthesis of sesame lignans, it is also reported that exhaustive analysis of about 3000 clones of the gene expressed in sesame seeds gave dirigent proteins, seed storage proteins and gene fragments associated with lipid synthesis (see, e.g., Plant Mol. Biol., 52: 1107 (2003)). Moreover, the gene involved in fatty acid synthesis (see, e.g., Biosci. Biotechnol. Biochem., 66(10): 2146-53 (2002), Plant Physiol., 128 (4): 1200-11 (2002) and Plant Cell Physiol., 37(2): 201-5 (1996)), and the gene for seed storage protein, etc. are cloned from sesame.

In recent years, attention has been drawn not only to lignans but to lignan glycosides. It is known that some of the lignan molecules described above are present as glycosides in plants. For instance, sesaminol glycosides (sesaminol 2'-O-β-D-glucopyranoside; sesaminol 2'-O-β-D-glucopyranosyl (1-2)-O-β-D-glucopyranoside; and sesaminol 2'-O-β-D-glucopyranosyl (1-2)-O-(-β-D-glucopyranosyl(1-6))-β-D-glucopyranoside)), and pinoresinol glycosides (pinoresinol 4'-O-β-D-glucopyranosyl (1-6)-β-D-glucopyranoside; pinoresinol 4'-O-β-D-glucopyranosyl (1-2)-β-D-glucopyranoside; pinoresinol 4'-O-β-D-glucopyranosyl (1-6)-O-(β-D-glucopyranosyl (1-6)) β-D-glucopyranoside; and pinoresinol di-O-β-D-glucopyranoside)), etc. are present in sesame seeds; (+)-pinoresinol 4'-O-β-D-glucoside and (−)-matairesinol-4-O-glucoside, etc. are present in *Forsythia intermedia*; and secolariciresinol diglucoside and pinoresinol diglucoside, etc. are present in *Linum usitatissimum* (see, e.g., Goma: SONO-KAGAKU-TO-KINOSEI (Sesame: Science and Function), edited by Mitsuo Namiki, Maruzen Planet Publishing Co. (1998), Journal of Natural Medicines, 32, 194 (1978), Tetrahedron, 14: 649 (2003) and Phytochemistry, 58: 587 (2001)).

Glycosides are produced through the glycosidation (glycosyl transfer) reaction of various compounds such as flavonoids being catalyzed by enzymes called glycosidases or glycosyltransferases. To date, the amino acid sequences of some glycosyltransferases and their functions have been elucidated. Genes for an enzyme (UDP-glucose: flavonoid 3-glucosyltransferase) which catalyzes a reaction to transfer a sugar onto the hydroxyl group at the position 3 of flavonoids or anthocyanidins have been obtained from maize, gentian, grapevine, etc. (see, e.g., J. Biol. Chem., 276:4338 (2001)). Also, genes for an enzyme (UDP-glucose: anthocyanidin 5-glucosyltransferase) which catalyzes a reaction to transfer a sugar onto the hydroxyl at the position 5 of anthocyanidins have been obtained from perilla, verbena, etc. (see, e.g., J. Biol. Chem. 274:7405 (1999)).

Pinoresinol glycosides and sesaminol glycosides contained in sesame (see, e.g., Goma: SONO-KAGAKU-TO-KINOSEI (Sesame: Science and Function), edited by Mitsuo Namiki, Maruzen Planet Publishing Co. (1998) and Katsuzaki, H. et al., Biosci. Biotech. Biochem., 56, 2087-2088 (1992)) show potent antioxidative properties in the water-soluble region, and are expected to yield different applications than lipophilic antioxidants (e.g., tocopherol). Also, the following mechanism of action is proposed for lignan glycosides. In lignan glycosides, the phenolic hydroxyl group, which is a functional group exhibiting antioxidative properties, are protected by sugars possessed by themselves but taken up into the body and then hydrolyzed by the action of β-glucosidase from enterobacteria to produce lipophilic lignans as the aglycone portion. This aglycone is absorbed into the intestines and carried to various organs via blood to prevent oxidative damages in biomembranes of the organs, etc. Based on this mechanism of action, lignan glycosides are expected to involve applications as preventive diets for arteriosclerosis (see, e.g., T. Osawa: Anticarcinogenesis and Radiation Protection 2: p. 327, Plenum Press, New York (1991)).

The biosynthetic pathway of secondary metabolites in plants is modified to produce useful substances and/or breed useful plants. Such a technology is called metabolic engineering. Use of such a technology enables to produce optional compounds in a large scale and/or prevent the production of unwanted substances. Accordingly, it is industrially useful to synthesize lignans and their glycosides by metabolic engineering using the genes involved in the biosynthesis of lignans and their glycosides, in view of the utility of these substances as described above. However, findings on the genes involved in the biosynthesis of lignans, especially sesame lignans are so limited as described above, and any glycosidase that catalyzes the production of lignan glycosides is not found. It has thus been desired to acquire additional genes.

DISCLOSURE OF THE INVENTION

It is known that sesaminol glycosides are produced not only in seeds but in germinated seeds (see, e.g., Goma: SONO-KAGAKU-TO-KINOSEI (Sesame: Science and Function), edited by Mitsuo Namiki, Maruzen Planet Publishing Co. (1998)).

In sesame seeds, lignan glycosides (e.g., sesaminol diglucoside, etc.) are formed accompanied by a rapid decrease of sesamin and sesamolin during germination (see, e.g., J. Bioscience, Biotechnology and Biochemistry, 69: 68 (1995)). This suggests that lignan glycosidases (i.e., glycosyltransferases to lignans) are activated during germination of sesame seeds and as a result, lignans are glycosidated. β-Glucosidase in sesame seeds has a high transglycosylation activity and the transglycosylation activity possessed by β-glucosidase increases at the early stage of germination; based on the findings, it is suggested that an increase in the transglycosylation activity possessed by β-glucosidase is closely related to an increase of glycosides (see, e.g., J. Bioscience, Biotechnology and Biochemistry, 69: 68 (1995)). However, there is no finding to show that the transglycosylation activity possessed by β-glucosidase would be involved in lignan glycosidation.

It is known that proteins having a particular function to catalyze the transglycosylation reaction resemble in amino acid sequences even though plant species are different (see, e.g., J. Biol. Chem. 276: 4338 (2001)). Then, it is not difficult to obtain the ortholog of glycosyltransferase having the determined amino acid sequence and its substrate from other plant species according to the state of the art. In fact, the gene for UDP-glucose: anthocyanin 5-glucosyltransferase of petunia was cloned using the sequence information from the gene for UDP-glucose: anthocyanin 5-glucosyltransferase of perilla (see, e.g., Plant Mol. Biol. 48: 401-11 (2002)).

As described above, however, there is no report so far that enzymes having the activity to transfer sugars to lignans and genes encoding the enzymes are isolated. Since any enzyme having the lignan glycosidation activity is not isolated, it is technically difficult to acquire such a novel glycosidase, and a lot of trial and error is needed to acquire such a novel glycosidase since any practical procedure to acquire the enzymes is not available.

Even in plants such as *Arabidopsis* or rice plant, which were determined for the whole genome sequence, accumulation of lignan glycosides in these seeds are not reported. In other words, any enzyme having the lignan glycosidation activity is not present so far.

The present invention has been made in view of the problems mentioned above and an object is to provide enzymes having the lignan glycosidation activity, in particular, enzymes which catalyze a reaction to transfer a sugar to the hydroxyl group of lignans, preferably enzymes which catalyze reactions to produce sesaminol glycosides from sesaminol and pinoresinol glycosides from pinoresinol. Phrased differently, an object of the present invention is to provide lignan glycosides by metabolic engineering using enzymes having the activity to transfer a sugar to lignans.

Another object of the present invention is to provide a method of producing plants (especially sesame) by metabolic engineering wherein the content ratio of lignans to lignan glycosides are increased or decreased, to efficiently produce the lignans or lignan glycosides.

The polypeptide in accordance with the present invention is characterized by having the lignan glycosidation activity.

The polypeptide in accordance with the present invention is a polypeptide characterized by having the lignan glycosidation activity and consisting of:

(a) the amino acid sequence represented by any one of SEQ ID NO: 2, 4, 82 or 91; or (b) the amino acid sequence wherein one or more amino acids are deleted, inserted, substituted or added, in the amino acid sequence represented by any one of SEQ ID NO: 2, 4, 82 or 91.

The polynucleotide in accordance with the present invention is characterized by encoding the polypeptide described above.

The polynucleotide in accordance with the present invention is characterized by encoding the polypeptide having the lignan glycosidation activity, which is either:
(a) a polynucleotide consisting of the base sequence represented by any one of SEQ ID NO: 1, 3, 81 or 90; or
(b) a polynucleotide consisting of the base sequence wherein one or more bases are deleted, inserted, substituted or added, in the base sequence represented by any one of SEQ ID NO: 1, 3, 81 or 90.

The polynucleotide in accordance with the present invention is a polynucleotide characterized by encoding a polypeptide having the lignan glycosidation activity, which is either:
(a) a polynucleotide consisting of the base sequence represented by any one of SEQ ID NO: 1, 3, 81 or 90; or
(b) a polynucleotide hybridizable to the polynucleotide consisting of the complementary base sequence to the base sequence represented by any one of SEQ ID NO: 1, 3, 81 or 90, under stringent conditions.

The polynucleotide in accordance with the present invention characterized by encoding a polypeptide having the lignan glycosidation activity, which is either:
(a) a polynucleotide consisting of the base sequence represented by any one of SEQ ID NO: 1, 3, 81 or 90; or
(b) a polynucleotide consisting of a base sequence which has at least 80% identity to the base sequence represented by any one of SEQ ID NO: 1, 3, 81 or 90.

The oligonucleotide in accordance with the present invention is characterized by consisting of a fragment of the polynucleotide described above, or a complementary sequence thereto.

The oligonucleotide in accordance with the present invention preferably represses the expression of the polypeptide described above.

The vector in accordance with the present invention comprises the polynucleotide described above.

The method of producing the polypeptide in accordance with the present invention is characterized by using the vector described above.

The transformant in accordance with the present invention is characterized in that the polynucleotide described above is introduced.

The transformant in accordance with the present invention preferably has an altered content ratio of lignans to lignan glycosides.

The transformant in accordance with the present invention is preferably an organism or its progeny, or a tissue derived therefrom.

In the transformant in accordance with the present invention, the organism described above is preferably a plant.

In the transformant in accordance with the present invention, the plant described above is preferably sesame, *Forsythia intermedia* or *Linum usitatissimum*.

The method of producing the polypeptide in accordance with the present invention is characterized by using the transformant described above.

In the method of producing the polypeptide in accordance with the present invention, it is preferred to use the transformant described above.

In the method of producing the polypeptide in accordance with the present invention, an aglycone of the lignan glycoside described above is preferably piperitol, sesaminol or pinoresinol.

The cell in accordance with the present invention comprises the vector described above.

The cell in accordance with the present invention is preferably a cell of sesame, *Forsythia intermedia* or *Linum usitatissimum*.

The method of producing the polypeptide in accordance with the present invention is characterized by using the cell described above.

The method of producing lignan glycosides in accordance with the present invention is characterized by using the cell described above.

In the method of producing lignan glycosides in accordance with the present invention, an aglycone of the lignan glycoside described above is preferably piperitol, sesaminol or pinoresinol.

In the method of producing lignan glycosides in accordance with the present invention, it is preferred to use the polypeptide described above.

In the method of producing lignan glycosides in accordance with the present invention, an aglycone of the lignan glycoside described above is preferably piperitol, sesaminol or pinoresinol.

The foodstuff or industrial product in accordance with the present invention comprises the lignan glycoside produced by the production method described above.

In the foodstuff or industrial product in accordance with the present invention, an aglycone of the lignan glycoside described above is preferably piperitol, sesaminol or pinoresinol.

The method in accordance with the present invention of increasing the content of lignan glycoside in an organism comprises the step of introducing the polynucleotide described above into a lignan-producing organism.

In the method in accordance with the present invention of increasing the content of lignan glycosides in an organism, the lignan-producing organism described above is preferably sesame, *Forsythia intermedia* or *Linum usitatissimum*.

In the method in accordance with the present invention of increasing the content of lignan glycosides in an organism, the lignan described above is preferably piperitol, sesaminol or pinoresinol.

The method in accordance with the present invention of decreasing the content of lignan glycosides in an organism comprises the step of introducing the oligonucleotide described above into a lignan-producing organism.

In the method in accordance with the present invention of decreasing the content of lignan glycosides in an organism, the lignan-producing organism described above is preferably sesame, *Forsythia intermedia* or *Linum usitatissimum*.

In the method in accordance with the present invention of decreasing the content of lignan glycosides in an organism, the lignan described above is preferably piperitol, sesaminol or pinoresinol.

The polypeptide (lignan glycosidase) in accordance with the present invention is utilized to exhibit the effect of artificially regulating the amounts of lignans and lignan glycosides in organisms (especially plants). Furthermore, lignans can be glycosidated using these recombinant enzymes to modify physical properties (solubility, absorption efficiency in animal, etc.) in vitro and in vivo. Further by using SiGT8, the effect of artificially producing lignan glycosides not existing in nature can be exhibited. Based on these effects, the present invention can serve to develop substances having novel physiological functions.

The lignan glycosidase in accordance with the present invention can be expressed in a desired organism using genetic recombination technology thereby to exhibit the effect of artificially producing the sesaminol glycosides from sesaminol and/or the pinoresinol glycosides from pinoresinol. Also, the lignan glycosidase in accordance with the present invention can be expressed in a desired organism using genetic recombination technology thereby to exhibit the effect of preparing plants and/or microorganisms with artificially controlled amounts of lignans and lignan glycosides.

Thus, the effect that biokinetic changes of these lignans can be changed (the ratio of lipophilic lignans to water-soluble lignan glycosides can be readily determined) is exhibited. In other words, the effect that balance can be adjusted between lignan glycosides with good systemic absorption and lignans with low systemic absorption can be exhibited. When lignan glycosides (especially sesaminol glycosides) are administered to the living body, they are metabolized into highly oxidative lignans called sesaminol catechols. The sesaminol glycosides are also converted into the sesaminol catechols by *aspergillus*. Further by glycosidation of lignans, the solubility of lignans in water can be improved so that the sesaminol glycosides can be utilized to prepare lignan-containing beverages. Where lignans are provided as beverages (liquid), it is very important to make lignans water-soluble. The lignan glycosidase in accordance with the present invention exerts the effect that precursors of lignans having an extremely strong oxidative property.

Moreover, the expression of the lignan glycosidase in accordance with the present invention is repressed in plants producing sesaminol glycosides or pinoresinol glycosides to release the aglycones (i.e., the non-sugar portion of glycosides) and thus, the effect of increasing the amounts of lignans (especially sesaminol and/or pinoresinol) can be exhibited. Further by using the lignan glycosidase in accordance with the present invention, the effect of artificially producing the novel lignan glycosides or piperitol glycosides from piperitol is exhibited.

BRIEF DESCRIPTION OF THE DRAWINGS

FIG. 7E is a graph representing regulatory elements shown in FIGS. 7A-7D.

FIG. 8F continues from FIG. 8E and is a graph showing the results of expression regulatory-element analysis of the SiGT10 gene.

BEST MODE FOR CARRYING OUT THE INVENTION

Figure 1:
FIG. 1A shows photographs of sesame hulls (upper column a in the figure) and seeds (lower column a in the figure) (growth stages 1 to 4 in the order of youngest to oldest) and germinated seeds (b in the figure).
FIG. 1B shows the results of gene expression analysis by RT-PCR using total RNA extracted from the sesame leaf, flower, stem, hull or seed shown in FIG. 1A.
Figure 1:
Figure 1:
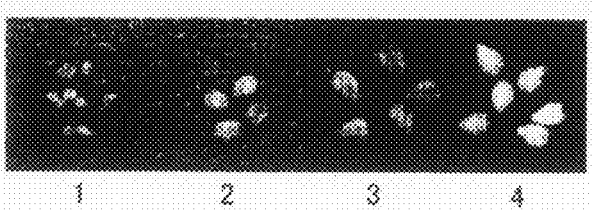
Figure 1:
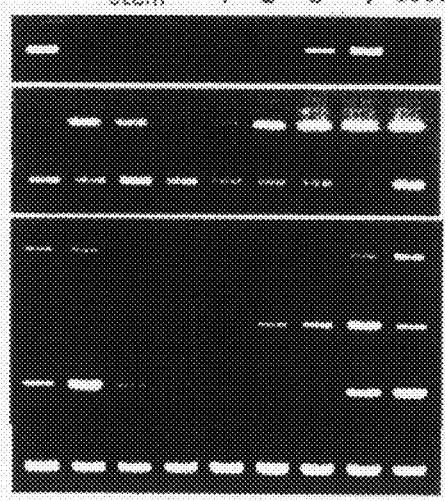

Using a composite probe prepared by combining plural regions conserved among plant-derived glycosyltransferases, the present inventors exhaustively acquired the sesame glycosyltransferase gene family (hereinafter referred to as the SiGT gene) from the sesame seed cDNA library. From the gene family acquired, sesame glycosyltransferases (hereinafter referred to as SiGT) were allowed to express in *Escherichia coli*. The recombinant protein acquired was reacted with sesaminol or pinoresinol, and an enzyme that catalyzes the formation of sesaminol glycosides or pinoresinol glycosides was selected by the HPLC analysis, LC-MS analysis and TOF-MS/MS analysis. As a result, it became clear that SiGT8 catalyzes the reaction to produce sesaminol glycosides from sesaminol and the reaction to produce pinoresinol glycosides from pinoresinol. It also became clear that SiGT10 catalyzes the reaction to produce sesaminol glycosides from sesaminol. It was further found that SiGT8 has a piperitol glycosidation activity to produce a novel lignan glycoside, i.e., the piperitol glycoside, which has not been reported to date.

Hereinafter, the polypeptide in accordance with the present invention, which has the lignan glycosidation activity, and the polynucleotide encoding the polypeptide as well as their utilization are described in detail.

(1) Polypeptide

The present inventors have found a novel glycosyltransferase, whose main substrate is a lignan, especially sesaminol and/or pinoresinol and have come to accomplish the present invention. The present inventors have further found that the novel glycosyltransferase described above catalyzes glycosidation of piperitol. So far the piperitol glycosides have not been found yet.

Throughout the specification, the term "polypeptide" is interchangeably used with "peptide" or "protein." A "fragment" of the polypeptide is intended to mean a partial fragment of the polypeptide. The polypeptide in accordance with the present invention may be isolated from natural supply sources or may be chemically synthesized.

The term "isolated" polypeptide or protein is intended to mean a polypeptide or protein which has been isolated from its natural environment. For example, the polypeptide or protein produced in host cells by recombination is considered to be isolated as in naturally occurring or recombinant polypeptide or protein substantially purified by optional and appropriate techniques.

The polypeptide in accordance with the present invention encompasses a purified natural product, a chemically synthetic product, and a product produced from prokaryotic hosts or eukaryotic hosts (including, e.g., bacterial cells, yeast cells, higher plant cells, insect cells and mammal cells) using recombinant techniques. Depending on the host used in the protocol of recombinant production, the polypeptide in accordance with the present invention may be glycosylated or non-glycosylated. In some cases, the polypeptide in accordance with the present invention may further comprise the starting modified methionine residue, as a result of a host-mediated process.

In one aspect, the present invention provides the polypeptide having the lignan glycosidation activity. As used herein, the "lignan glycosidation activity" is intended to mean the activity to glycosidate lignans, namely, the activity to transfer a sugar to lignans. In other words, throughout the specification, glycosidases and glycosyltransferases are interchangeably used.

In an embodiment, the polypeptide in accordance with the present invention is preferably a polypeptide consisting of the amino acid sequence represented by any one of SEQ ID NO: 2, 4, 82 or 91.

In another embodiment, the polypeptide in accordance with the present invention is preferably a variant of the polypeptide consisting of the amino acid sequence represented by one of SEQ ID NO: 2, 4, 82 or 91, and having the lignan glycosidation activity.

Such variants include variants containing deletion, insertion, inversion, repetition and type substitution (e.g., substitution of another residue for a hydrophilic residue; normally, a strongly hydrophilic residue is not substituted for a strongly hydrophobic residue, however). Particularly, "neutral" amino acid substitution in the polypeptide very little affects the activity of the polypeptide in general.

It is well known in the art that some amino acids in the amino acid sequence of the polypeptide may be easily modified without any significant effect on the structure or function of this polypeptide. It is also well known that not only in artificially modified ones but also in naturally occurring proteins, there are variants which do not significantly alter the structure or function of the protein.

One skilled in the art can easily modify one or more (e.g., 6) amino acids in the amino acid sequence of the polypeptide using well-known techniques. For example, an optional base in the polynucleotide encoding the polypeptide can be mutated by known point mutagenesis methods. Further by designing primers corresponding to optional sites of the polynucleotide encoding the polypeptide, deleted variants or added variants can be prepared. Further by using the methods described in the specification, it can be easily assayed if the prepared variants have a desired activity.

Preferred variants contain conservative or non-conservative amino acid substitution, deletion or addition, which are preferably silent substitution, addition and deletion, and particularly preferably conservative substitution. These variants do not change the activity of the polypeptide in accordance with the present invention.

The conservative substitution considered to be representative includes replacement of another amino acid for one amino acid in aliphatic amino acids Ala, Val, Leu and Ile; exchange of the hydroxyl residues Ser and Thr, exchange of the acidic residues Asp and Glu, replacement between the amide residues Asn and Gln, exchange of the basic residues Lys and Arg, and replacement between the aromatic residues Phe and Tyr.

As described above in detail, a further guidance about which amino acid alteration could be phenotypically silent (namely, which amino acid alteration could hardly exert significantly harmful effects on the function) can be found in Bowie, et al., "Deciphering the Message in Protein Sequences: Tolerance to Amino Acid Substitutions," Science 247: 1306-1310 (1990).

The polypeptide in accordance with this embodiment is a polypeptide having the lignan glycosidation activity, and is preferably a polypeptide consisting of
(a) the amino acid sequence represented by any one of SEQ ID NO: 2, 4, 82 or 91; or
(b) the amino acid sequence wherein one or several amino acids are deleted, inserted, substituted or added, in the amino acid sequence represented by any one of SEQ ID NO: 2, 4, 82 or 91.

As described above, these variant polypeptides are not limited to polypeptides having artificially induced variations by publicly known variant polypeptide production processes but may also be those isolated and purified from naturally occurring polypeptides.

The polypeptide in accordance with the present invention may be any polypeptide wherein the amino acids are linked through the peptide bond, but is not limited thereto and may be a conjugated polypeptide having a structure other than the polypeptide. As used herein, the "structure other than the polypeptide" includes a sugar chain, an isoprenoid group, etc. but is not particularly limited thereto.

The polypeptide in accordance with the present invention may contain an additional polypeptide. The additional polypeptide includes a polypeptide tagged with an epitope such as His, Myc, Flag, etc.

Also, the polypeptide in accordance with the present invention may be in such a state that the polynucleotide in accordance with the present invention encoding the polypeptide in accordance with the present invention is introduced into a host cell and its polypeptide is intracellularly expressed, or may be isolated and purified from cells, tissues, etc. Alternatively, the polypeptide in accordance with the present invention may be chemically synthesized.

In another embodiment, the polypeptide in accordance with the present invention may be expressed in a modified form, such as a fusion protein. For example, the region of additional amino acids, especially charged amino acids, of the polypeptide in accordance with the present invention may be added to the N-terminus of the polypeptide to improve the stability and persistence in host cells, during purification, or during subsequent handling and storage.

The polypeptide in accordance with this embodiment may be added to, e.g., a tag marker (a tag sequence or a marker sequence) at the N-terminus or C-terminus, which is a sequence encoding a peptide to facilitate purification of a fused polypeptide. Such sequences may be removed prior to final preparation of the polypeptide. In a certain preferred embodiment of this aspect of the present invention, the tag amino acid sequence is a hexahistidine peptide (the tag supplied by a pQE vector (Qiagen, Inc.)), among others, many of which are available publicly and/or commercially. As described in, e.g., Gentz, et al., Proc. Natl. Acad. Sci. USA 86: 821-824 (1989) (which is hereby incorporated by reference), hexahistidine provides convenient purification for a fusion protein. The "HA" tag is another peptide useful for purification, which corresponds to an epitope derived from the influenza hemagglutinin (HA) protein, described by Wilson et al., Cell 37: 767 (1984) (which is hereby incorporated by reference). Other such fusion proteins include the polypeptide in accordance with this embodiment fused to Fc at the N- or C-terminus, or its fragments.

In yet another embodiment, the polypeptide in accordance with the present invention may be recombinantly produced or chemically synthesized, as will be described below in detail.

Recombinant production can be carried out using techniques well known in the art, and can be performed using, for example, the vectors and cells as will be described below in detail.

Synthetic peptides can be synthesized by using the methods described publicly known. For example, Houghten describes a simple method for synthesis of large numbers of peptides, such as 10-20 mg of 248 different 13-residue peptides representing single amino acid variants of a segment of the HA1 polypeptide which are prepared and characterized in less than 4 weeks; Houghten, R. A., Proc. Natl. Acad. Sci. USA, 82: 5131-5135 (1985). This "Simultaneous Multiple Peptide Synthesis (SMPS)" process is further described in U.S. Pat. No. 4,631,211 issued to Houghten et al. (1986). In this procedure the individual resins for the solid-phase synthesis of various peptides are contained in separate solvent-permeable packets, which enables the optimal use of the many identical repetitive steps involved in solid-phase methods. A completely manual procedure allows 500-1000 or more syntheses to be conducted simultaneously (Houghten et al., supra, 5134). These literatures are hereby incorporated by reference.

The polypeptide in accordance with the present invention is useful in the method for glycosidation of lignans to produce lignan glycosides and in a kit therefor.

The polypeptide in accordance with the present invention can catalyze the glycosidation reaction of lignans (especially, pinoresinol, sesaminol or piperitol).

As described above, it is sufficient for the polypeptide in accordance with the present invention to have at least the amino acid sequence represented by any one of SEQ ID NO: 2, 4, 82 or 91. In other words, it should be noted that polypeptides consisting of the amino acid sequence represented by any one of SEQ ID NO: 2, 4, 82 or 91 and an optional amino acid sequence having a specific function (e.g., a tag) are also included within the present invention. Furthermore, the amino acid sequence represented by any one of SEQ ID NO: 2, 4, 82 or 91 and the optional amino acid sequence may be linked via an appropriate linker peptide in such a way that the respective functions are not inhibited.

Also, the polypeptide in accordance with the present invention has the activity to glycosidate piperitol, in addition to the activity to glycosidate sesaminol or pinoresinol. Accordingly, utilization of the polypeptide should not be limited only to the glycosidation of sesaminol or pinoresinol to produce these glycosides.

In other words, the object of the present invention is to provide the polypeptide having the activity to glycosidate lignans, but does not reside in the methods of producing the polypeptides specifically described in the specification, and so on. It should thus be noted that polypeptides having the activity to glycosidate lignans produced by methods other than the methods described above are also within the technical scope of the present invention.

(2) Polynucleotide

In one aspect, the present invention provides the polynucleotide encoding the polypeptide in accordance with the present invention having the lignan glycosidation activity. As used herein, the term "polynucleotide" is interchangeably used with "gene," "nucleic acid" or "nucleic acid molecule," and is intended to mean a polymeric form of nucleotides. As used herein, the term "base sequence" is interchangeably used with "nucleic acid sequence" or "nucleotide sequence," and is given as the sequence of deoxyribonucleotides (abbreviated as A, G, C and T). Furthermore, the "polynucleotide comprising the base sequence represented by SEQ ID NO: 1 or a fragment thereof" is intended to mean a polynucleotide comprising a sequence given by the respective deoxynucleotides A, C, C and/or T in SEQ ID NO: 1, or a fragmental portion thereof.

The polynucleotide in accordance with the present invention can be present in the form of RNA (e.g., mRNA) or DNA (e.g., cDNA or genomic DNA). The DNA may be double-stranded or single-stranded. Single-stranded DNA or RNA may be a coding strand (also known as a sense strand), or it may be a non-coding strand (also referred to as an anti-sense strand).

As used herein, the term "oligonucleotide" is intended to mean linked nucleotides of, e.g., several to several tens and interchangeably used with "polynucleotide." In the oligonucleotide, a short string of nucleotides is called a dinucleotide (dimer) or a trinucleotide (trimer), and a long string of nucleotides is expressed by the number of nucleotides polymerized, such as a 30-mer or a 100-mer. The oligonucleotide may be produced as a fragment of longer polynucleotide or chemically synthesized.

The fragment of the polynucleotide in accordance with the present invention is intended to mean a fragment of at least 12 nt (nucleotides), preferably about 15 nt, more preferably at least about 20 nt, much more preferably at least about 30 nt and most preferably at least about 40 nt, in length. By the fragment of at least 20 nt in length, it is intended to mean a fragment containing consecutive 20 or more bases derived from the base sequence represented by, for example, SEQ ID NO: 1. By referring to the specification, the base sequence represented by SEQ ID NO: 1 is provided and one skilled in the art can easily produce a DNA fragment based on SEQ ID NO: 1. For instance, digestion with a restricted endonuclease or ultrasonic shear can be readily used to prepare fragments with various sizes. Alternatively, such fragments can be prepared synthetically. Appropriate fragments (oligonucleotides) are synthesized on an Applied Biosystems Incorporated (ABI, 850 Lincoln Center Dr., Foster City, Calif. 94404) Model 392 synthesizer, etc.

Furthermore, the polynucleotide in accordance with the present invention can be fused to a polynucleotide encoding the aforesaid tag marker (tag sequence or marker sequence) at the 5' or 3' end.

In an embodiment, the polynucleotide in accordance with the present invention is preferably a polynucleotide encoding the polypeptide having the lignan glycosidation activity or its variants.

In yet another aspect, the present invention provides variants of the polynucleotide, which encodes the polypeptide having the lignan glycosidation activity. The "variants" may occur naturally, such as a naturally occurring allelic variant. By the "allelic variant" it is intended to mean one of several alternate forms of a gene occupying a given locus on a chromosome of an organism. Non-naturally occurring variants may be produced, for example, by using mutagenesis techniques well known in the art.

In an embodiment, the polynucleotide in accordance with the present invention is preferably variants in which one or several bases are deleted, inserted, substituted or added in the base sequence of the polynucleotide encoding the polypeptide having the lignan glycosidation activity. The variants may be altered in coding regions, non-coding regions, or both regions. Alterations in the coding regions may produce conservative or non-conservative amino acid deletions, insertions, substitutions or additions.

In an embodiment, the polynucleotide in accordance with the present invention is a polynucleotide encoding the polypeptide having the lignan glycosidation activity, and preferably either one of:
(a) a polynucleotide consisting of the base sequence represented by any one of SEQ ID NO: 1, 3, 81 or 90; or
(b) a polynucleotide comprising the base sequence in which one or several bases are deleted, inserted, substituted or added in the base sequence represented by any one of SEQ ID NO: 1, 3, 81 or 90.

In another embodiment, the polynucleotide in accordance with the present invention is preferably an isolated polynucleotide, including a polynucleotide encoding the polypeptide having the lignan glycosidation activity, and a polynucleotide, which hybridizes to said polynucleotide, under stringent hybridization conditions.

In this embodiment, the polynucleotide in accordance with the present invention is a polynucleotide encoding the polypeptide having the lignan glycosidation activity, and preferably either one of:
(a) a polynucleotide consisting of the base sequence represented by any one of SEQ ID NO: 1, 3, 81 or 90; or
(b) a polynucleotide hybridizable under stringent conditions to a polynucleotide consisting of a base sequence complementary to the base sequence represented by any one of SEQ ID NO: 1, 3, 81 or 90.

Hybridization may be performed by such a well-known method as described in Sambrook et al., Molecular Cloning, A Laboratory Manual, 2nd Ed., Cold Spring Harbor Laboratory (1989). Higher temperature and lower salt concentration normally result in higher stringency (difficulty of hybridization) so that a more homologous polynucleotide can be acquired. Appropriate temperature for the hybridization varies depending upon base sequence or length of the base sequence. Where a DNA fragment consisting of 18 bases encoding 6 amino acids is used as a probe, the temperature is preferably 50° C. or lower.

As used herein, the term "stringent hybridization conditions" is intended to mean incubation at 42° C. overnight in a hybridization solution (containing 50% formamide, 5×SSC (150 mM NaCl, 15 mM trisodium citrate), 50 mM sodium phosphate (pH 7.6), 5×Denhardt's solution, 10% dextran sulfate and 20 µg/ml of denatured sheared salmon sperm DNA), followed by washing the filters in 0.1×SSC at about 65° C. By a polynucleotide which hybridizes to a "portion" of a polynucleotide, it is intended to mean a polynucleotide hybridizing to at least about 15 nucleotides (nt), and more preferably at least about 20 nt, still more preferably at least about 30 nt, and even more preferably about 30-70 nt of the reference polynucleotide. These polynucleotides, which hybridize to a "portion" of polynucleotides, are also useful as diagnostic probes and primers as discussed in the specification in more detail.

In a further embodiment, the present invention provides the polynucleotide consisting of the base sequence which is identical by at least 80%, preferably at least by 85%, 90%, 92%, 95%, 96%, 97%, 98% or 99%, to the base sequence represented by any one of SEQ ID NO: 1, 3, 81 or 90.

In this embodiment, the polynucleotide in accordance with the present invention is a polynucleotide encoding the polypeptide having the lignan glycosidation activity and preferably either one of:
(a) a polynucleotide consisting of the base sequence represented by any one of SEQ ID NO: 1, 3, 81 or 90; or
(b) a polynucleotide consisting of a base sequence which has at least 80% identical to the base sequence represented by any one of SEQ ID NO: 1, 3, 81 or 90.

For example, by the "polynucleotide consisting of a base sequence which has at least 95% identical with the reference (QUERY) base sequence of the polynucleotide encoding the polypeptide in accordance with the present invention," it is intended to mean that the polynucleotide is identical to the reference base sequence, except that the reference base sequence may contain up to 5 mismatches per 100 nucleotides (bases) of the reference base sequence of the polynucleotide encoding the polypeptide in accordance with the present invention. In other words, to obtain a polypeptide having a base sequence at least 95% identical with the reference base sequence, up to 5% of the bases in the reference sequence may be deleted, substituted with another base(s), or base(s) as much as 5% of the all bases in the reference sequence may be inserted into the reference sequence. These mismatches in the reference sequence may occur at the 5'- or 3'-terminal position of the reference base sequence or anywhere between those terminal positions, interspersed either individually among residues in the reference sequence or in one or more contiguous groups within the reference sequence. As described herein, this reference sequence may be the polynucleotide encoding the amino acid sequence represented by any one of SEQ ID NO: 2, 4, 82 or 91, variants, derivatives or analogs thereof.

Whether any arbitrary particular nucleic acid molecule is identical by at least 80%, 85%, 90%, 92%, 95%, 96%, 97%, 98% or 99% with the base sequence represented by any one of SEQ ID NO: 1, 3, 81 or 90 can be determined by using known computer programs (e.g., the Bestfit program (Wisconsin Sequence Analysis Package, Version 8 for Unix (registered trademark), Genetics Computer Group, University Research Park, 575 Science Drive, Madison, Wis. 53711). Bestfit uses the local homology algorithm of Smith and Waterman to find the best segment of homology between two sequences (Advances in Applied Mathematics 2: 482-489 (1981)). When using Bestfit or any other sequence alignment program to determine whether a particular sequence is, e.g., 95% identical with the reference base sequence according to the present invention, the parameters are set in such a manner that the percentage of identity is calculated over the full length of the reference base sequence and gaps in homology of up to 5% of the total number of nucleotides in the reference sequence are allowed.

In a specific embodiment, the identity (also termed as a global sequence alignment) between a reference (QUERY) sequence (the sequence in accordance with the present invention) and a target sequence is determined by using the FASTDB computer program based on the algorithm of Brutlag, et al. (Comp. App. Biosci., 6: 237-245 (1990)). Preferred parameters used in the FASTDB alignment of DNA sequences to calculate identity percentage are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the target base sequence (whichever is shorter). According to this embodiment, if the target sequence is shorter than the QUERY sequence because of 5' or 3' deletions (not because of internal deletions), a manual correction is made, taking into account the fact that the FASTDB program does not account for the 5' and 3' truncations of the target sequence when calculating the identity percentage. For the target sequence truncated at the 5' end or 3' end relative to the QUERY sequence, the identity percentage is corrected by calculating the number of bases of the QUERY sequence that are 5' and 3' of the target sequence and are not matched/aligned, as a percent of the total bases of the QUERY sequence. Whether the nucleotide is matched/aligned is determined by the results of the FASTDB sequence alignment. Then, this percentage is subtracted from the identity percentage, calculated by the above FASTDB program using the specified parameters to arrive at the final identity percentage score. This corrected score is the one used for the purposes of this embodiment. Only the bases outside the 5' and 3' bases of the target sequence, as shown by the FASTDB alignment, which are not matched/aligned with the QUERY sequence, are calculated for the purposes of manually adjusting the identity percentage score. For example, a 90 base target sequence is aligned to a 100 base QUERY sequence to determine the identity percentage. The deletions occur at the 5' end of the target sequence and thus, the FASTDB alignment does not show any match/alignment of the first 10 bases at the 5' end. The 10 unpaired bases represent 10% of the sequence (the number of bases at the 5' and 3' ends not matched/total number of bases in the QUERY sequence) and for this reason, 10% is subtracted from the identity percentage score calculated by the FASTDB program. If the remaining 90 bases were perfectly matched, the final identity percentage would be 90%. In another example, a 90 base target sequence is compared to a 100 base QUERY sequence. In this case, the deletions are internal deletions so that there are no bases on the 5' or 3' ends of the target sequence that are not matched/aligned with the QUERY sequence. The identity percentage calculated by FASTDB is not manually corrected in this case. Again, only the bases at the 5' and 3' ends of the target sequence, which are not matched/aligned with the QUERY sequence, are manually corrected. No other manual corrections are made for the purposes of this embodiment.

In another aspect, the present invention provides the oligonucleotide comprising a fragment of the polynucleotide described above, or its complementary sequence.

Even where the oligonucleotide in accordance with the present invention does not encode the polypeptide for lignan glycosidation, one skilled in the art readily understands that the polynucleotide in accordance with the present invention could be used as a primer for polymerase chain reaction (PCR) to produce the polypeptide in accordance with the present invention. Another utilization of the oligonucleotide in accordance with the present invention that does not encode the polypeptide for lignan glycosidation includes the following: (1) isolation of the lignan glycosidase gene from a cDNA library or its allelic variants or splicing variants; (2) in situ hybridization (e.g., "FISH") to metaphase chromosomal spreads to provide the precise chromosomal location of the lignan glycosidase gene (as described in Verma, et al., Human Chromosomes: A Manual of Basic Techniques, Pergamon Press, New York (1988)); and (3) northern blot analysis for detecting the expression of lignan glycosidase RNA in particular tissues.

The polynucleotide or oligonucleotide in accordance with the present invention includes not only double-stranded DNA but single-stranded DNA or RNA such as sense strand and antisense strand, which constructs the double-stranded DNA. The polynucleotide or oligonucleotide in accordance with the present invention can be used as a tool for gene expression manipulation via an antisense RNA mechanism. By means of the antisense RNA technique, a decrease of the gene product derived from endogenous gene is observed. By introducing the oligonucleotide in accordance with the present invention, the level of the polypeptide having the lignan glycosidation activity can be reduced so that the content or content ratio of lignan glycosides in a plant can be controlled (increased or decreased). The polynucleotide or oligonucleotide in accordance with the present invention may be those having a sequence from the untranslated region (UTR), a sequence from vector sequences (including expression vector sequences), etc.

A method for acquiring the polynucleotide or oligonucleotide in accordance with the present invention includes various known methods for isolating DNA fragments containing the polynucleotide or oligonucleotide in accordance with the present invention. For instance, a probe specifically hybridizing to a part of the base sequence of the polynucleotide in the present invention is prepared, followed by screening of a genomic DNA library or cDNA library. Such a probe may be a polynucleotide (oligonucleotide) which specifically hybridizes at least to a part of the base sequence of the polynucleotide in accordance with the present invention or its complementary sequence.

Such a polynucleotide as screened by the hybridization includes naturally occurring polynucleotides (e.g., a polynucleotides derived from plants such as plants of the Pedaliaceae, Bryophyta, etc.) but may also be polynucleotides derived from other than plants.

An alternative method of acquiring the polynucleotide in accordance with the present invention further includes a method using PCR. This PCR amplification method comprises, e.g., the step of preparing primers using the 5'-end and/or 3'-end sequences (or their complementary sequences) of cDNA of the polynucleotide in accordance with the present invention and the step of amplifying by PCR utilizing these primers as a template of genomic DNA (or cDNA), etc. By using this method, DNA fragments containing the polynucleotide in accordance with the present invention can be acquired in large quantities.

Supply sources to acquire the polynucleotide in accordance with the present invention are not particularly limited but include preferably biological materials containing piperitol, sesaminol or pinoresinol. As used herein, the term "biological material" is intended to mean a biological sample (a tissue sample or cell sample obtained from an organism). In EXAMPLES described below, sesame is employed but not limited thereto.

By using the polynucleotide in accordance with the present invention, the polypeptide having the lignan glycosidation activity can be synthesized in transformants or cells.

By using the polynucleotide in accordance with the present invention, an organism that expresses the polypeptide having the lignan glycosidation activity can be readily detected by detecting the hybridizing polynucleotide.

The oligonucleotide in accordance with the present invention can be utilized as a hybridization probe to detect the polynucleotide encoding the polypeptide having the lignan glycosidation activity or as a primer to amplify the said polynucleotide, whereby the organism or tissue capable of expressing the polypeptide having the lignan glycosidation activity can be easily detected. Moreover, by using the aforesaid oligonucleotide as an antisense oligonucleotide, the expression of the polypeptide having the lignan glycosidation activity can be repressed in the organism described above, or its tissues or cells.

In the polynucleotide in accordance with the present invention, the polypeptide encoded by said polynucleotide has the activity to glycosidate piperitol, in addition to the activity to glycosidate sesaminol or pinoresinol. Thus, utilization of the polynucleotide in accordance with the present invention should not be limited only to the glycosidation of sesaminol or pinoresinol to produce these glycosides.

In other words, the object of the present invention is to provide the polynucleotide encoding the polypeptide, which has the activity to glycosidate piperitol, sesaminol or pinoresinol, and the oligonucleotide, which hybridizes the polynucleotide, but does not reside in the methods of producing the polynucleotides and oligonucleotides specifically described in the specification, and so on. It should thus be noted that such polynucleotides encoding the polypeptide having the activity to glycosidate piperitol, sesaminol or pinoresinol, which are acquired by methods other than those described above, are also within the technical scope of the present invention.

(3) Utilization of the Polypeptide or Polynucleotide in Accordance with the Present Invention The present invention further provides the method of controlling (increasing or decreasing) the amount of lignans and lignan glycosides in organisms (preferably plants) by using the polypeptide or polynucleotide in accordance with the present invention, as well as utilization of the controlled organisms (preferably plants).

(A) Vector

The present invention provides a vector which is used to produce the polypeptide having the lignan glycosidation activity. The vector in accordance with the present invention may be a vector used for in vitro translation or a vector used for recombinant expression.

The vector in accordance with the present invention is not particularly limited, so long as the vector comprises the polynucleotide in accordance with the present invention. For example, the vector includes a recombinant expression vector inserted with cDNA of the polynucleotide encoding the polypeptide having the lignan glycosidation activity, and the like. A method of producing the recombinant expression vector includes a method which comprises using a plasmid, phage or cosmid, etc., but is not particularly limited thereto.

The vector is not particularly limited to specific kinds but a vector may be appropriately chosen such that it can be expressed in host cells. In other words, a promoter sequence is appropriately chosen to ensure the expression of the polynucleotide in accordance with the present invention depending upon kind of host cells, and this promoter and the polynucleotide in accordance with the present invention are incorporated into various plasmids, etc., and then the vectors thus obtained may be used as expression vectors.

The expression vector in accordance with the present invention contains expression controlling regions (e.g., promoter, terminator and/or a replication origin, etc.) depending upon a biological species of the host to be introduced. As the promoter for bacteria, there are employed conventional promoters (e.g., a trc promoter, a tac promoter, a lac promoter, etc.). As the promoter for yeast, a glyceraldehyde 3-phosphate dehydrogenase promoter, a PHO5 promoter, etc. may be used. The promoter for filamentous fungi includes, for example, promoters of amylase, trp C, etc. The promoter for animal cell hosts includes viral promoters (e.g., SV40 early promoter, SV40 late promoter, etc.). The expression vector may be prepared by conventional methods using restriction enzymes and/or ligases, etc. The host cells may be transformed with the expression vector according to conventional procedures.

After the host transformed using the expression vector described above is incubated, cultivated or raised, the objective protein can be recovered and purified from the culture or the like in a conventional manner (e.g., filtration, centrifugation, disruption of cells, gel filtration chromatography, ion exchange chromatography, etc.).

The expression vector preferably contains at least one selection marker. Such a marker includes dihydrofolate reductase or neomycin resistance for eukaryotic cell culture and tetracycline or ampicillin resistance genes for the culture in *E. coli* and other bacteria.

By using the selection marker described above, it can be confirmed whether or not the polynucleotide in accordance with the present invention is introduced into a host cell and further whether or not the polynucleotide is certainly expressed in a host cell. Alternatively, the polypeptide in accordance with the present invention may be expressed as a fused polypeptide; for example, a green fluorescent polypeptide GFP (Green Fluorescent Protein) derived from jelly fish or *Aequorea victoria* may be used as a marker to express the polypeptide in accordance with the present invention in the form of a GFP-fused polypeptide.

The host cells described above are not particularly limited and various cells heretofore known may be advantageously used. Specific examples include, but not limited to, bacterial such as *Escherichia coli*, etc., yeasts (*Saccharomyces cerevisiae, Schizosaccharomyces pombe*), oocytes of *Caenorhabditis elegans* or *Xenopus laevis*, etc. Culture media and conditions suitable for the host cells described above are well known in the art.

Introduction of the vector, namely, transformation methods are not particularly limited and can be advantageously effected by any methods known in the art, which methods include the electroporation, calcium phosphate, liposome and DEAE-dextran methods, etc. Also, where the polypeptide in accordance with the present invention is transferred and expressed in insects, an expression system using baculovirus may be employed.

By using the vector in accordance with the present invention, the polynucleotide described above can be introduced into organisms or cells, and the polypeptide having the lignan glycosidation activity can be expressed in the organisms or cells. In addition, the vector in accordance with the present invention can be used in a cell-free protein synthesis system to synthesize the polypeptide having the lignan glycosidation activity.

As described above, the vector in accordance with the present invention comprises at least the polynucleotide encoding the polypeptide in accordance with the present invention. In other words, it should be noted that vectors other than the expression vectors are also within the technical scope of the present invention.

That is, the object of the present invention is to provide the vector comprising the polynucleotide encoding the polypeptide in accordance with the present invention, and not only to provide the respective vector and cell species specifically described herein and methods of producing these vectors or introducing these cells. It should thus be noted that vectors obtained by other methods of producing vectors using vector species other than those described above are also within the technical scope of the present invention.

(B) Transformant or Cell

The present invention provides transformants or cells in which the polynucleotide encoding the polypeptide having the lignan glycosidation activity described above is introduced. As used herein, the term "transformant" is intended to mean not only a tissue or organ but also an individual organism.

Methods of preparing (producing) transformants or cells are not particularly limited, and include, for example, the aforesaid method which involves transformation through incorporation of a recombinant vector into a host. Organisms to be transformed are not particularly limited, and examples include various microorganisms, plants or animals illustratively given for the host cells described above.

The transformants or cells in accordance with the present invention are characterized in that their compositions are altered from those in naturally occurring lignans and/or lignan glycosides. The transformants or cells in accordance with the present invention are preferably plants or their progeny, or tissues derived therefrom, more preferably, sesame, *Forsythia intermedia* or *Linum usitatissimum*. In these transformants or cells, the content of lignan glycosides in organisms capable of producing lignans can be increased or decreased by the method of controlling the content of lignan glycosides in accordance with the present invention.

In an embodiment, the transformant in accordance with the present invention can be a plant transformant. The plant transformant in accordance with this embodiment can be acquired by introducing a recombinant vector comprising the polynucleotide in accordance with the present invention into a plant in such a manner that the polypeptide encoded by the said polynucleotide can be expressed.

Where the recombinant expression vector is used, the recombinant expression vector used to transform the plant is not particularly limited as far as the vector is capable of expressing the polynucleotide in accordance with the present invention in a plant. Examples of such vectors include a vector bearing a promoter capable of constitutively expressing the polynucleotide in plant cells (e.g., a 35S promoter of cauliflower mosaic virus) in plant cells, and a vector inducibly activated by external stimulation.

Plants which are to be the target of transformation in the present invention may be any of entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells, or various types of plant cells (e.g., suspension culture cells), protoplasts, leaf slices, callus, and the like. Specific examples of plant species which are used for transformation include, but are not limited to, those belonging to the Monocotyledoneae or the Dicotyledoneae.

For transformation of genes into plants, conventional transformation methods known to one skilled in the art (e.g., the *Agrobacterium* method, gene gun, the PEG method, the electroporation method, etc.) are used. For example, the *Agrobacterium*-mediated method and the method of directly introducing into plant cells are well known. When the *Agrobacterium* method is used, the constructed plant expression vector is introduced into an appropriate *Agrobacterium* strain (e.g., *Agrobacterium tumefaciens*), followed by infection of aseptically cultured leaf discs with this strain according to the leaf disc method (Hirobumi Uchimiya, Manuals for Plant Gene Manipulation (1990), 27-31, Kodansha Scientific Co., Ltd., Tokyo). Thus, the transgenic plant can be obtained. In addition, the method of Nagel, et al. (Micribiol. Lett., 67, 325 (1990)) may be used. This method involves introducing first, e.g., an expression vector into *Agrobacterium* and then introducing the transformed *Agrobacterium* into plant cells or plant tissues according to the method described in Plant Molecular Biology Manual (S. B. Gelvin, et. al., Academic Press Publishers). Herein, the "plant tissue" includes callus, which is obtained by culturing plant cells. When the transformation is carried out using the *Agrobacterium* method, binary vectors (pBI121 or pPZP202, etc.) can be used.

For direct transfer of genes into plant cells or plant tissues, the electroporation method and the gene gun method are known. When the gene gun is used, entire plant bodies, plant organs or plant tissues per se may be used, or may be used after preparation of protoplasts. The samples thus prepared can be bombarded using a gene transfer apparatus (e.g., PDS-1000 (BIO-RAD, Inc.), etc.). Bombardment conditions vary depending upon type of the plant or sample. Normally, the sample is bombarded under a pressure of about 450-2000 psi at a distance of 4-12 cm.

The cells or plant tissues in which the gene is introduced are first selected by chemical resistance such as hygromycin resistance, etc. and then regenerated into plant bodies in a conventional manner. Regeneration of plant bodies from the transformant cells can be performed by methods known to one skilled in the art, depending upon kind of plant cells.

When a plant culture cell is used as a host, transformation is preformed by introducing the recombinant vector into culture cells by the gene gun method, the electroporation method, etc. Callus, shoots, hairy roots, etc. resulted from the transformation can be used directly in cell culture, tissue culture or organ culture. Furthermore, they can be regenerated into plant bodies by conventional plant tissue culture methods through administration of plant hormones (e.g., auxin, cytokinin, gibberellin, abscisic acid, ethylene, brassinolide, etc.) at appropriate concentrations.

Whether or not the gene has been introduced into the host can be confirmed by PCR, Southern hybridization, northern hybridization, or the like. For example, DNA is prepared from the transgenic plant and DNA-specific primers are then designed for PCR. The PCR can be performed under the same conditions as used for the preparation of plasmids described above. Subsequently, the amplified product is subjected to agarose gel electrophoresis, polyacrylamide gel electrophoresis, capillary electrophoresis, etc. and stained with ethidium bromide, SYBR Green solution, etc. By detecting the amplified product as a single band, it can be confirmed that transformation has occurred. Alternatively, PCR may be performed using primers previously labeled with a fluorescent dye or the like, and, then the amplified product can be detected. In addition, a method may be employed in which the amplification product is bound to the solid phase of a microplate or the like to enable confirmation of the amplification product by means of fluorescence or enzyme reactions, or the like.

Once the transgenic plant wherein the polynucleotide in accordance with the present invention has been integrated into the genome is acquired, its progeny can be obtained by sexual or asexual reproduction of the plant body. Also, the plant body can be mass-produced by acquiring from the plant body or its progeny or clones thereof, e.g., seeds, fruits, cut panicles, tubers, tuberous roots, strains, callus, protoplasts, etc., and then using them as the origin. Accordingly, the present invention also encompasses the plant body in which the polynucleotide in accordance with the present invention is expressibly introduced, or progenies of the plant body having the same property as in the plant body, and tissues derived therefrom.

Moreover, the transformation methods for various plants are already reported. Examples of transformable plants may include, but not be limited to, sesame, rice plant, tobacco, barley, wheat, rapeseed, potato, tomato, poplar, banana, eucalyptus, sweet potato, soybean, alfalfa, lupinus, corn, cauliflower, rose, chrysanthemum, carnation, snapdragon, cyclamen, orchid, Prairie gentian, freesia, gerbera, gladiolus, gypsophila, kalancoe, lily, pelargonium, geranium, petunia, torenia, tulip, *Forsythia intermedia, Arabidopsis thaliana, Lotus japonicus*, and so on.

In a preferred embodiment, the transformant in accordance with the present invention can be prepared using sesame. The method of preparing the transformant of sesame includes such a known method as described in, for example, T. Asamizu: Transformation of sesame plants using MAT vector system: introduction of fatty acid desaturase genes, Sesame Newsletter, 16: 22-25 (2002).

By using the transgenic sesame thus acquired, lignan glycosides are produced in the sesame and the lignan glycosides (piperitol, sesaminol and/or pinoresinol) can then be produced at low costs by an environment-friendly production process.

In another preferred embodiment, a tobacco plant can be used preferably as the transformant in accordance with the present invention. Like petunia the tobacco plant is a typical plant which readily undergoes transformation and is capable of regenerating from a cell wall-removed single cell (protoplast) to a single plant body. This single plant body regenerated does not result in a chimeric pattern unlike the single body derived from multiple cells so that its transformants can be efficiently produced.

A preferred example of the transformation method for tobacco is the leaf disc method. According to this method, operations are easy and multiple independent transformants can be obtained from a single leaf disc. The transformation method is described in, e.g., "SHIN-SEIBUTSU KAGAKU JIKKEN-NO-TEBIKI (New Guidance of Biochemical Experiment) 3: Isolation/Analysis of Nucleic Acid and Gene Research Method, published by Kagaku Dojin, 1996."

Specifically, a leaf disc is excised from an aseptically cultivated tobacco leaf on a sterile Petri dish and the leaf disc cut is pre-incubated in a NB medium. Next, the pre-incubated leaf disc is impregnated with an *Agrobacterium*-infected bacteria solution for co-incubation. The leaf disc is embedded in a NB medium supplemented with carbenicillin and kanamycin. After subculture is made until shoots generate via callus formation from the leaf disc, the shoots are obtained. When the shoots grow up and distinction becomes clear between the stems and leaves, the shoots are excised from the stems and transferred to a MS medium free of any antibiotic or any hormone. After the excised shoots produce roots, the roots are cultivated in a greenhouse. The shoots are then transferred to a hormone-supplemented medium to promote rooting. At the same time, the leaves are partially excised from the shoots and transplanted to an assay medium supplemented with carbenicillin and kanamycin. Approximately 10 days after the transplantation, the leaves which induce callus are regarded as kanamycin-resistant individuals and thus recovered, whereas the leaves which turn brown are regarded as kanamycin-sensitive individuals and thus discarded.

By using the transgenic tobacco thus obtained, the lignan glycosides are produced in the tobacco and thus the lignan glycosides (piperitol, sesaminol and/or pinoresinol) can thus be produced at low costs by an environment-friendly production process.

In yet another preferred embodiment, a rice plant can be advantageously employed as the transformant in accordance with the present invention. An embodiment for preparing the rice transformant is described below.

The polynucleotide in accordance with the present invention is introduced into binary vector pPZP202 harboring a hygromycin-resistant gene to construct the transformation vector. The polynucleotide in accordance with the present invention is operably linked to promoter CaMV35S in-frame.

Using the resulting transformation vector, *Agrobacterium tumefaciens* EHA101 is transformed by electroporation under selection with 50 mg/l kanamycin and hygromycin. The resulting *Agrobacterium* transformant is stored frozen until use.

Brown rice grains are prepared by removing lemmas from wild-type seeds, sterilized with 70% ethanol for 3 minutes and then washed 3 times with sterilized distilled water. The grains are further sterilized with 50% sodium hypochlorite for 30 minutes and then washed 5 times with sterilized distilled water. The brown rice grain is placed on a callus induction medium containing N6 medium (Chu et al., 1975, Sci. Sinica, 18, 659-668) supplemented with 30 g/l sucrose, 0.3 g/l Casamino acid, 2.8 g/l proline and 2.0 mg/l 2,4-D, which is solidified with 4.0 g/l Gelrite. Prior to autoclaving, pH of the medium is adjusted to 5.8. The brown rice grain is grown at 28° C. for 4 weeks in bright light to produce the callus having a size of about 5 mm. This callus is used for *Agrobacterium* infection.

The *Agrobacterium* stored frozen in glycerol is cultured on an AB medium (Chilton et al., 1974, Proc. Natl. Acad. Sci. USA, 71, 3672-3676) supplemented with 20 mg/l kanamycin, 50 mg/l hygromycin and 100 mg/l spectinomycin, whose pH is adjusted to 7.2 and solidified with 15 g/l agar, at 28° C. for 3 days in the dark. The *Agrobacterium* bacterial cells are collected and suspended in liquid AAM medium (Hiei, et al., 1994) supplemented with 10 mg/l acetonesyringone (Hiei et al., 1994, Plant J., 6, 271-282). The callus described above is immersed in the resulting suspension for 2 minutes and blotted on a sterile paper towel to remove excess moisture. The callus is then transferred to the 10 mg/l acetonesyringone-containing callus induction medium described above. Co-cultivation is carried out at 28° C. for 3 days for *Agrobacterium* infection. The resulting infected callus is washed 10 times with sterile distilled water and finally once with sterile distilled water containing 500 mg/l carbenicillin to remove excess moisture with a sterile paper towel. This callus is cultivated at 28° C. for 2 weeks in the callus induction medium described above supplemented with 10 mg/l acetonesyringone, 50 mg/l hygromycin and 300 mg/l carbenicillin, followed by further cultivation in the callus induction medium supplemented with 50 mg/l hygromycin and 100 mg/l carbenicillin for 4 weeks. Hygromycin-resistant callus is selected and transferred to a regeneration medium containing a MS basal medium (Murashige and Skoog, 1962, Physiol. Plant., 15, 473-497), pH 5.8, supplemented with 30 g/l sucrose, 30 g/l sorbitol, 2 g/l Casamino acid, 2.2 mg/l kinetin, 1.0 mg/l NAA, 100 mg/l carbenicillin, 50 mg/l hygromycin and 4 g/l Gerlite.

The transformant thus obtained can be readily regenerated in a hygromycin-containing regeneration medium and transferred to soil for cultivation.

By using the transgenic rice plant thus obtained, lignan glycosides are produced in the rice plant, and the lignan glycosides (piperitol, sesaminol and/or pinoresinol) can be produced at low costs by an environment-friendly production process.

When an organism contains a lignan (especially pinoresinol, sesaminol or piperitol), irrespective of the species of organism, the transformant in accordance with the present invention can produce glycosides of the lignan by introducing the aforesaid polynucleotide therein.

When the transformant, into which a recombinant expression vector comprising the polynucleotide encoding the polypeptide in accordance with the present invention has been transduced, is used, the transformant can catalyze the reaction to glycosidate endogenous lignans present in organisms such as plants. Thus, the lignan glycosides can be mass-produced at low costs by an environment-friendly production process. In addition, the present invention can provide inexpensive foodstuff or industry products through the mass-production of lignan glycosides.

By using the transformant in accordance with the present invention, the polypeptide which catalyzes the reaction for lignan glycosidation can be provided at low costs under environment-friendly conditions.

In an embodiment, the cells in accordance with the present invention may be a variety of bacterial cells. The cells in accordance with this embodiment are acquired by introducing a recombinant vector comprising the polynucleotide in accordance with the present invention in cells in such a manner that the polypeptide encoded by the polynucleotide can be expressed.

Prokaryotes or eukaryotes may be used as hosts. As the prokaryotic host, bacteria belonging to, for example, the genus *Escherichia* (e.g., *Escherichia coli*, etc.), bacteria belonging to, for example, the genus *Bacillus* (e.g., *Bacillus subtilis*, etc.) may be used. As the eukaryotic host, lower eukaryotes (e.g., eukaryotic microorganisms such as yeast, filamentous fungi, etc.). The yeast includes microorganisms belonging to the genus *Saccharomyces* (e.g., *Saccharomyces cerevisiae*, etc.) and the filamentous fungi include microorganisms belonging to the genus *Aspergillus* (e.g., *Aspergillus oryzae*, *Aspergillus niger*, etc.), and microorganisms belonging to the genus *Penicillium*. Animal cells or plant cells may also be used as hosts. The animal cells include cells from mice, hamsters, monkeys, humans, etc. In addition, insect cells (e.g., silkworm cells or silkworm imagines) may also be used as hosts.

According to the disclosure in the specification, one skilled in the art can readily understand that once a recombinant expression vector comprising the polynucleotide encoding the polypeptide having the lignan glycosidation activity is transduced, the lignan glycosidation capability can be imparted to organisms over a wide range from bacteria to higher plants.

When an organism contains a lignan (especially pinoresinol, sesaminol or piperitol), irrespective of the species of organism, the cells in accordance with the present invention can produce glycosides of the lignan by introducing the aforesaid polynucleotide therein.

When the cells wherein a recombinant expression vector comprising the polynucleotide encoding the polypeptide in accordance with the present invention are used, the lignan glycosidation reaction can be catalyzed within the cells. Thus, the lignan glycosides can be mass-produced at low costs by an environment-friendly production process. In addition, the present invention can provide inexpensive foodstuffs or industry products through the mass-production of lignan glycosides.

By using the cells in accordance with the present invention, the polypeptide which catalyzes the lignan glycosidation reaction can be provided at low costs under environment-friendly conditions.

As described above, the transformants or cells in accordance with the present invention work satisfactorily as far as at least the polynucleotide encoding the polypeptide in accordance with the present invention is introduced therein. In other words, it should be noted that transformants or cells formed by means other than the recombinant expression vector are also within the technical scope of the present invention.

As described above, the polypeptide in accordance with the present invention has the activity to glycosidate piperitol, in addition to the activity to glycosidate sesaminol and/or pinoresinol. Thus, utilization of the polypeptide should not be limited only to the glycosidation of sesaminol and/or pinoresinol to produce these glycosides.

That is, the object of the present invention is to provide the transformant or cell, in which the polynucleotide encoding the polypeptide in accordance with the present invention is introduced, and not only to provide the respective vector species specifically described herein and methods of introducing the same. It should thus be noted that transformants or cells acquired using vector species and cell species other than those described above as well as other methods of preparing vectors or introducing cells are also within the technical scope of the present invention.

(C) Method of Producing Polypeptide

The present invention provides the method of producing the polypeptide in accordance with the present invention. By using the method of producing the polypeptide in accordance with the present invention, the polypeptide which catalyzes the lignan glycosidation reaction can be provided at low costs under environment-friendly conditions. Further by using the method of producing the polypeptide in accordance with the present invention, the polypeptide which catalyzes the lignan glycosidation reaction can be readily produced.

In an embodiment, the method of producing the polypeptide in accordance with the present invention comprises using the vector comprising the polynucleotide encoding the polypeptide in accordance with the present invention.

In one aspect of this embodiment, it is preferred to use the vector described above in a cell-free protein synthesis system for the method of producing the polypeptide in accordance with the embodiment. Where the cell-free protein synthesis system is used, various commercially available kits may be employed. Preferably, the method of producing the polypeptide in accordance with the embodiment comprises the step of incubating the vector described above and a cell-free protein synthesis solution.

In another aspect of the embodiment, it is preferred to use a recombinant expression system in the method of producing the polypeptide in accordance with this embodiment. Where the recombinant expression system is used, there may be adopted a method in which the polynucleotide in accordance with the present invention is incorporated into a recombinant expression vector, the vector is then expressibly introduced into a host by known methods, and the polypeptide described above is purified; and so on. The recombinant expression vector may be or may not be a plasmid, so long as the objective polynucleotide can be introduced into the host. Preferably, the method of producing the polypeptide in accordance with this embodiment includes the step of introducing the vector described above into a host.

Where an exogenous polynucleotide is introduced into a host as described above, preferably the expression vector has a promoter having incorporated therein to function in a host so as to express the exogenous polynucleotide. Though methods for purification of the polypeptide recombinantly produced are different depending upon host used and property of the polypeptide, the target polypeptide can be purified relatively easily by using a tag, etc.

Preferably, the method of producing the polypeptide in accordance with this embodiment further comprises the step of purifying the aforesaid polypeptide from the extract of cells or tissues having the polypeptide in accordance with the present invention. The step of purifying the polypeptide preferably comprises, but is not limited to, preparing a cell extract from cells or tissues by well-known methods (e.g., a method which comprises disrupting cells or tissues, centrifuging and recovering soluble fractions), followed by purifying the polypeptide from the cell extract by well-known methods (e.g., ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography). Most preferably, high performance liquid chromatography ("HPLC") is employed for purification.

In yet another embodiment, the method of producing the polypeptide in accordance with the present invention is characterized by purifying the said polypeptide from cells or tissues naturally expressing the polypeptide in accordance with present invention. Preferably, the method of producing the polypeptide in accordance with this embodiment comprises the step of identifying the cells or tissues naturally expressing the polypeptide in accordance with the present invention using the antibody or oligonucleotide described above. More preferably, the method of producing the polypeptide in accordance with this embodiment further comprises the aforesaid step of purifying the polypeptide.

In yet further embodiment, the method of producing the polypeptide in accordance with the present invention is characterized by chemically synthesizing the polypeptide in accordance with the present invention. One skilled in the art can readily understand that the polypeptide in accordance with the present invention can be chemically synthesized by applying well-known chemical synthesis technology to the amino acid sequence of the polypeptide in accordance with the present invention as described herein.

As described above, the polypeptide acquired by the method of producing the polypeptide in accordance with the present invention may be a naturally occurring variant polypeptide or an artificially produced variant polypeptide.

Methods of producing the variant polypeptide are not particularly limited. The variant polypeptide can be produced by well known methods of producing variant polypeptides, for example, site-specific mutagenesis (see, e.g., Hashimoto-Gotoh, Gene, 152, 271-275 (1995)), a method of producing variant polypeptides which involves introducing point mutations into base sequences using PCR, a method of producing mutants by transposon insertion, etc. Commercially available kits may also be utilized to produce the variant polypeptide.

As described above, the polypeptide in accordance with the present invention may be produced by known conventional techniques, at least, based on the amino acid sequence of the polypeptide having the lignan glycosidation activity, or the base sequence of the polynucleotide encoding the polypeptide having the lignan glycosidation activity.

In other words, the object of the present invention is to provide the method of producing the polypeptide having the lignan glycosidation activity. It should be noted that production methods further comprising steps other than the various steps described above are also within the technical scope of the present invention.

(D) Method of Producing Lignan Glycoside

To date, the production of lignans and lignan glycosides has been relied on extraction from sesame and hence, and thus involves difficulties in mass production, etc. According to the present invention, lignans and lignan glycosides can be mass-produced at low costs.

The present invention provides the method of producing lignan glycosides using organisms or cells capable of expressing the polypeptide in accordance with the present invention. The organisms described above may be naturally occurring intact organisms or transformants acquired using the recombinant expression system. According to the method of producing lignan glycosides, lignans (especially, pinoresinol, sesaminol or piperitol) can be produced efficiently.

In an embodiment, the method of producing lignan glycosides in accordance with the present invention comprises producing lignan glycosides using the organism transformed with the polynucleotide encoding the polypeptide in accordance with the present invention or its tissues. Preferably, the organism described above includes the transgenic plants or cells described above, especially preferably, *Escherichia coli*, sesame, *Forsythia intermedia* or *Linum usitatissimum*.

In a preferred aspect of this embodiment, the method of producing lignan glycosides in accordance with the present invention comprises the step of introducing the polynucleotide encoding the polypeptide in accordance with the present invention into the organism described above. For the step of introducing the polynucleotide into the organism described above, the various gene transfer methods described above may be used. In this aspect of the embodiment, the organism described above has different compositions between the lignan glycosides produced before transformation and those produced after transformation. Specifically, the lignans and lignan glycosides obtained from the organism described above provide an increased content of lignans and lignan glycosides. The method of producing lignan glycosides from this aspect of the embodiment preferably further comprises the step of extracting lignan glycosides from the organism described above.

In another embodiment, the method of producing lignan glycosides in accordance with the present invention comprises the step of introducing the oligonucleotide in accordance with the present invention as an antisense oligonucleotide into an organism which naturally expresses the polypeptide in accordance with the present invention. For the step of introducing the oligonucleotide into the organism described above, the antisense RNA technique described above may be used. Preferably, the method of producing lignan glycosides in accordance with this embodiment further comprises the step of using the antibody or oligonucleotide described above to identify an organism capable of naturally expressing the polypeptide in accordance with the present invention. The method of producing lignan glycosides in accordance with this aspect of the present embodiment further comprises the step of extracting lignan glycosides from the organism described above.

In this embodiment, the organism described above has different compositions between the lignan glycosides produced before introduction of the oligonucleotide described above and those produced after the introduction. Specifically, the lignans and lignan glycosides obtained from the organism described above provide a decreased content of lignans and their glycosides.

As described above, the method of producing lignan glycosides in accordance with the present invention comprises at least using the organism capable of expressing the polypeptide in accordance with the present invention.

In other words, the object of the present invention is to provide the method of producing lignan glycosides based on the organism wherein the composition of lignan glycosides is altered by the polypeptide in accordance with the present invention. It should be noted that production methods using animals, plants or various cells as the organism described above are also within the technical scope of the present invention.

(E) Foodstuff and Industrial Product

The present invention provides foodstuffs and industrial products using the lignan glycosides, which are obtained by the method of producing lignan glycosides described above. The foodstuffs referred to in this section may be any of seeds, fruits, cut panicles, tubers and/or tuberous roots, etc. of the transgenic plants described above, or may be foodstuffs (e.g., sesame, *Forsythia intermedia* or *Linum usitatissimum*, or processed foodstuffs) manufactured using the lignan glycosides extracted from the transgenic plant described above. The foodstuffs or industrial products in accordance with the present invention may contain a desired amount of lignans (especially, pinoresinol, sesaminol or piperitol).

For example, the extract solutions of lignan glycosides extracted from the transgenic plant in accordance with the present invention, in which the content of lignan glycosides is increased as described above, can be provided as lignan glycoside-rich foodstuffs. In addition to the extracted lignan glycosides, the seeds, fruits, cut panicles, tubers and/or tuberous roots, etc. of the transgenic plants described above can also be provided as lignan glycoside-rich foodstuffs. The target for alteration of the lignan glycoside composition is not particularly limited but, in addition to plants, all organisms including animals, bacteria, yeasts, etc. may be targeted.

Based on the unique physical properties of lignans and lignan glycosides, the polypeptide or polynucleotide in accordance with the present invention are also available as raw materials for industrial products (e.g., industrial products such as films, biodegradable plastics, functional fibers, lubricants or detergents).

In the specification, the polypeptide for lignan glycosidation of sesame is illustratively given as an example but it is obvious to one skilled in the art that the present invention should not be limited to the sesame-derived polypeptide or polynucleotide and relates to all polypeptides having the lignan glycosidation activity and their utilization. Lignan glycosidases may be derived from any one of plants, animals or microorganisms and can regulate the lignan content, so long as they possess the lignan glycosidation activity. The present invention further relates to a plant prepared by introducing the polynucleotide encoding the lignan glycosidase, its progeny, of tissues thereof, in which the lignan content is controlled. The form of plant may be a cut flower. By using the polypeptide for lignan glycosidation in accordance with the present invention, the production of lignan glycosides can be promoted or suppressed. One skilled in the art can readily understand that by using conventional procedures, it is possible to introduce the polynucleotide described above into plants and express the polynucleotide in a constitutive or tissue-specific manner, thereby increasing the expression of the target polypeptide, while it is also possible to repress the expression of the target polypeptide, using the antisense method, the cosuppression method, the RNAi method, etc.

The present invention will be described in more detail by referring to the following EXAMPLES but is not deemed to be limited thereto.

EXAMPLES

Molecular biological strategies used in EXAMPLES were implemented in accordance with the method described in PCT/JP03/10500 (Title of the Invention: Transferase Gene) or Molecular Cloning (Sambrook et al., Cold Spring Harbour Laboratory Press, 1989), unless otherwise indicated.

Example 1

Construction of Sesame cDNA Library

Total RNA was extracted from sesame seeds using RNeasy Plant Mini Kit (QIAGEN) according to the protocol recommended by the manufacturer. Subsequently, Oligotex-MAG mRNA Purification Kit (TaKaRa) was used to obtain 5 µg of poly A(+) RNA. A cDNA library was prepared from the poly A(+) RNA using ZAP Express cDNA Synthesis Kit and ZAP Express cDNA Gigapack 3 Gold Cloning Kit (Stratagene), according to the protocol recommended by the manufacturer. The library prepared was 1×10$^7$ pfu/ml.

Example 2

Production of Hybridization Probes

Plants have various glycosyltransferases depending on kinds of substrates and sugars to be transferred. Many of these glycosyltransferases belong to one family type. The glycosyltransferases belonging to this type contain the consensus sequence:
[F/V/A]-[L/I/V/M/F]-[T/S]-[H/Q]-[S/G/A/C]-GXX-[S/T/G]-XX-[D/E]-XXXXXXP-[L/I/V/M/F/A]-XX-P-[L/M/V/F/I/Q]-XX-[D/E]-Q at the C terminus (see, e.g., Pharmacogenetics, 7255 (1997)).

The consensus sequences in glycosyltransferase genes (GT) derived from 5 different plant species were obtained by PCR amplification. Specifically, the consensus sequences of UDP glucose: anthocyanidin 3-glucoside glycosyltransferase (3GGT) derived from morning glory, 3GT derived from petunia, 5GT derived from verbena, *Scutellaria baicalensis* GT, and UDP-glucose: anthocyanin 3'-glycosyltransferase (3'GT) derived from gentian were obtained by RT-PCR as described below, using the following 5 pairs of primers (SEQ ID NO: 11 to SEQ ID NO: 20).

```
(Morning glory 3GGT)
5'-gaaatggtcggattggctggg-3'         (SEQ ID NO: 11)

5'-acctccaccccaactttcagg-3'         (SEQ ID NO: 12)

(Petunia 3GT)
5'-gatgcataatttggctagaaaagc-3'      (SEQ ID NO: 13)

5'-ccaatttgccaaacactttcc-3'         (SEQ ID NO: 14)

(Verbena 5GT)
5'-tgcctcgaatggttgagcacg-3'         (SEQ ID NO: 15)

5'-ctctcactctcacacccg-3'            (SEQ ID NO: 16)

(Scutellaria baicalensis GT)
5'-cacgaatgcttagcatggctc-3'         (SEQ ID NO: 17)
```

```
-continued
5'-cttattgcccactgaaacccc-3'         (SEQ ID NO: 18)

(Gentian 3'GT)
5'-tgtctgaattggcttgattcc-3'         (SEQ ID NO: 19)

5'-aacccacagaaacccctgttc-3'.        (SEQ ID NO: 20)
```

Total RNA was extracted from the various plants described above using RNeasy Plant Mini Kit (QIAGEN). Then, SuperScript™ First-Strand Synthesis System for RT-PCR (Invitrogen) was used according to the protocol recommended by the manufacturer to produce cDNA from 1 µg of the total RNA. A PCR reaction solution (50 µl) was composed of 1 µl of each cDNA, 1× Taq buffer (TaKaRa), 0.2 mM dNTPs, 0.4 pmol/µl each of primers (SEQ ID NO: 11 through SEQ ID NO: 20) and 2.5 U of rTaq polymerase. PCR was carried out as follows: after reacting at 94° C. for 5 minutes, by 28 cycles of the reaction at 94° C. for 1 minute, 53° C. for 1 minute and 72° C. for 2 minutes.

Using non-radioisotope DIG Nucleic Acid Detection System (Roche) according to the protocol recommended by the manufacturer, DIG label was introduced into the fragment obtained by RT-PCR. This DIG-labeled fragment was used as a probe for hybridization in the following experiment.

Example 3

Screening of Sesame-Derived Glycosyltransferase Family

Using non-radioisotope DIG Nucleic Acid Detection System (Roche Diagnostics) according to the protocol recommended by the manufacturer, the cDNA library obtained in EXAMPLE 1 was screened with the probe obtained in EXAMPLE 2.

After hybridization was effected at 37° C. for 2 hours in a buffer solution for hybridization (5×SSC, 30% formamide, 50 mM sodium phosphate buffer (pH 7.0), 1% SDS, 2% blocking reagent (Roche), 0.1% lauroylsarcosine), the probe obtained in EXAMPLE 2 was added to further continue the incubation overnight. Membrane was washed at 55° C. for 30 minutes in 5×SSC wash solution containing 1% SDS. Approximately 3×10$^5$ pfu of plaques were screened to obtain about 500 positive clones.

Using a cDNA library synthesis kit according to the protocol recommended by the manufacturer, the 500 clones described above were inserted into pBK-CMV plasmid (Stratagene). A partial DNA sequence of the insert was determined using a primer pair of M13RV and M13M4 (–20). Using the putative amino acid sequence deduced based on the determined DNA sequence, database search was made to determine the partial sequences of 18 sesame-derived glycosyltransferase (SiGT) genes. The primer walking method using synthetic oligonucleotide primer was performed with DNA Sequencer model 3100 (Applied Biosystems) to determine the base sequences of 18 cDNAs.

The determined partial sequences of SiGT genes were analyzed by Blastx (http://www.ncbi.nlm.nih.gov/BLAST/) to confirm that the partial sequences were homologous to the glycosyltransferases. The conditions of Blastx analysis were as follows.

Program: Blastx ver. 2.2.9, database: nr, genetic code: standard (1), filter: LOW complexity, Expect: 10, Word size: 3, matrix: BLOSUM 62, Gap Costs: Existence 11, Extension 1.

Example 4

Expression Analysis of Sesame-Derived Glycosyltransferase Family

In order to confirm in which organ and when the respective SiGTs obtained was expressed, reverse transcription-PCR (RT-PCR) was conducted using primers designed on the basis of the partial sequences of SiGTs obtained.

Total RNA was extracted from each organ of sesame plants (leaf, stem, hull, seed) (growth stages 1 to 4 in the order of youngest to oldest) and germinated seeds (FIG. 1A)) using RNeasy Plant Mini Kit (QIAGEN). SuperScript™ First-Strand Synthesis System for RT-PCR (GIBCO BRL) was used according to the protocol recommended by the manufacturer to produce cDNA from 1 µg of the total RNA. A PCR reaction solution (25 µl) was composed of 1 µl of cDNA, 1× Ex-Taq buffer (TaKaRa), 0.2 mM dNTPs, 0.2 µmol/µl each of primers and 1.25 U of Ex-Taq polymerase. After reacting at 94° C. for 5 minutes, the reaction at 94° C. for 1 minute, 55° C. for 1 minute and 72° C. for 2 minutes was carried 30 cycles for PCR amplification, followed by maintaining at 72° C. for 7 minutes. In order to compare the expression level of SiGT gene to the expression level of endogenous gene, PCR was simultaneously performed for a gene as an internal standard. Specifically, PCR was performed for sesame 18S ribosomal RNA gene (Accession No.: AF169853) using Si18SrRNA-F primer (SEQ ID NO: 57) and Si18SrRNA-R primer (SEQ ID NO: 58). Also, PCR was simultaneously performed for a gene as positive control for PCR. Specifically, PCR was performed for sesamin synthase gene SiP189 using SiP189-Bam-FW primer (SEQ ID NO: 59) and SiP189-Xho-RV primer (SEQ ID NO: 60).

The following primers were used for amplification of SiGT (SEQ ID NO: 21 through SEQ ID NO: 56).

```
SiGT1-FW:
                                         (SEQ ID NO: 21)
5'-tagatgaatttgtcggaaaga-3'

SiGT1-RV:
                                         (SEQ ID NO: 22)
5'-tataatgttacaaaatcaact-3'

SiGT2-FW2:
                                         (SEQ ID NO: 23)
5'-ggcagagttttctatgggttgt-3'

SiGT2-RV:
                                         (SEQ ID NO: 24)
5'-atagcagtgggctagaaaga-3'

SiGT3-FW:
                                         (SEQ ID NO: 25)
5'-cctgtaactagaatggcgtcaat-3'

SiGT3-RV:
                                         (SEQ ID NO: 26)
5'-tttgacaaaaccaaaaccacactt-3'

SiGT4-FW2:
                                         (SEQ ID NO: 27)
5'-tttagctcgttttctcctctcatt-3'

SiGT4-RV:
                                         (SEQ ID NO: 28)
5'-ctacatgttattacatctacagaa-3'

SiGT5-FW2:
                                         (SEQ ID NO: 29)
5'-catctcaatccataatgcaga-3'

SiGT5-RV:
                                         (SEQ ID NO: 30)
5'-aacaagaactcacttgaagataat-3'

SiGT6-FW:
                                         (SEQ ID NO: 31)
5'-gccattgacaggtatgagtta-3'

SiGT6-RV:
                                         (SEQ ID NO: 32)
5'-gatctaatgtttacatagtatcct-3'

SiGT7-FW2:
                                         (SEQ ID NO: 33)
5'-catcacccacttcatttccaa-3'

SiGT7-RV:
                                         (SEQ ID NO: 34)
5'-attattattattttttcaataatta-3'

SiGT8-FW2:
                                         (SEQ ID NO: 35)
5'-tttatcctgtggggccaatactt-3'

SiGT8-RV:
                                         (SEQ ID NO: 36)
5'-tcttgccattcacattcagattga-3'

SiGT9-FW2:
                                         (SEQ ID NO: 37)
5'-acaactaagcataagtcacttaaa-3'

SiGT9-RV:
                                         (SEQ ID NO: 38)
5'-gccttcttcgcttggtcagat-3'

SiGT10-FW2:
                                         (SEQ ID NO: 39)
5'-gaagccgccaggtatttgctt-3'

SiGT10-RV:
                                         (SEQ ID NO: 40)
5'-acaagataaaacataatccta-3'

SiGT11-FW2:
                                         (SEQ ID NO: 41)
5'-tttccagctcaaggccatattaat-3'

SiGT11-RV:
                                         (SEQ ID NO: 42)
5'-tacaaacgacacagagaaatagga-3'

SiGT12-FW2:
                                         (SEQ ID NO: 43)
5'-aagtacaagtggatggatata-3'

SiGT12-RV:
                                         (SEQ ID NO: 44)
5'-acggcttattccaactatctaaca-3'

SiGT13-FW2:
                                         (SEQ ID NO: 45)
5'-aggttttgagaactggagttt-3'

SiGT13-RV:
                                         (SEQ ID NO: 46)
5'-taataaagctggaaacttcaccaa-3'

SiGT14-FW2:
                                         (SEQ ID NO: 47)
5'-ctagtggagctaggaaaactcat-3'

SiGT14-RV:
                                         (SEQ ID NO: 48)
5'-agattaagcacgtttccacaa-3'

SiGT15-FW:
                                         (SEQ ID NO: 49)
5'-tgatcaagttgccgtggtaat-3'
```

```
-continued
SiGT15-RV:
                                         (SEQ ID NO: 50)
5'-aacgtacaagaagtatatatt-3'

SiGT16-FW2:
                                         (SEQ ID NO: 51)
5'-tttcttccgatgatagctcat-3'

SiGT16-RV:
                                         (SEQ ID NO: 52)
5'-gtcaacttatctggaagatca-3'

SiGT17-FW2:
                                         (SEQ ID NO: 53)
5'-acgggaatcaggtcttgacat-3'

SiGT17-RV:
                                         (SEQ ID NO: 54)
5'-gatgattgatcaacagtgcatctt-3'

SiGT18-FW:
                                         (SEQ ID NO: 55)
5'-ccatcggaattaccatctgaa-3'

SiGT18-RV:
                                         (SEQ ID NO: 56)
5'-ataatcaaaggtctctgcaaa-3'

Si18SrRNA-FW:
                                         (SEQ ID NO: 57)
5'-tatgcttgtctcaaagattaa-3'

Si18SrRNA-RV:
                                         (SEQ ID NO: 58)
5'-aacatctaagggcatcacaga-3'

SiP189-Bam-FW:
                                         (SEQ ID NO: 59)
5'-ggatcctttcagccaacatggaagctgaa-3'

SiP189-Xho-RV:
                                         (SEQ ID NO: 60)
5'-ctcgagaaaaagagcatcatttaatcatacact-3'.
```

As a result of the gene expression analysis by RT-PCR described above, 5 SiGTs (SiGT1, SiGT3, SiGT5, SiGT8 and SiGT10) out of 18 SiGT genes showed strong expression in seeds and germinated seeds (FIG. 1B). These expression patterns are consistent with the accumulation patterns of lignan glycosides.

Example 5

Cloning of the Full-Length ORF in Sesame Glycosyltransferase Gene

In four SiGTs except SiGT3, the clones obtained by screening of the library lacked the 5' region of putative ORF. Thus, the 5' region of each SiGT gene was amplified by the 5' rapid amplification of cDNA end (hereinafter 5' RACE) method. Specifically, using Gene Racer Kit (Invitrogen) according to the protocol recommended by the manufacturer, the 5' region of each of SiGT1, SiGT5, SiGT8 and SiGT10 was amplified using the following primers (SEQ ID NO: 61 through SEQ ID NO: 68).

```
GR-SiGT1-RV:
                                         (SEQ ID NO: 61)
5'-gggaaatgcccattctctctcagaaggt-3'

GR-SiGT1-Nest-RV:
                                         (SEQ ID NO: 62)
5'-gtaagctagagtaaaaaccaa-3'
```

```
-continued
GR-SiGT5-RV:
                                         (SEQ ID NO: 63)
5'-gcccaggtgttcctgttcccaccactctct-3'

GR-SiGT5-Nest-RV:
                                         (SEQ ID NO: 64)
5'-aatctgcaggtattgtataaatct-3'

GR-SiGT8-RV:
                                         (SEQ ID NO: 65)
5'-ccacagcaatctccttcacctgatccccttcca-3'

GR-SiGT8-Nest-RV:
                                         (SEQ ID NO: 66)
5'-caaagcaaagaaacactacagaagaat-3'

GR-SiGT10-RV:
                                         (SEQ ID NO: 67)
5'-cctccgcttcccaacctcaaccgcccagta-3'

GR-SiGT10-Nest-RV:
                                         (SEQ ID NO: 68)
5'-acgtatcggcaattataaaattaa-3'.
```

The base sequences of the amplified fragments obtained by the 5' RACE method were determined by the primer walking method to obtain sequence information including the full-length open reading frame of each SiGT (SEQ ID NO: 1 to SEQ ID NO: 10). The base sequence and amino acid sequence of each SiGT are shown by SEQ ID NO: 1 and NO: 2 (SiGT8), SEQ ID NO: 3 and NO: 4 (SiGT10), SEQ ID NO: 5 and NO: 6 (SiGT1), SEQ ID NO: 7 and NO: 8 (SiGT3), as well as SEQ ID NO: 9 and NO: 10 (SiGT5).

The full-length cDNA sequences of SiGT genes obtained were analyzed by Blastx (http://www.ncbi.nlm.nih.gov/BLAST/) to search known proteins having homology. The conditions of Blastx analysis were as follows.

Program: Blastx ver. 2.2.9, database: nr, genetic code: standard (1), filter: LOW complexity, Expect: 10, Word size: 3, matrix: BLOSUM62, Gap Costs: Existence 11, Extension 1.

According to the results of Blastx analysis, SiGT1 showed 47% sequence dentity to *Arabidopsis thaliana* glycosidase (At2g36970), SiGT3 showed 54% sequence identity to *Arabidopsis thaliana* glycosidase (At2g36780), SiGT5 showed 50% sequence dentity to *Phaseolus vulgaris* glycosidase (AAM09516), SiGT8 showed 56% sequence dentity to tobacco glycosidase (BAB60720), and SiGT10 showed 49% sequence dentity to *Arabidopsis thaliana* glycosidase (At2g30150). As such, the sequence identity between SiGT and known glycosidases was low in all cases. It was thus unable to deduce the putative function of the SiGT gene family acquired. In other words, it is highly likely that the acquired SiGT gene family will be lignan glycosidases which have not been hitherto isolated.

Example 6

Construction of *Escherichia coli* Expression Vector

Using primer pairs of SEQ ID NO: 69 and NO: 70 for SiGT1, SEQ ID NO: 71 and NO: 72 for SiGT3, SEQ ID NO: 73 and NO: 74 for SiGT5, SEQ ID NO: 75 and NO: 76 for SiGT8, and SEQ ID NO: 77 and NO: 78 for SiGT10, fragments having the NcoI site upstream of the initiation methionine codon (ATG) and the KpnI site downstream of the termination codon of cDNA in each SiGT were amplified by PCR.

A PCR solution (25 µl) was composed of template cDNA from sesame seed, 0.2 pmol/µl of each primer, 1×KOD plus buffer (TOYOBO), 0.2 mM dNTPs, 1 mM MgSO$_4$, and 1 U KOD plus polymerase. After reacting at 94° C. for 5 minutes, the reaction at 94° C. for 1 minute, 55° C. for 1 minute and 72°

C. for 2 minutes was carried 30 cycles for PCR amplification, followed by maintaining at 72° C. for 3 minutes. Each of the PCR products obtained was inserted into a multicloning site of pCR4 Blunt-TOPO vector (Invitrogen) according to the protocol recommended by the manufacturer to obtain SiGT1/pCR4 Blunt-TOPO (referred to as pSPB2630), SiGT3/pCR4 Blunt-TOPO (referred to as pSPB2643), SiGT5/pCR4 Blunt-TOPO (referred to as pSPB2644), SiGT8/pCR4 Blunt-TOPO (referred to as pSPB2631), and SiGT10/pCR4 Blunt-TOPO (referred to as pSPB2633). The primers used for PCR are shown below (SEQ ID NO: 69 to NO: 78).

```
NcoI-SiGT1-FW2:
                                      (SEQ ID NO: 69)
5'-aaacagcaaacagaaaccatggccgagtgt-3'

BglKpnI-SiGT1-RV:
                                      (SEQ ID NO: 70)
5'-tttggtaccagatcttttgcagctagtcaactattatttaacttg
tagt-3'

NcoI-SiGT3-FW:
                                      (SEQ ID NO: 71)
5'-aaaaccatggcgtcaatggccatccaagaacaa-3'

KpnIBgl-SiGT3-RV:
                                      (SEQ ID NO: 72)
5'-aaaagatctggtacctcagtggaccatgacaacatcagaattttca
t-3'

NcoI-SiGT5-FW:
                                      (SEQ ID NO: 73)
5'-aaaaccatgggcagcttgagcaatcaacaga-3'

KpnI-SiGT5-RV:
                                      (SEQ ID NO: 74)
5'-aaaggtaccctatcttattatatgggcaacaaaggaat-3'

NcoI-SiGT8-FW:
                                      (SEQ ID NO: 75)
5'-aaaaccatggcggcggaccaaaaattaa-3'

KpnI-SiGT8-RV:
                                      (SEQ ID NO: 76)
5'-aaaggtacctcaagaaatgttattcacgacatt-3'

NcoI-SiGT10-FW:
                                      (SEQ ID NO: 77)
5'-aaaaccatggcgccggcggcgagaaccgacccaatcat-3'

KpnI-SiGT10-RV:
                                      (SEQ ID NO: 78)
5'-tttggtacctcagctaaacgatgcaatatcatcgaggaa-3'.
```

The SiGT base sequences contained in pSPB2630, pSPB2643, pSPB2644, pSPB2631 and pSPB2633 were analyzed to confirm that PCR was correctly performed. These plasmids were digested with NcoI and KpnI to acquire about 1.5 kb of DNA fragment containing the full-length SiGT. The fragment was inserted into the NcoI/KpnI site of *Escherichia coli* expression vector, i.e., pQE61 vector (QIAGEN) to obtain SiGT1/pQE61 (referred to as pSPB2637), SiGT3/pQE61 (referred to as pSPB2642), SiGT5/pQE61 (referred to as pSPB2645), SiGT8/pQE61 (referred to as pSPB2639), and SiGT10/pQE61 (referred to as pSPB2640).

Example 7

Preparation of Recombinant Protein

*Escherichia coli* JM109 (TOYOBO) was transformed with *Escherichia coli* expression vectors pSPB2637, pSPB2642, pSPB2645, pSPB2639 and pSPB2640 prepared in EXAMPLE 6, and preincubated at 37° C. overnight in LB medium supplemented with ampicillin in final concentration of 20 µg/ml. A part of the preincubation culture was added to M9 medium (10 ml) containing 50 µg/ml of ampicillin and 0.5% Casamino acid, and shake cultured to reach $A_{600}$=0.6-1.0. The composition of M9 medium is as follows: 1×M9 salt, 1 mM $MgSO_4$, 0.2% glucose and 0.001% thiamine hydrochloride. The composition of 10×M9 medium is as follows: a 500 ml aqueous solution containing 30 g of $Na_2HPO_4$, 15 g of $KH_2PO_4$, 2.5 g of NaCl and 5 g of $NH_4Cl$. Next, IPTG (isopropyl-β-D-thiogalactopyranoside) in a final concentration of 0.5 mM was added to the culture. After further shake culture at 30° C. overnight, centrifugation was performed at 3000 rpm at 4° C. for 10 minutes to collect the cells. After the cells were suspended in 10 ml of buffer (30 mM Tris-HCl (pH 7.5), 30 mM NaCl), the suspension was ultrasonicated to disrupt *Escherichia coli* and then centrifuged at 15,000 rpm at 4° C. for 10 minutes. The supernatant obtained was used as a crude enzyme solution for the following activity assay.

Example 8

HPLC Analysis of the Product by Sesame Lignan Glycosidase

Pinoresinol, piperitol or sesaminol was dissolved in a small quantity of DMSO and further dissolved in 70% ethanol to prepare a substrate solution (1 mg/ml). After 10 µl of this substrate solution, 200 µl of the aforesaid crude enzyme solution of the 5 SiGTs expressed in *Escherichia coli* and 2.5 µl of 20 mM UDP-glucose were mixed in a reaction tube, the mixture was reacted at 30° C. for an hour. Pinoresinol, piperitol and sesaminol can be obtained, for example, by extracting and purifying from sesame in accordance with publicly known methods (J. Bioscience, Biotechnology and Biochemistry, 67: 1693 (1993)).

The enzyme reaction was terminated by adding 100% acetonitrile (250 µl) containing 0.1% TFA (trifluoroacetic acid) to the reaction tube. The reaction tube was vigorously agitated with a vortex mixer, followed by centrifugation at 15,000 rpm at 4° C. for 5 minutes. The resulting supernatant was washed through a filter (pore size of 0.45 mm, 4 mm Millex-LH, Millipore) and then analyzed using high performance liquid chromatography (hereinafter HPLC). The conditions for analysis of lignans and their glycosides are as follows.

Liquid chromatography (Lc-2010c (Shimadzu Corporation)) was performed using a C-30 column (Nomura Chemical, C30-UG-5, 4.6 mm×150 mm). In the mobile phase, 0.1% TFA and 0.1% TFA-containing 90% acetonitrile were used as eluent A and eluent B, respectively. The column was equilibrated with a mixture of 60% eluent A and 40% eluent B (20 minutes), and eluted with a linear gradient (60% eluent A: 35% eluent B 10% eluent A: 90% eluent B) for 15 minutes (flow rate of 0.6 ml/min.) and then with 10% eluent A: 90% eluent B for 10 minutes. Absorption was monitored at 287 nm to detect the compound contained in a sample. The spectra between 190 nm and 400 nm for each peak of the compound were measured using SPD-10AV (Shimadzu Corporation) to detect a substance having two absorption maxima (230 nm and 280 nm) characteristic of lignans. Under the conditions, authentic pinoresinol is detected at about 8.4 minutes, authentic piperitol at about 12.8 minutes and authentic sesaminol at about 13.8 minutes (FIGS. 2 and 3).

Figure 2A:
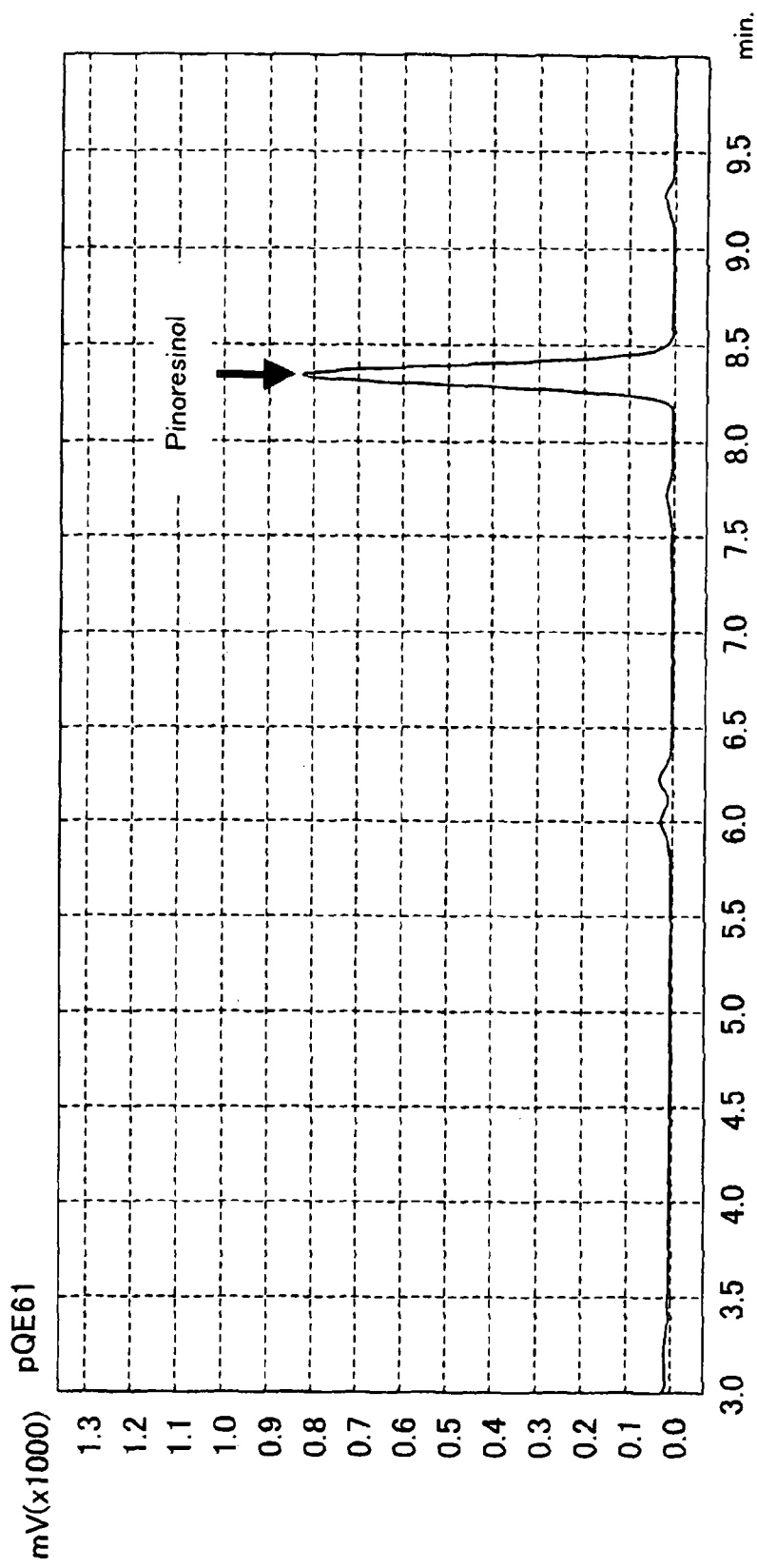
FIG. 2A is a graph showing the pinoresinol glycosidation activity in a cell to which an empty vector alone for producing the SiGT recombinant protein is introduced.
Figure 2B:
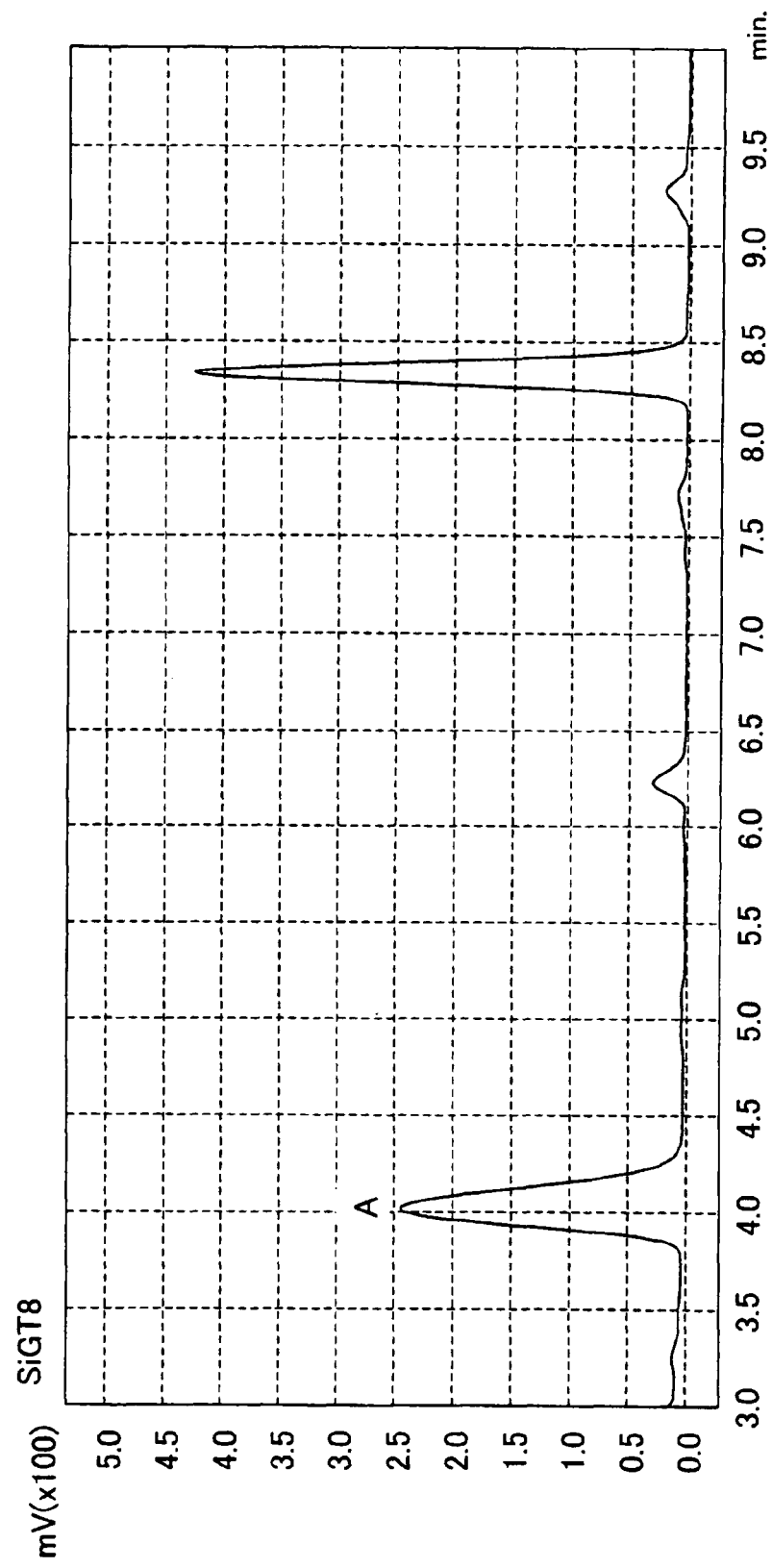
FIG. 2B is a graph showing the pinoresinol glycosidation activity of SiGT protein (SiGT8).

In the reaction solution of SiGT8 recombinant protein and pinoresinol, peak A having the spectrum of lignan (retention time of about 4.0 minutes) was newly obtained (FIG. 2B).

Figure 2C:
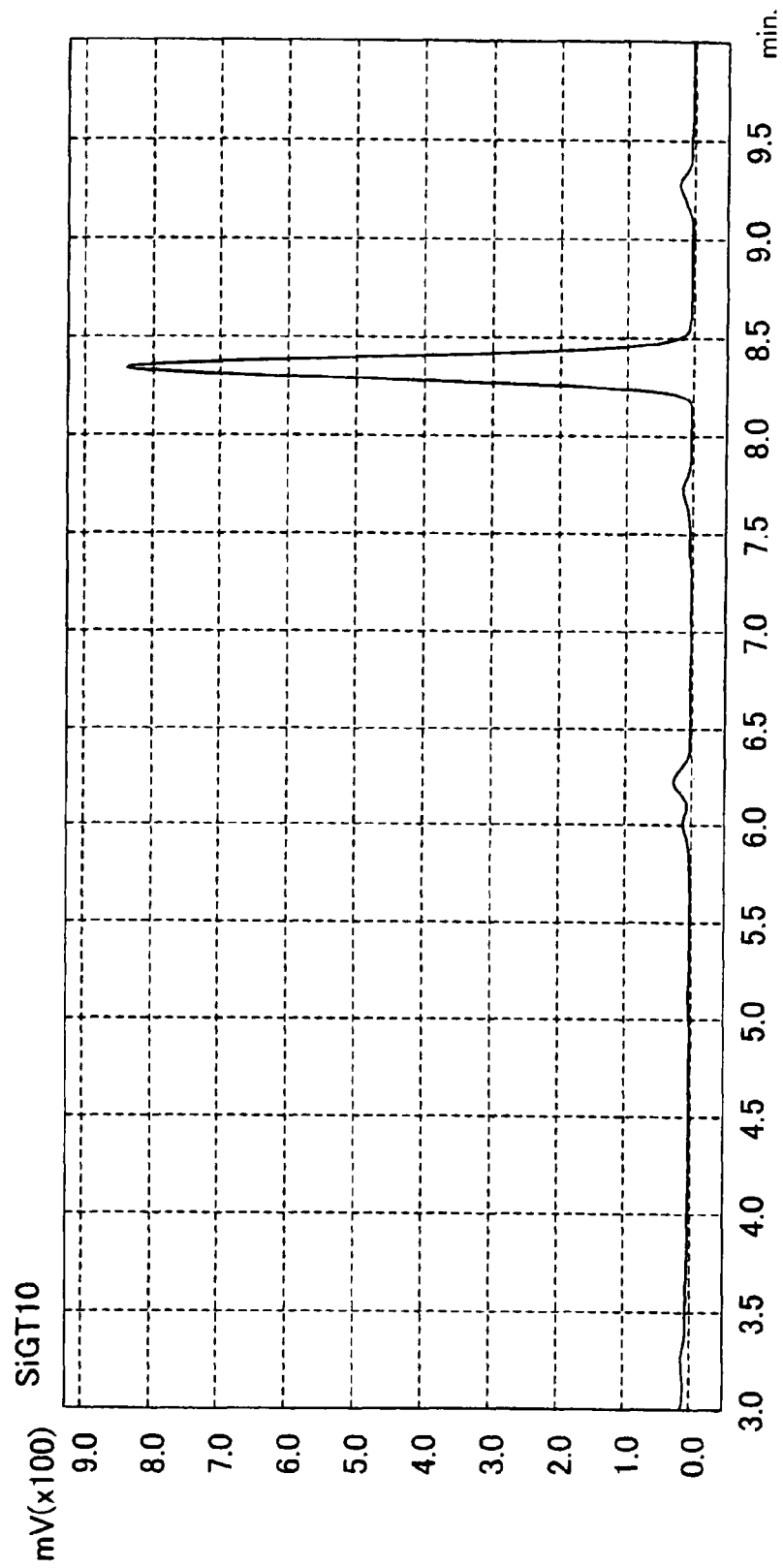
FIG. 2C is a graph showing the pinoresinol glycosidation activity of SiGT protein (SiGT10).
Figure 2D:
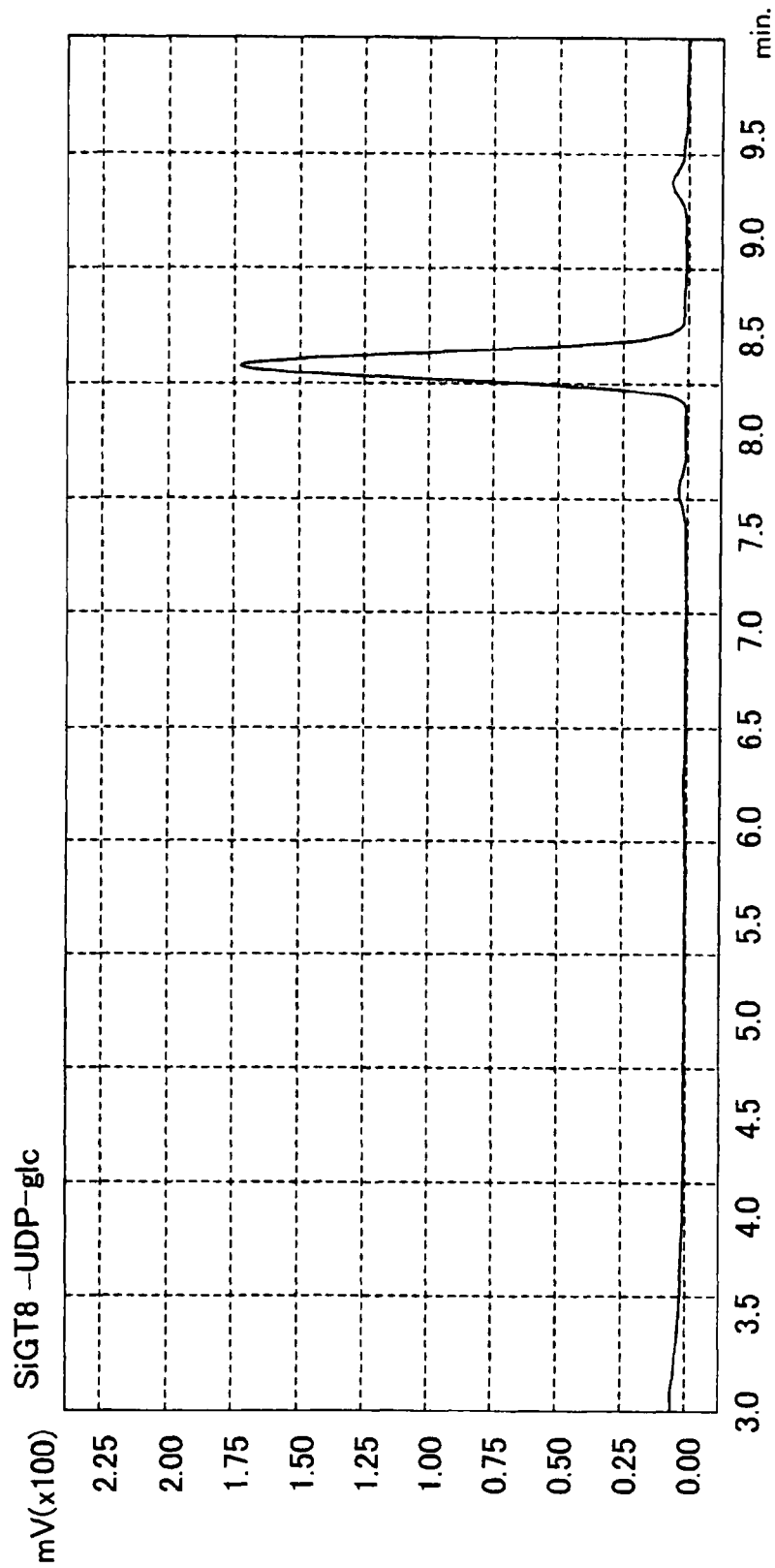
FIG. 2D is a graph showing the pinoresinol glycosidation activity of SiGT protein (SiGT8) where UDP-glucose is removed from the enzyme reaction solution.
Figure 2E:
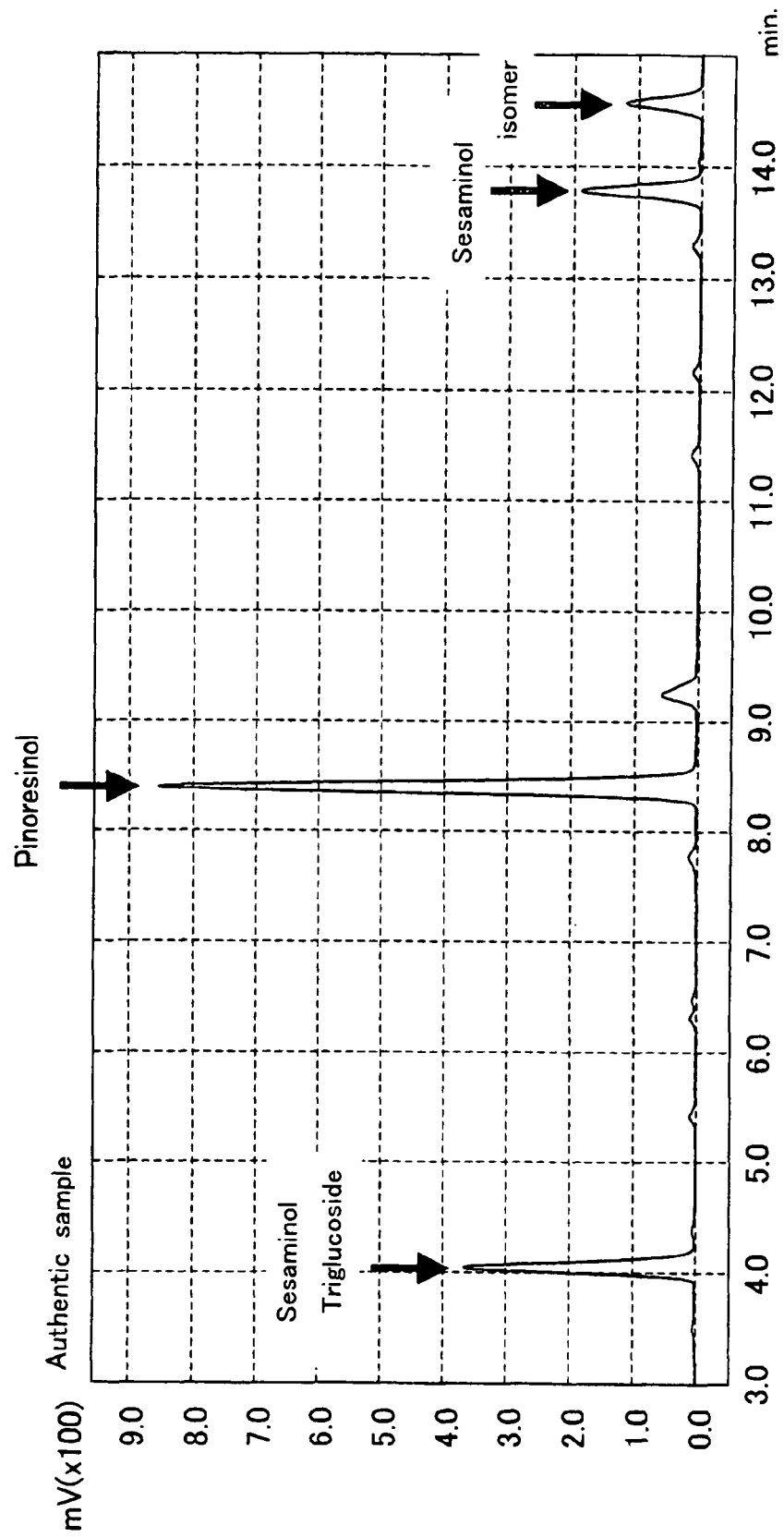
FIG. 2E is a graph showing the peaks of various authentic lignans.
Figure 2F:
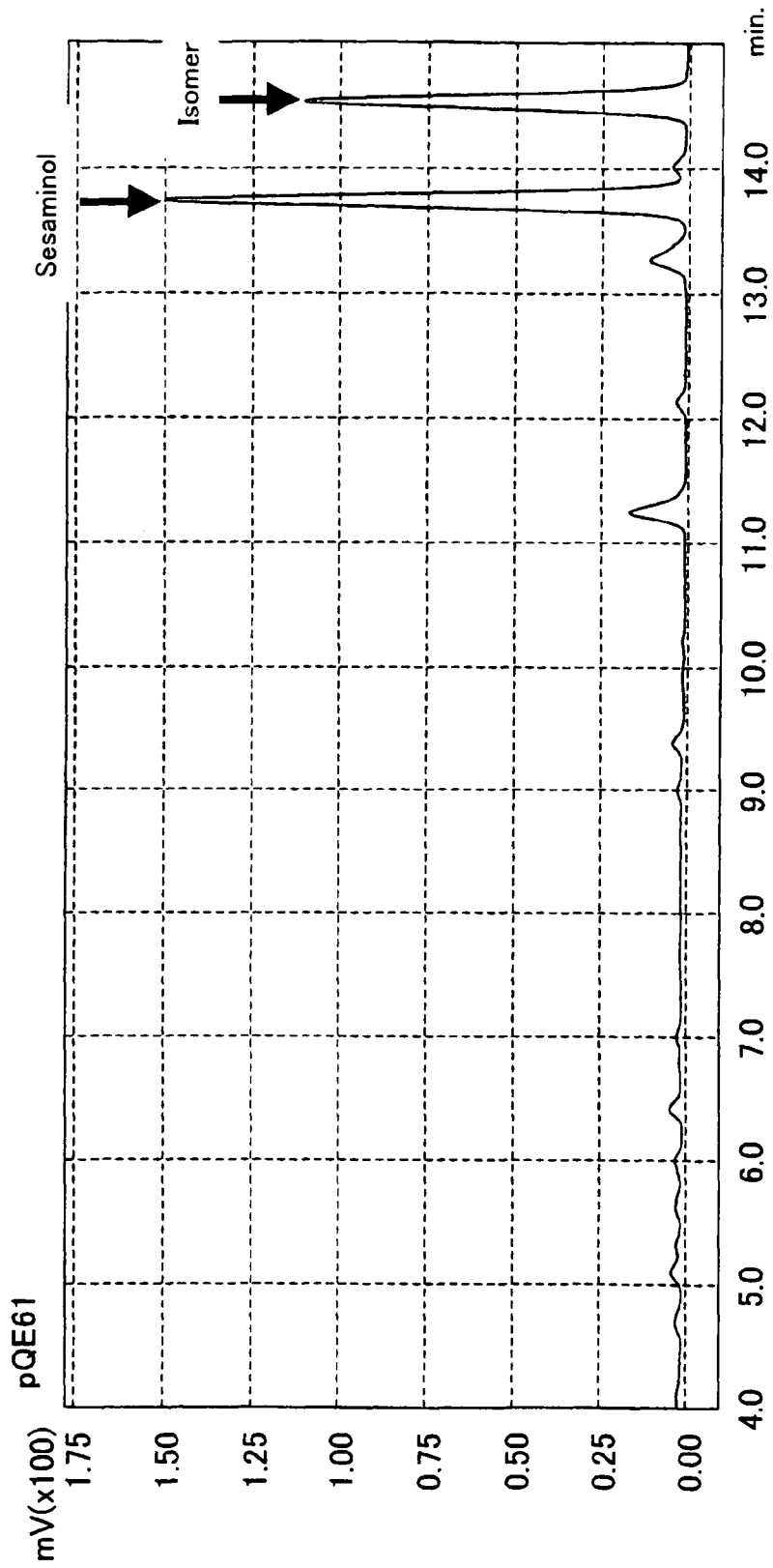
FIG. 2F is a graph showing the sesaminol glycosidation activity in a cell to which an empty vector alone for producing the SiGT recombinant protein is introduced.
Figure 2G:
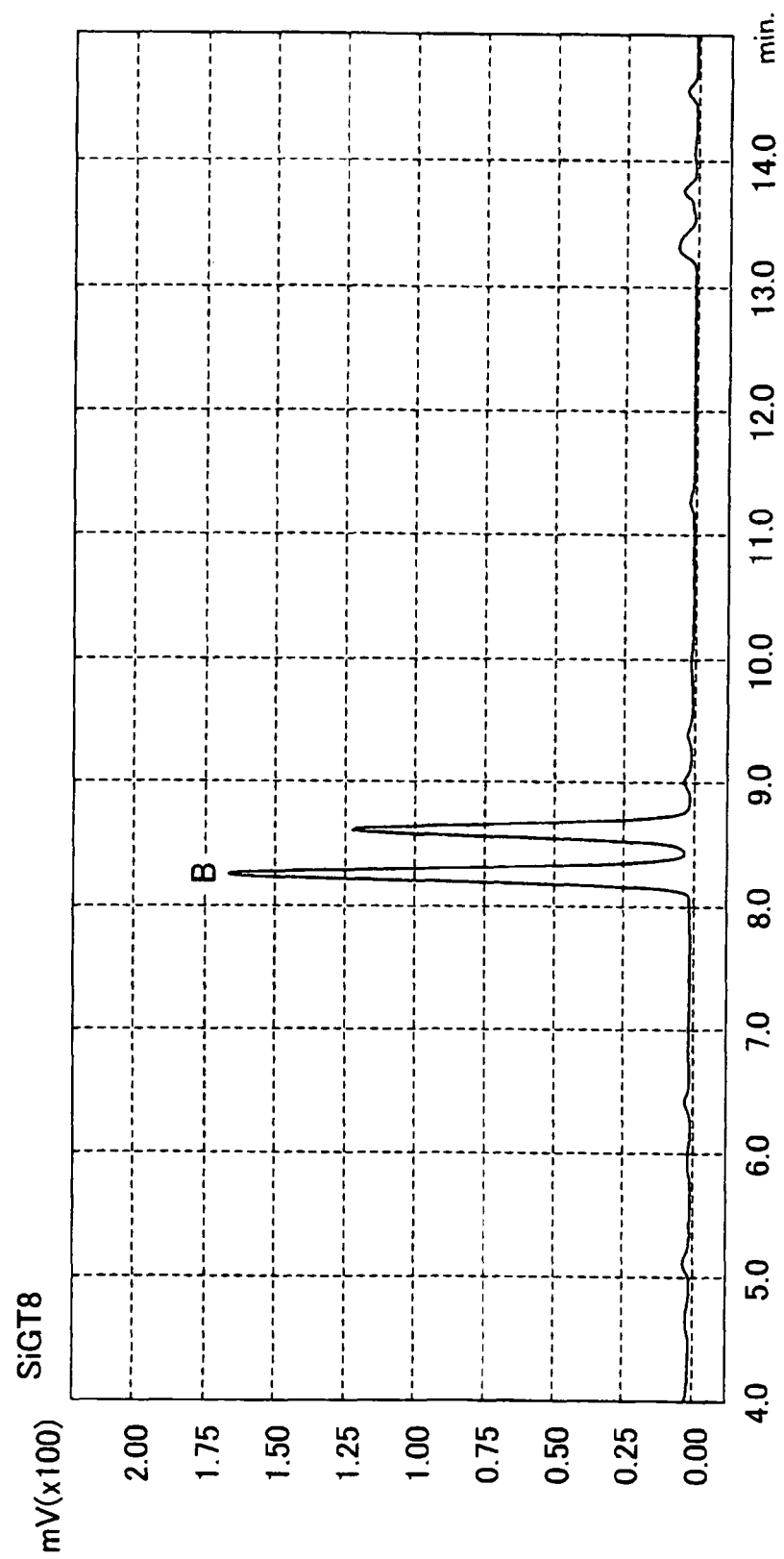
FIG. 2G is a graph showing the sesaminol glycosidation activity of SiGT protein (SiGT8).

Further in the reaction solution of SiGT8 recombinant protein and sesaminol, peak B having the spectrum of lignan (retention time of about 8.2 minutes) was newly obtained (FIG. 2G).

Figure 2H:
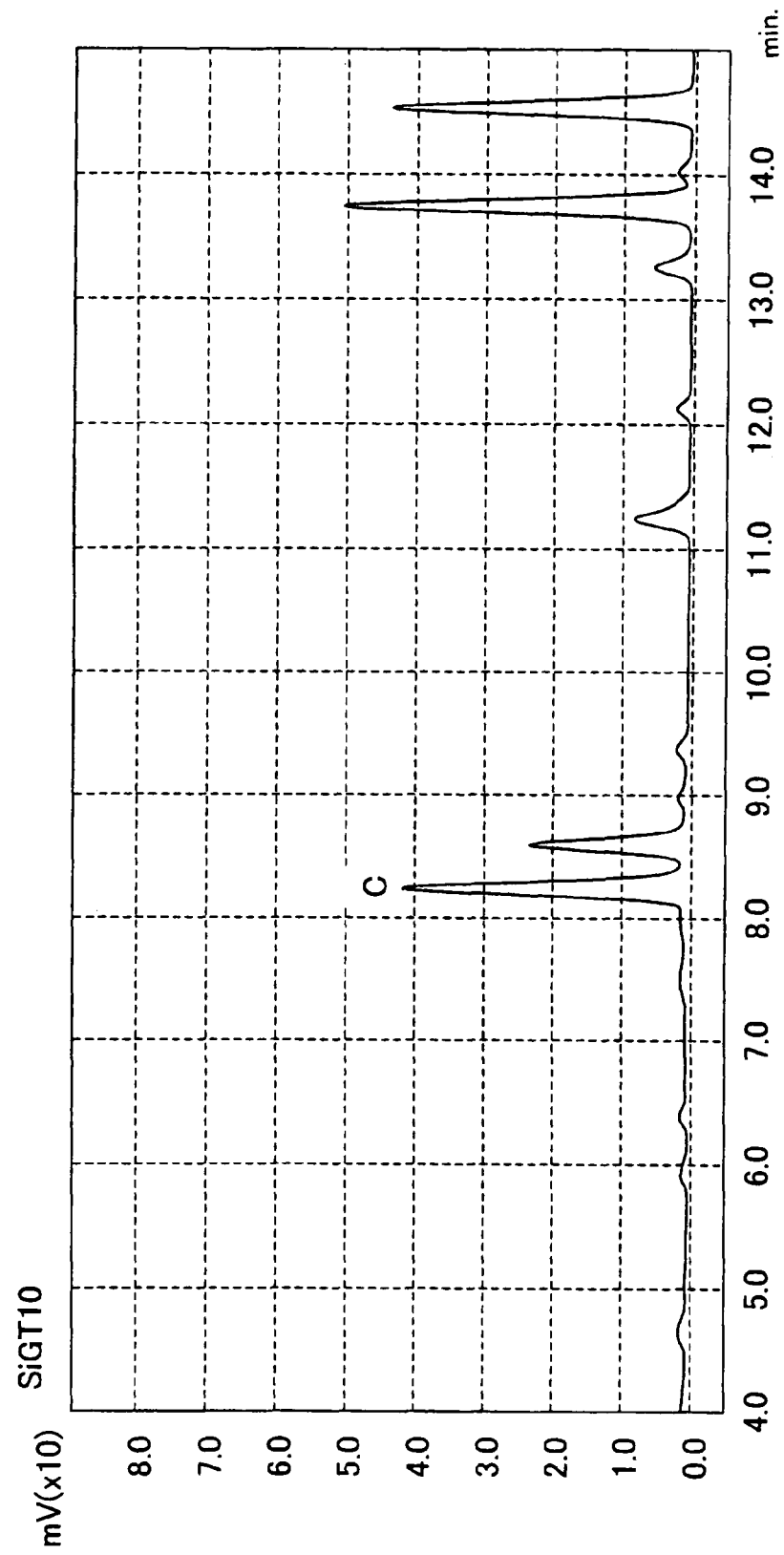
FIG. 2H is a graph showing the sesaminol glycosidation activity of SiGT protein (SiGT10).
Figure 2I:
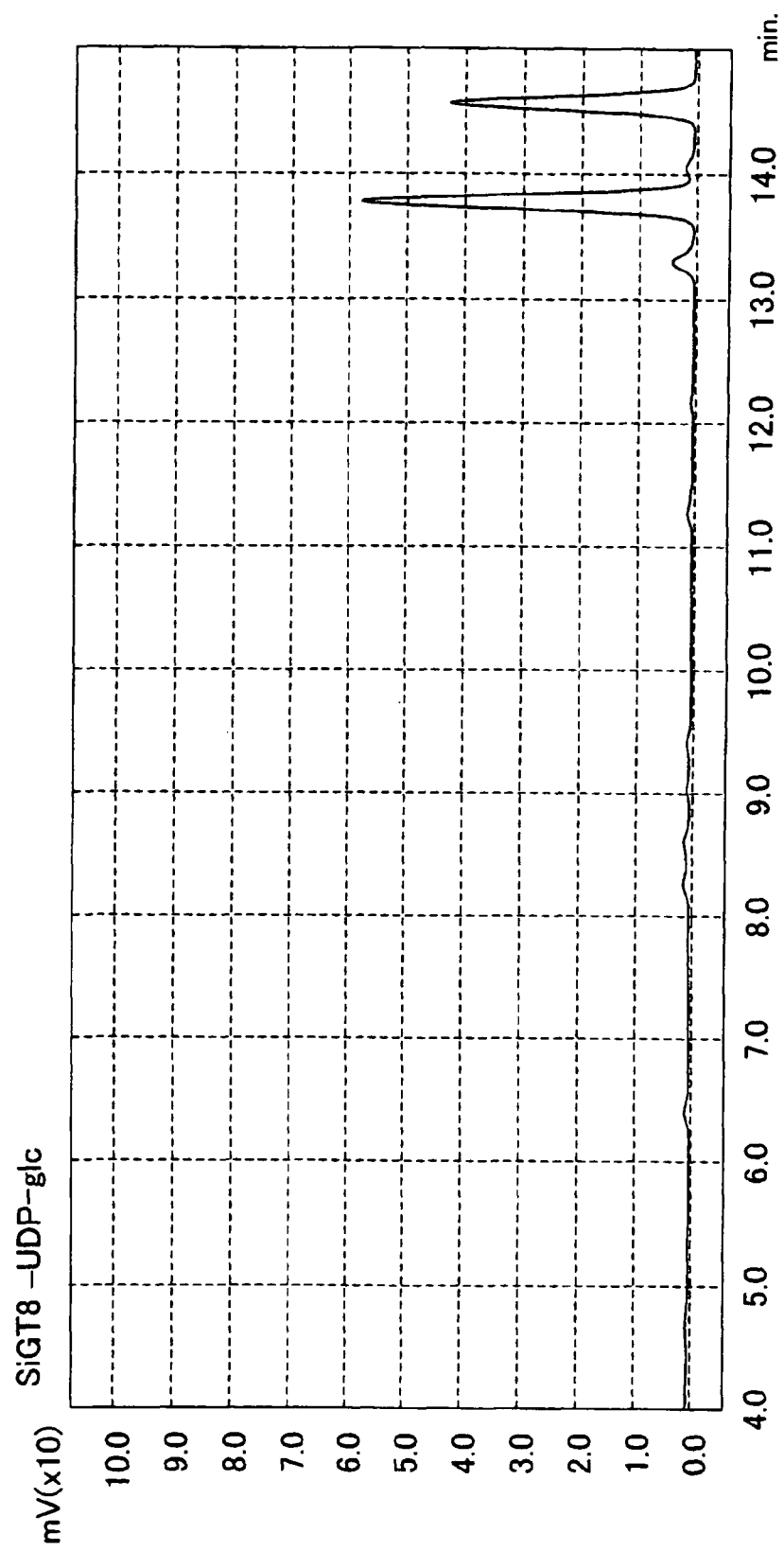
FIG. 2I is a graph showing the sesaminol glycosidation activity of SiGT protein (SiGT8) where UDP-glucose is removed from the enzyme reaction solution.
Figure 2J:
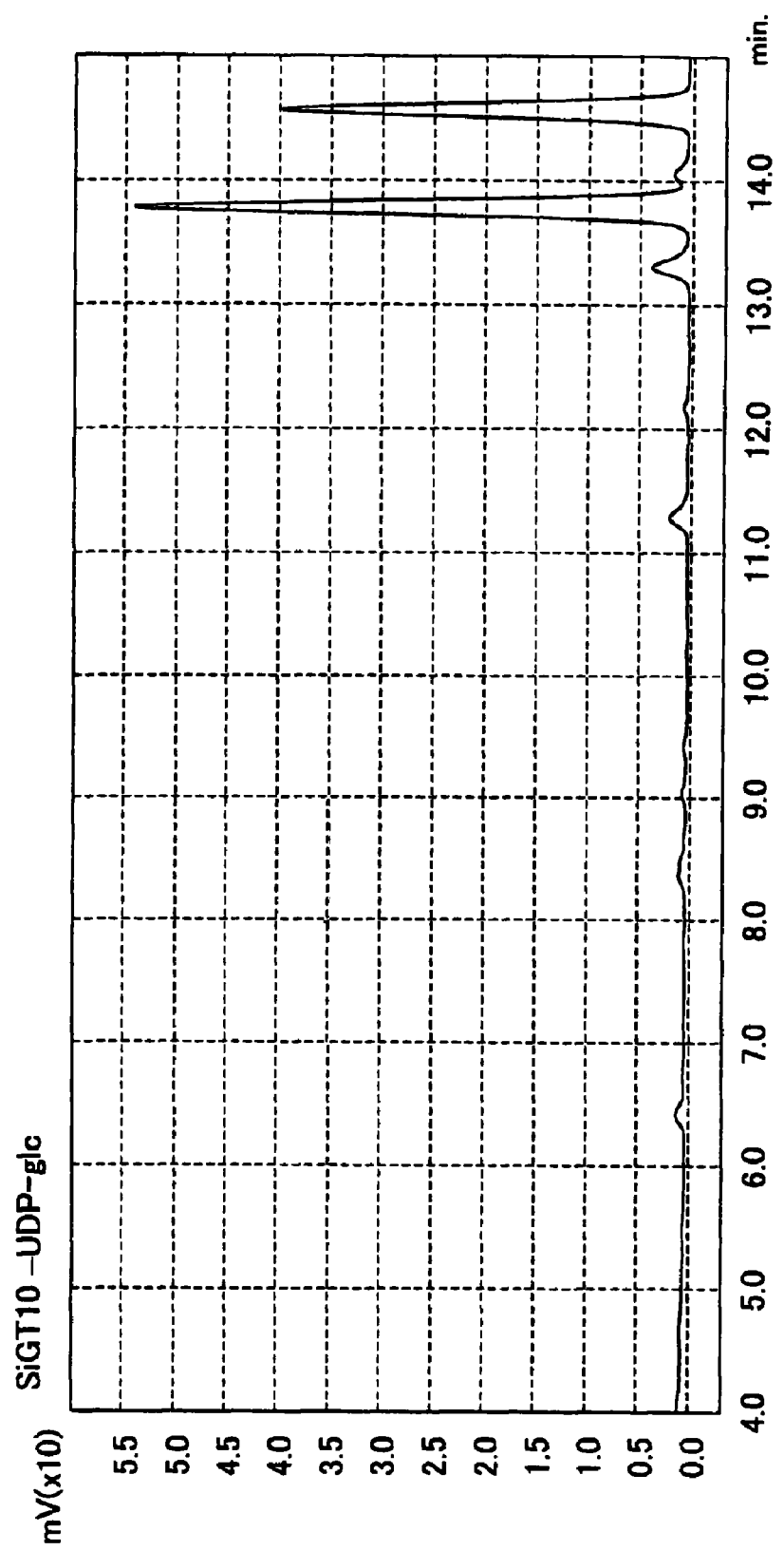
FIG. 2J is a graph showing the sesaminol glycosidation activity of SiGT protein (SiGT10) where UDP-glucose is removed from the enzyme reaction solution.

In the reaction solution of SiGT10 recombinant protein and pinoresinol, any new product was not observed (FIG. 2C). In the reaction solution of SiGT10 recombinant protein and sesaminol, peak C having the spectrum of lignan (retention time of about 8.2 minutes) was newly obtained (FIG. 2H).

Figure 3A:
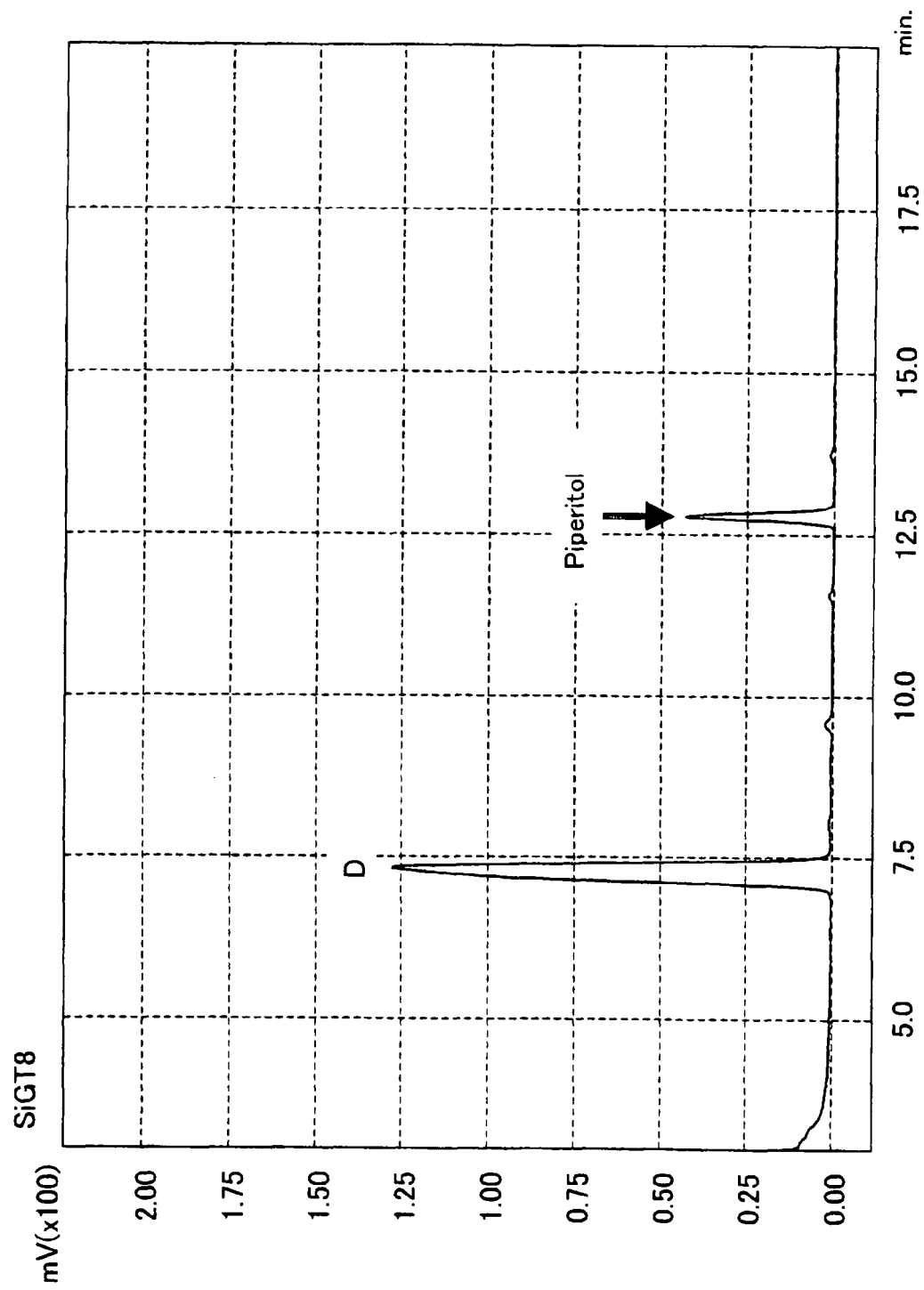
FIG. 3A is a graph showing the piperitol glycosidation activity of SiGT protein (SiGT8).
Figure 3B:
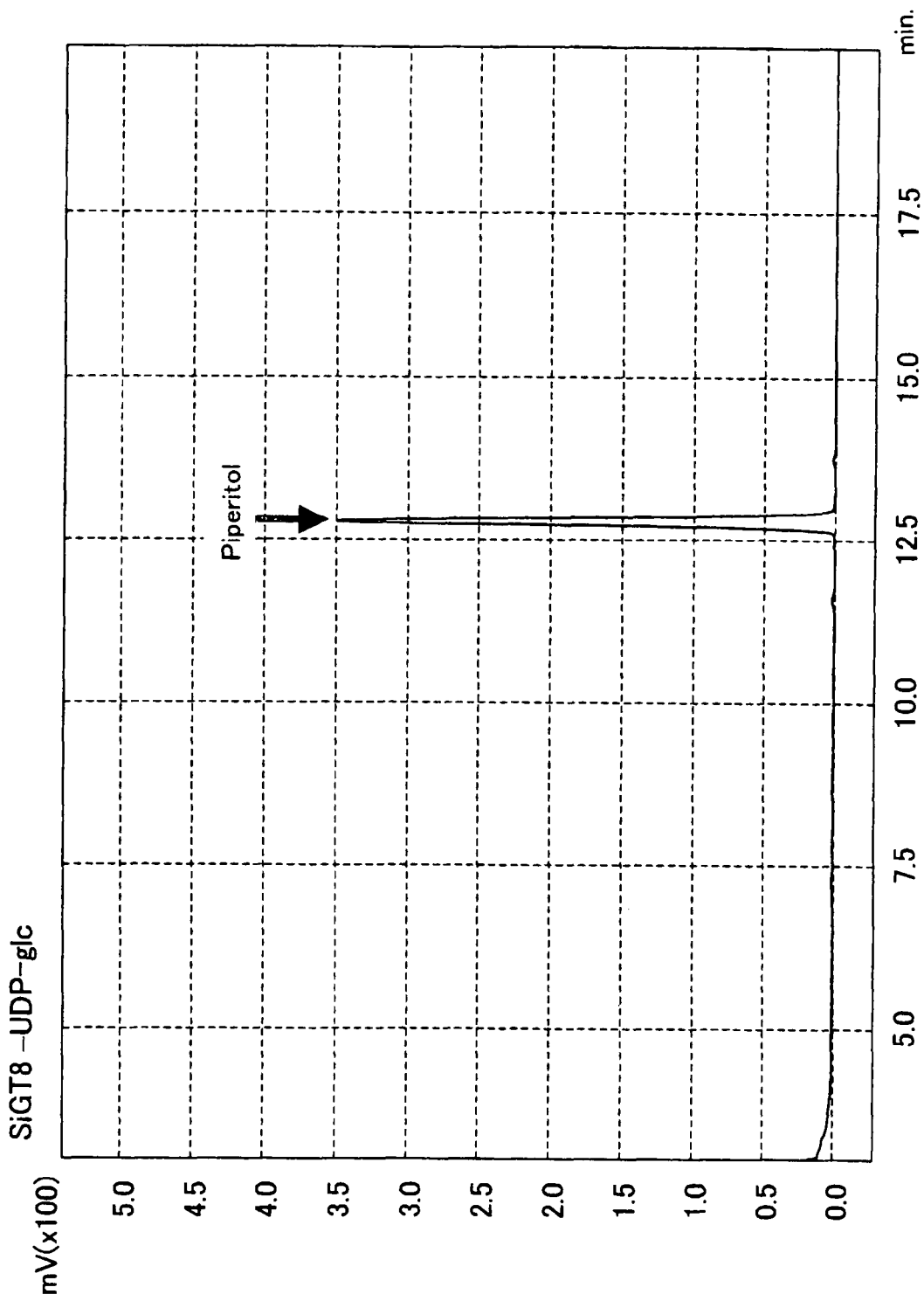
FIG. 3B is a graph showing the piperitol glycosidation activity of SiGT protein (SiGT8) where UDP-glucose is removed from the enzyme reaction solution.
Figure 3C:
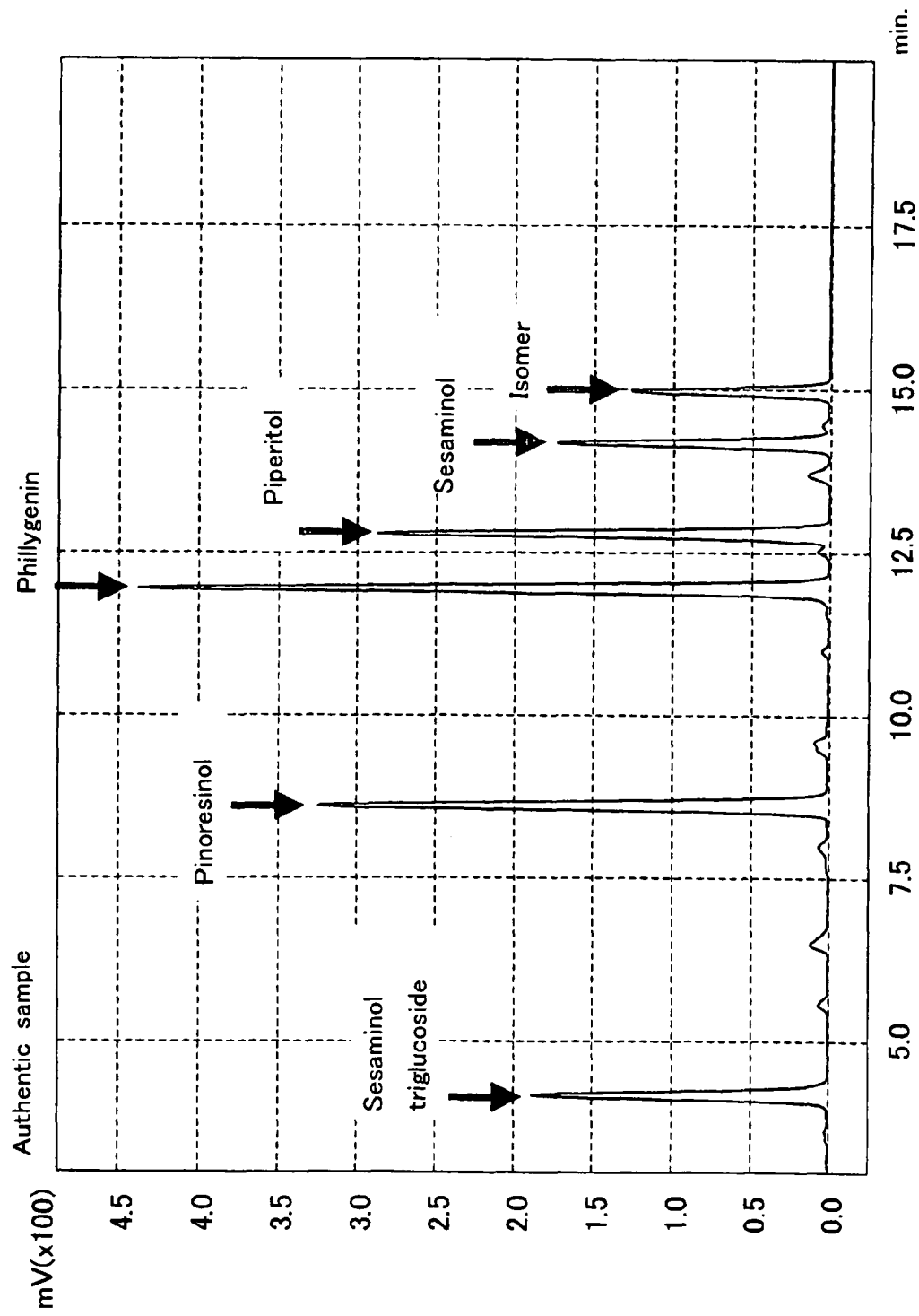
FIG. 3C is a graph showing the peaks of various authentic lignans.

Further in the reaction solution of SiGT8 recombinant protein and piperitol, peak D having the spectrum of lignan (retention time of about 7.4 minutes) was newly obtained (FIG. 3A).

The products shown as peaks A to D were not produced when UDP-glucose was removed from the enzyme reaction solution (FIGS. 2 and 3). This strongly suggested that these products are the glycosides of lignans added as the substrates. That is, peak A, peak B and peak C are pinoresinol glycoside, piperitol glycoside and sesaminol glycoside, respectively. Peak D is considered to be piperitol glycoside and this is a novel lignan glycoside, which has not been hitherto reported.

Example 9

Analysis of the Products from Sesame Lignan Glycosidases by LC-MS and TOF-MS/MS

By the LC-MS analysis, molecular weights of the lignan glycosides produced in EXAMPLE 8 were determined (liquid chromatography (LC): Waters 2795 (Waters Inc.), mass spectrograph: QUATRO micro (MICROMASS, Inc.)). A column packed with 1 ml of Diaion HP-20 resin (Mitsubishi Chemical) was washed with 5 ml of 50% acetone and then equilibrated with 10 ml of water. The enzyme reaction solution containing the lignan glycosides produced in EXAMPLE 8 was loaded on the column. After impurities were washed off with 5 ml of water, elution was performed with 2 ml of 80% acetone. After the eluant was evaporated to dryness using an evaporator, the residue was dissolved in 90% acetonitrile (100 μl) containing 1% formic acid and the solution was provided as a sample for the LC-MS analysis. The conditions for LC are shown below.

Using a Develosil C30-UG-3 column (Nomura Chemical, 3.0×150 mm), water as eluent A, 100% acetonitrile as eluent B, 1% formic acid as eluent C and 100 mM ammonium acetate aqueous solution as eluent D were used for the mobile phase. Elution was performed with a linear gradient (60% eluent A: 30% eluent B: 5% eluent C: 5% eluent D→10% eluent A: 80% eluent B: 5% eluent C: 5% eluent D) for 10 minutes (flow rate of 0.6 ml/min.) and then with 10% eluent A: 80% eluent B: 5% eluent C: 5% eluent D for 5 minutes (flow rate: always 0.2 ml/min.). Signals were detected as ammonium adduct ions.

Under the conditions, peak A is detected at about 6.1 minutes, peak B at about 9.6 minutes and peak D at about 8.8 minutes. The MS conditions of ion mode: ES+, cone voltage: 17V and collision 2V were used for MS scanning in the range of 300 to 600 (m/z, 18 mins.) to measure PDA in the range of 210 to 400 nm (18 minutes).

Figure 4A:
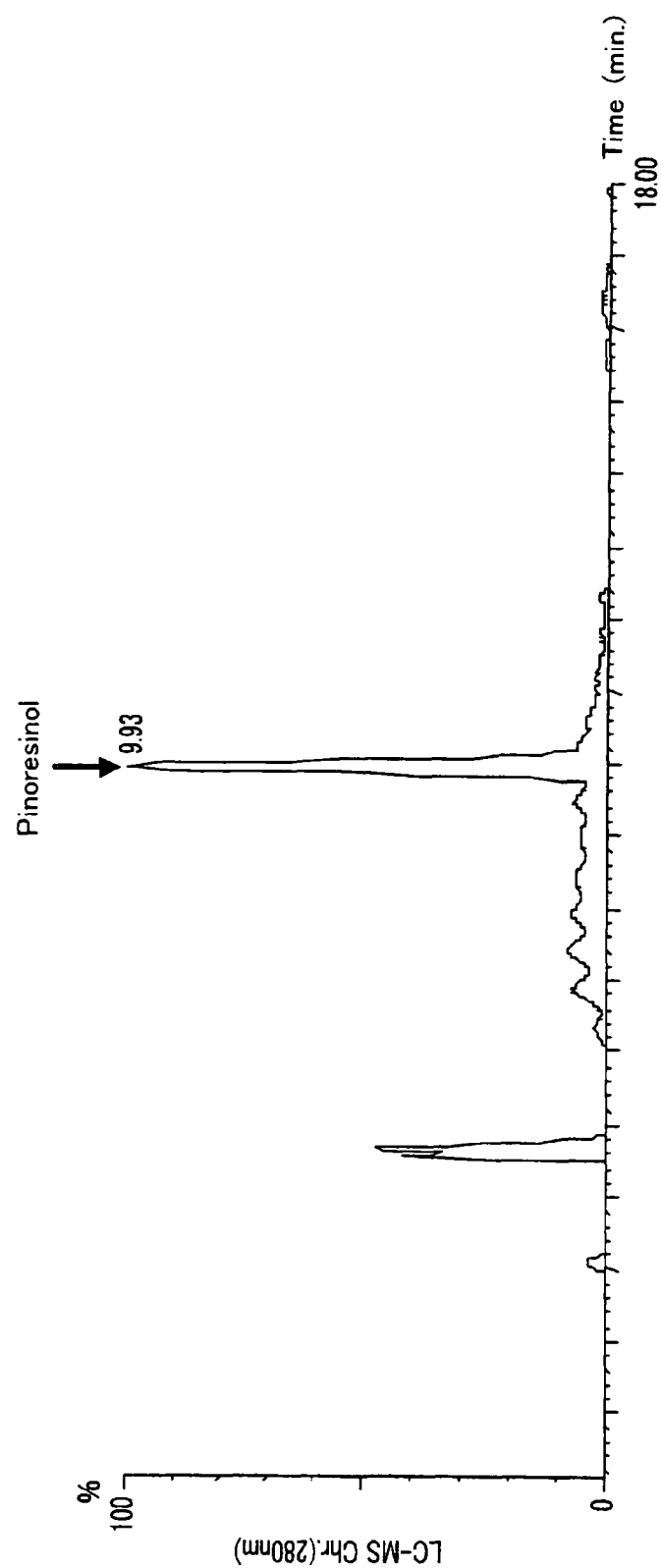
FIG. 4A is a graph showing the LC-MS analysis of pinoresinol.
Figure 4B:
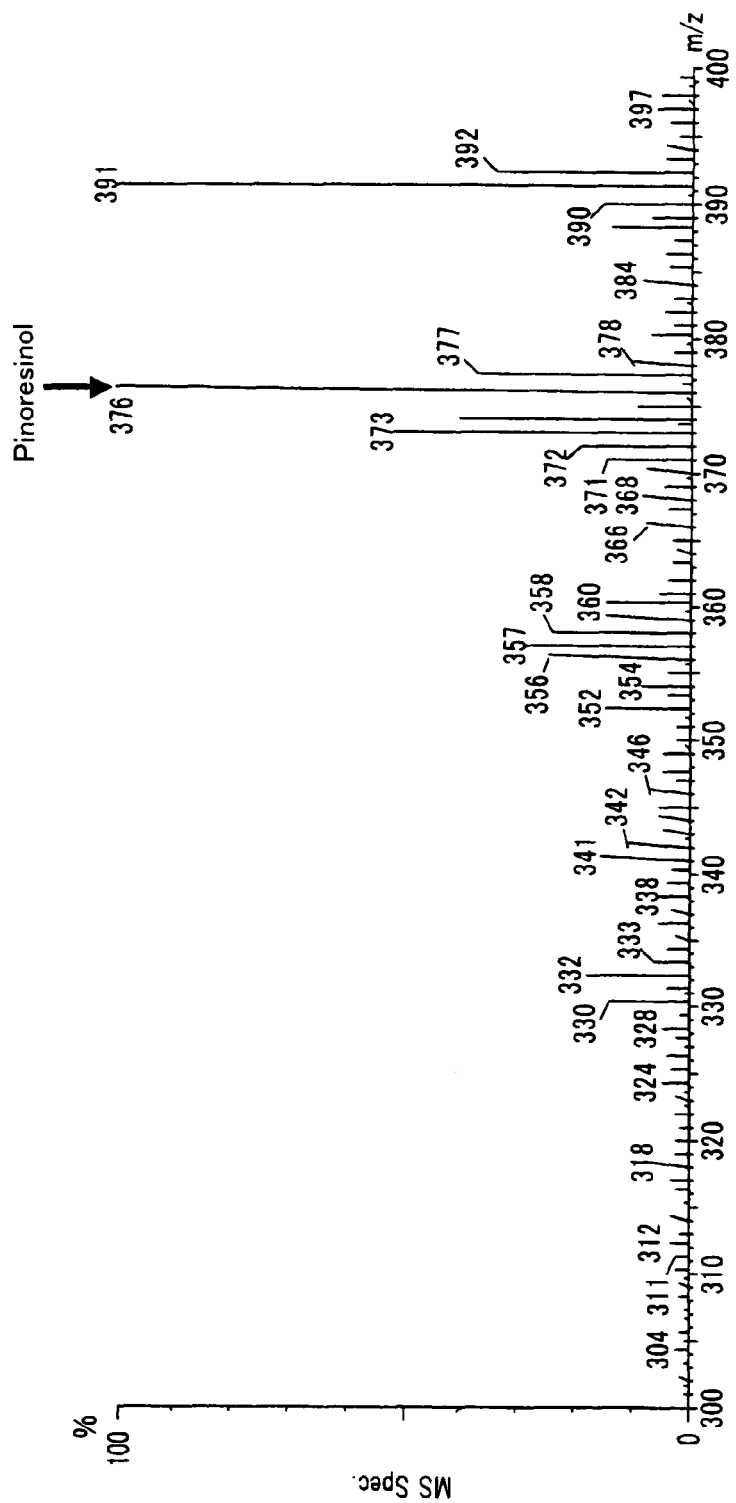
FIG. 4B is a graph showing the MS analysis of pinoresinol.
Figure 4C:
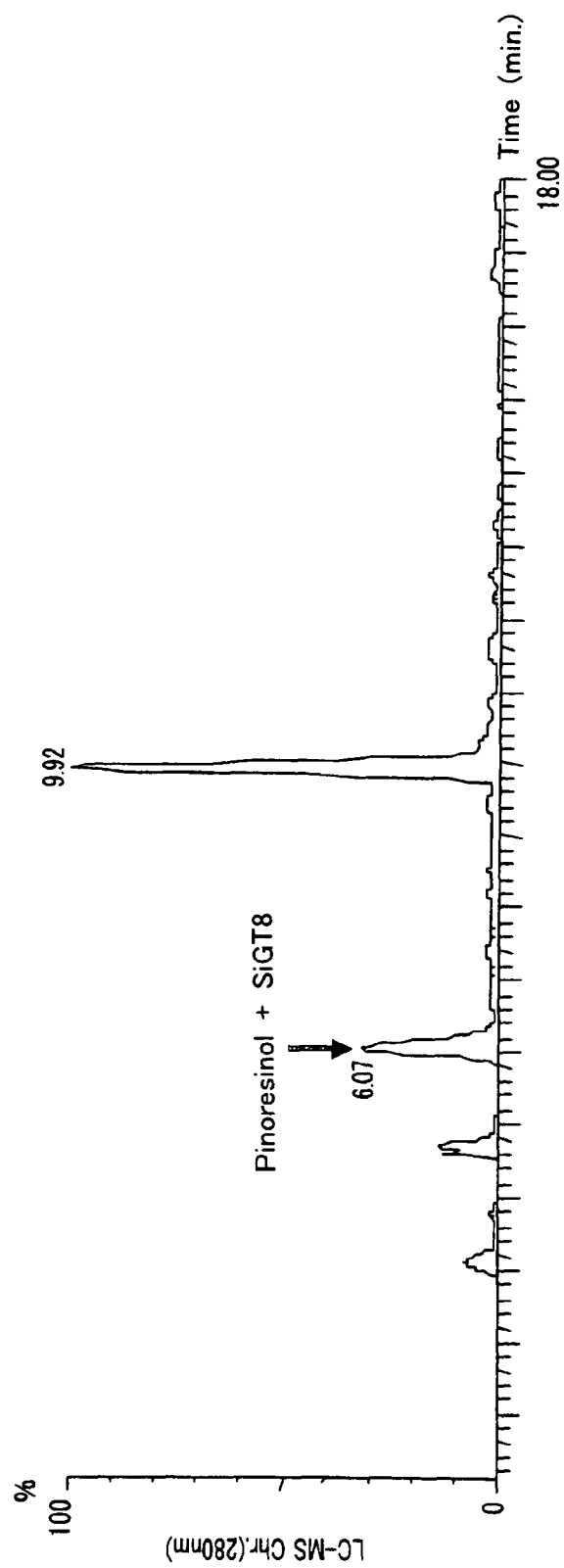
FIG. 4C is a graph showing the LC-MS analysis of the product of pinoresinol glycosidation reaction by SiGT8 protein.
Figure 4D:
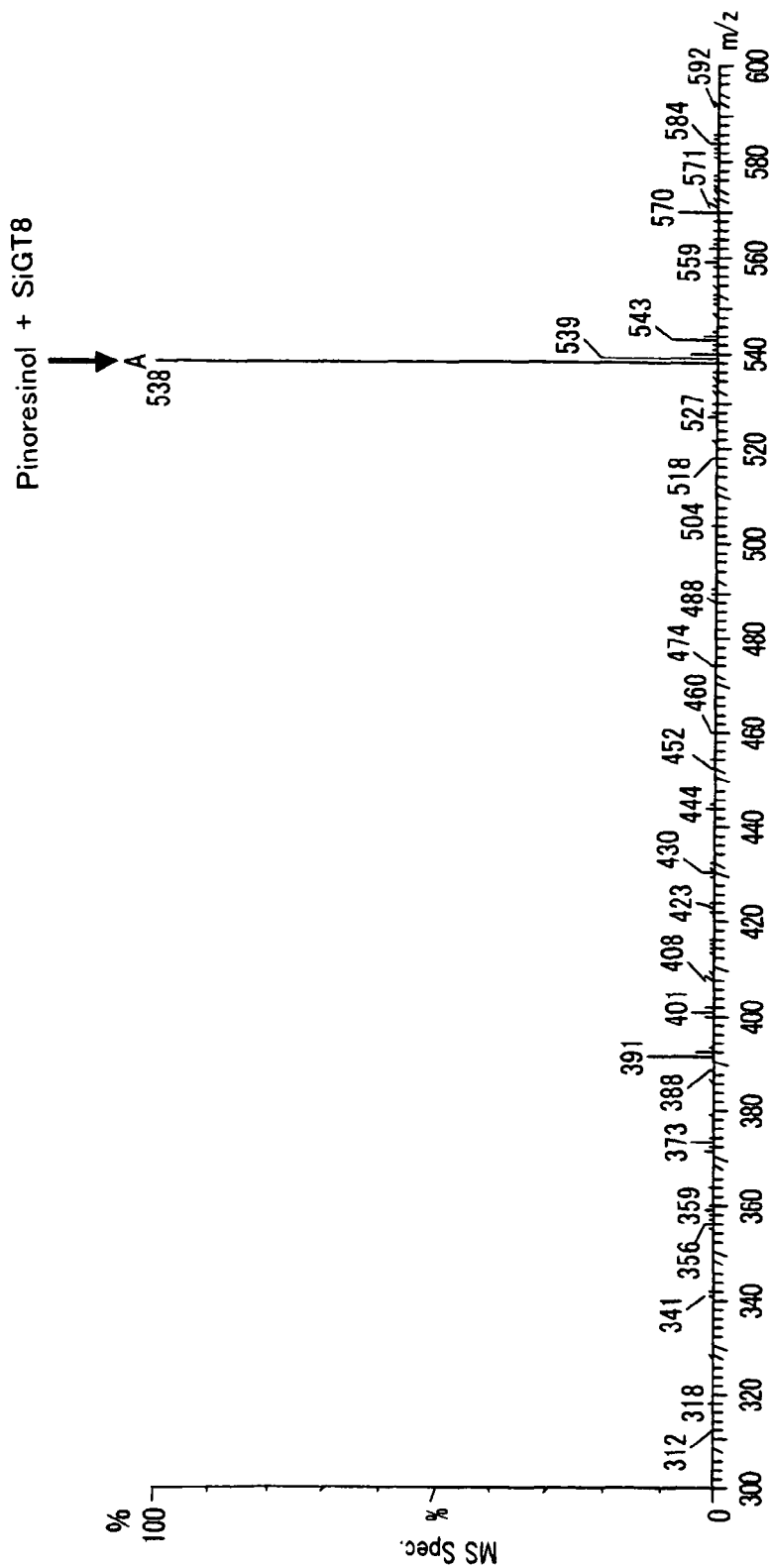
FIG. 4D is a graph showing the MS analysis of the product of pinoresinol glycosidation reaction by SiGT8 protein.
Figure 4E:
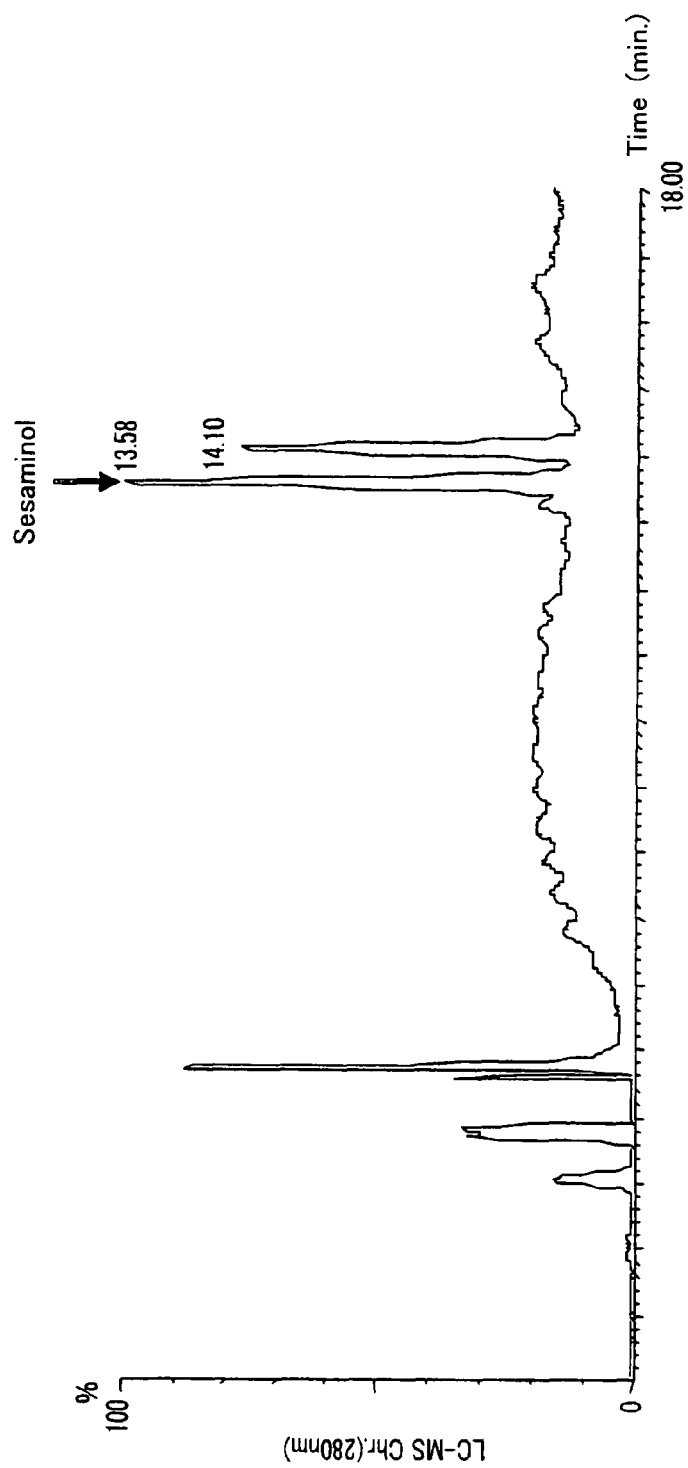
FIG. 4E is a graph showing the LC-MS analysis of sesaminol.
Figure 4F:
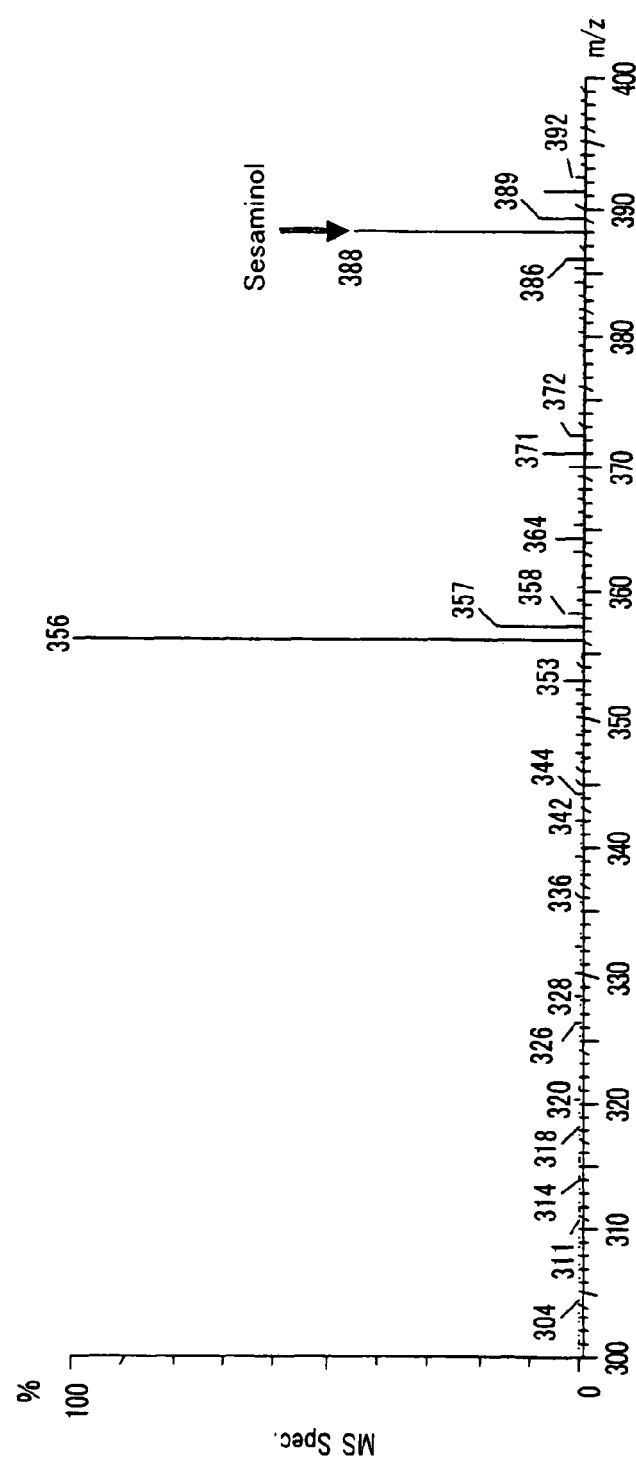
FIG. 4F is a graph showing the MS analysis of sesaminol.
Figure 4G:
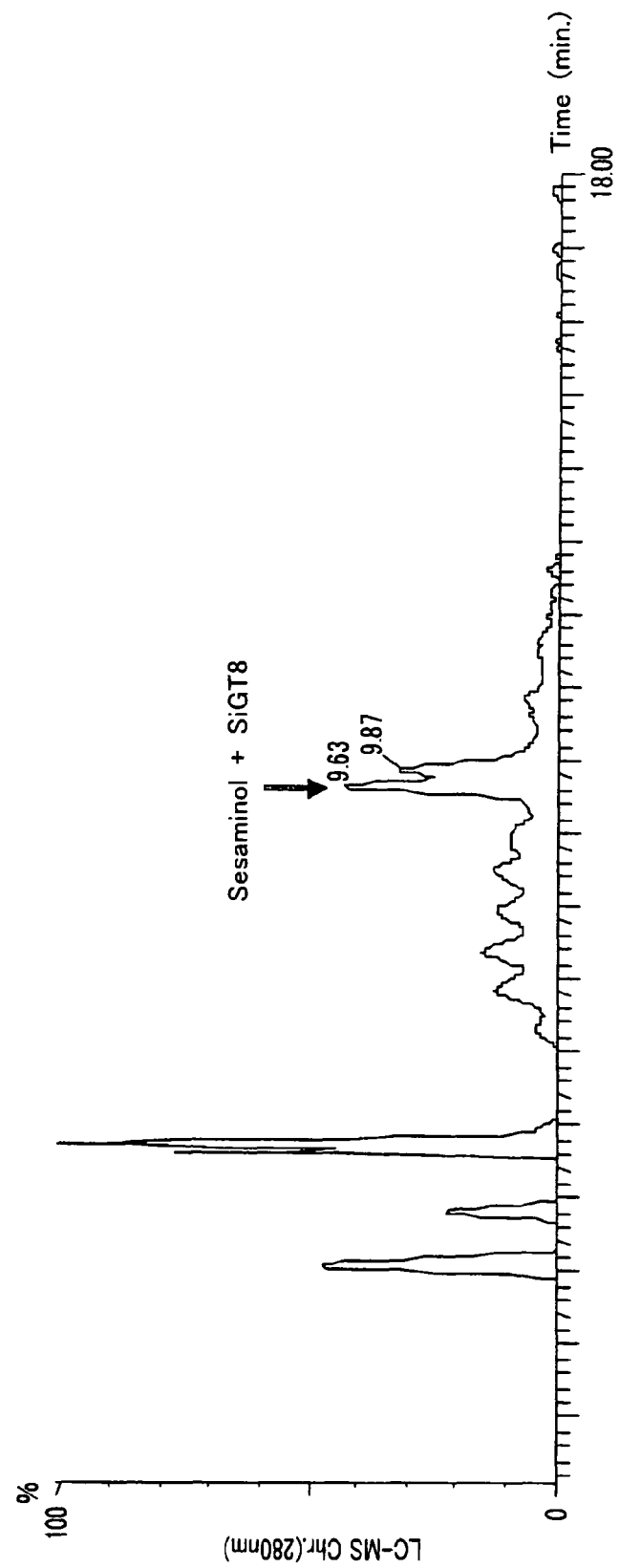
FIG. 4G is a graph showing the LC-MS analysis of the product of sesaminol glycosidation reaction by SiGT8 protein.
Figure 4H:
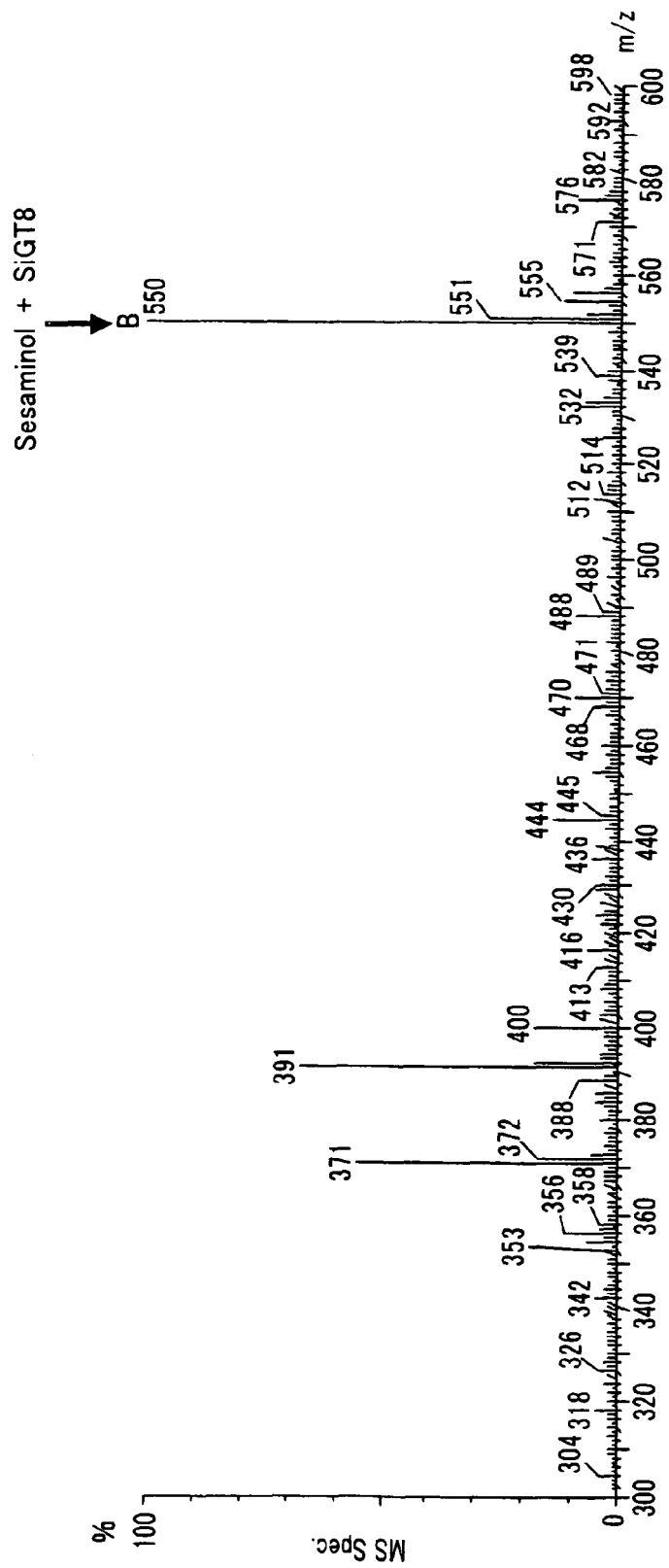
FIG. 4H is a graph showing the MS analysis of the product of sesaminol glycosidation reaction by SiGT8 protein.
Figure 4I:
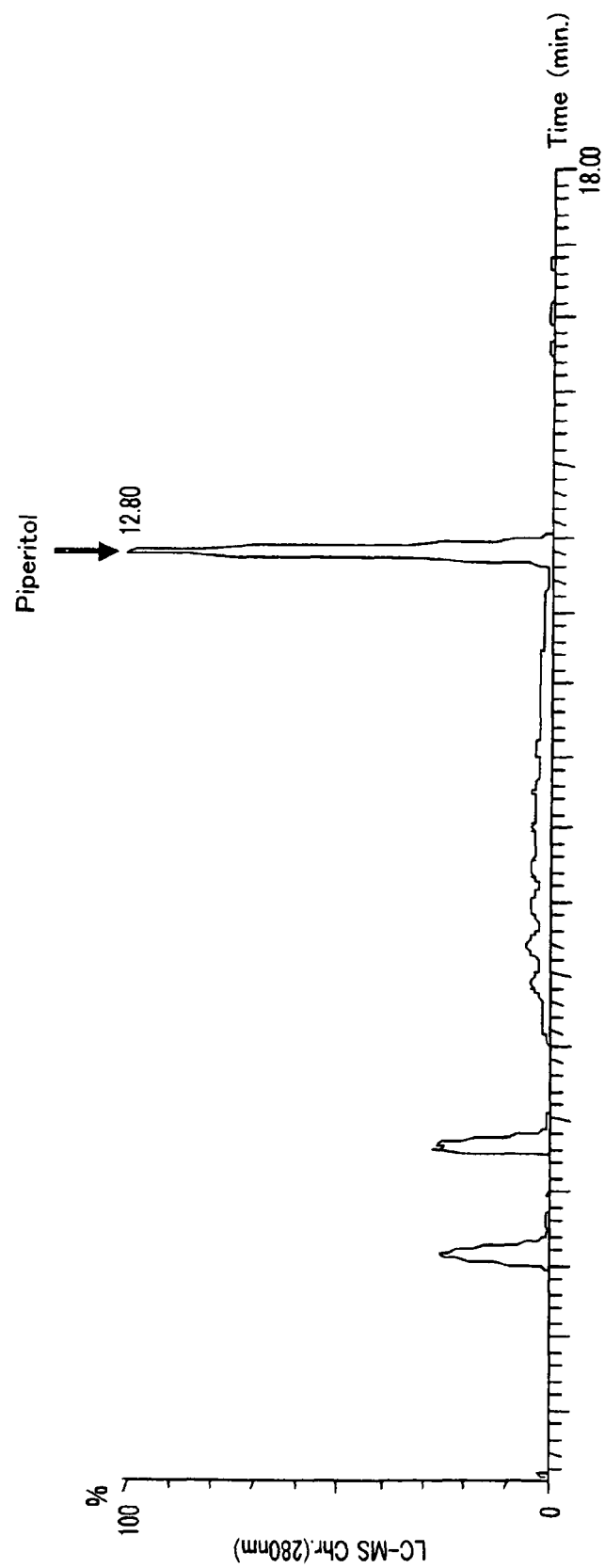
FIG. 4I is a graph showing the LC-MS analysis of piperitol.
Figure 4J:
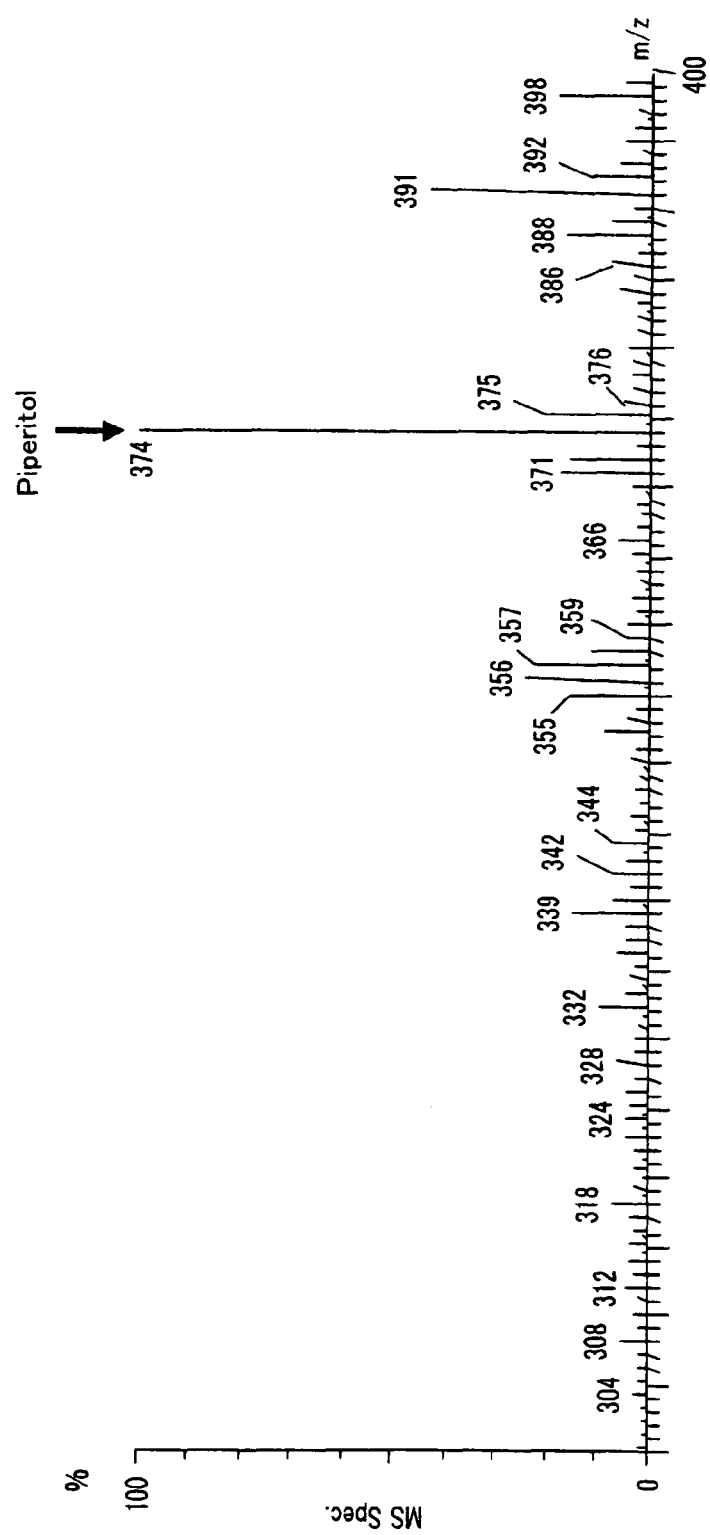
FIG. 4J is a graph showing the MS analysis of piperitol.
Figure 4K:
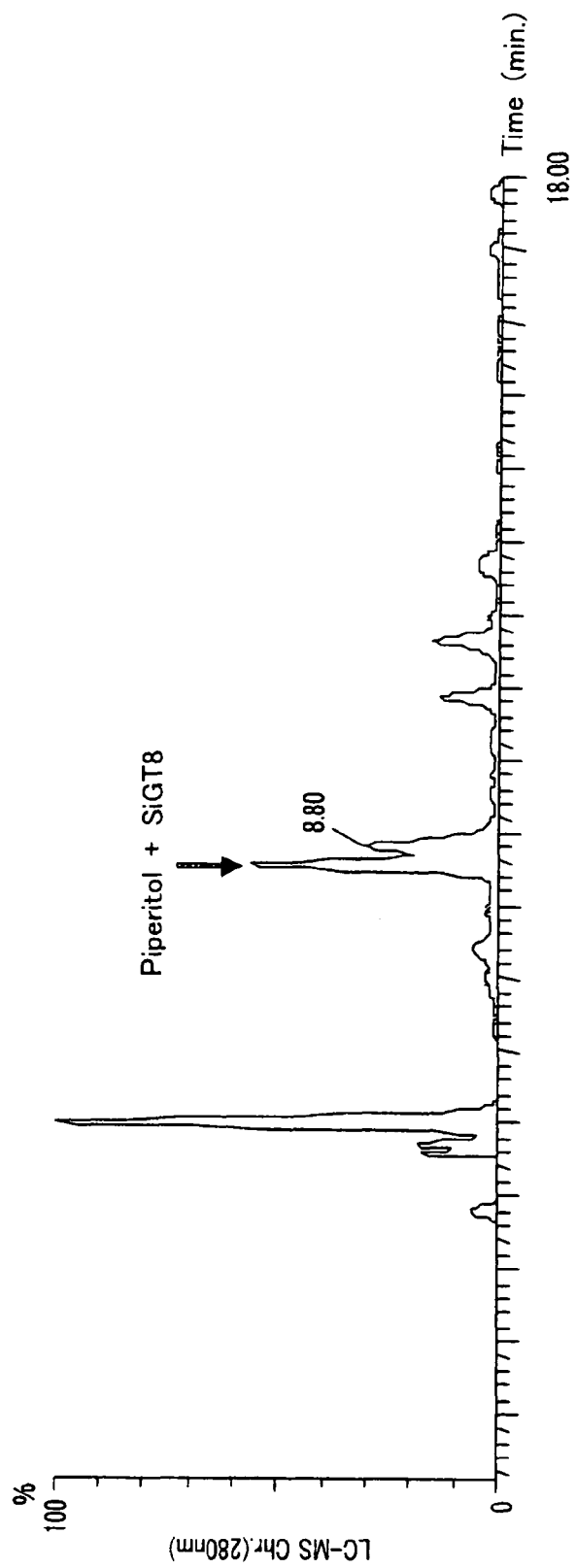
FIG. 4K is a graph showing the LC-MS analysis of the product of piperitol glycosidation reaction by SiGT8 protein.
Figure 4L:
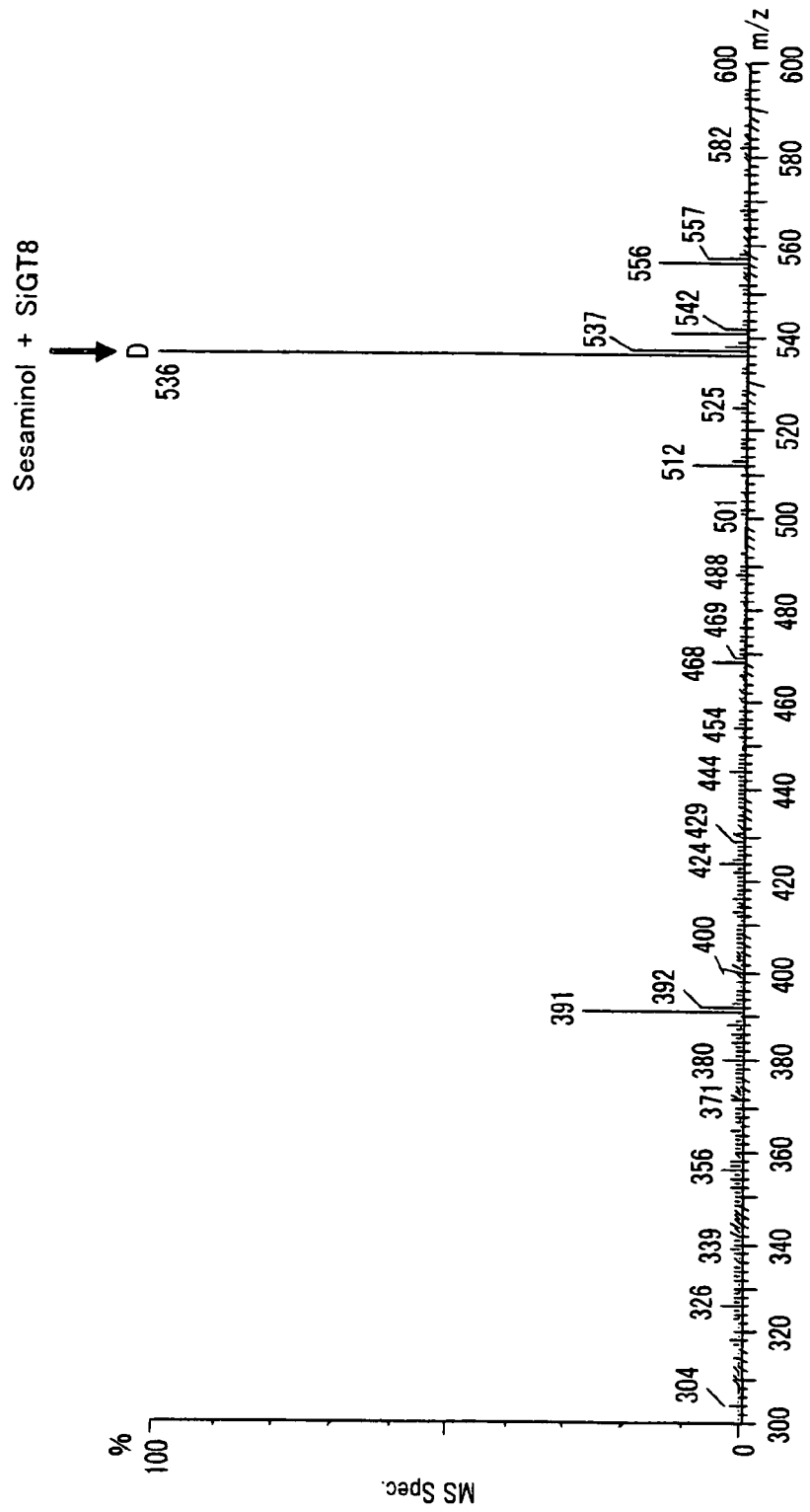
FIG. 4L is a graph showing the MS analysis of the product of piperitol glycosidation reaction by SiGT8 protein.

The results of the LC-MS analysis under the conditions described above indicate that peak A had the molecular weight of ammonium ion adduct at 538 (m/z), peak B had the molecular weight of ammonium ion adduct at 550 (m/z) and peak D had the molecular weight of ammonium ion adduct at 536 (m/z) (FIG. 4D, FIG. 4H and FIG. 4L). Thus, these peaks were identified to be monoglucoside of pinoresinol (molecular weight of ammonium ion adduct, 376), monoglucoside of piperitol (molecular weight of ammonium ion adduct, 388) and monoglucoside of sesaminol (molecular weight of ammonium ion adduct, 374), respectively.

In addition, the TOF-MS/MS analysis was performed for peak A and peak B. MS was measured using Q-TOF (Micromass, Manchester, UK) at a cone voltage of 17V, while increasing collision gradually in the order of 10 eV, 15 eV and 20 eV in a POSITIVE mode. Based on the results, fragments having molecular weights at 235 (m/z), 205 (m/z) and 175 (m/z) were identified for peak A. From the results it was confirmed that peak A was the pinoresinol skeleton. For peak B, fragments having molecular weights at 353 (m/z), 233 (m/z), 203 (m/z), 185 (m/z) and 135 (m/z) were identified. From the results it was confirmed that peak B was the sesaminol skeleton.

The foregoing results showed that the sesame-derived SiGT8 gene encoded lignan glycosidases having the activity to transfer a sugar onto pinoresinol, sesaminol and piperitol. The results also showed the SiGT10 gene encoded lignan glycosidases having the activity to transfer a sugar onto sesaminol.

Example 10

Structural Analysis of the Genes for Sesame Lignan Glycosidases

Genomic Southern analysis was performed to reveal the copy numbers of SiGT8 gene and SiGT10 gene in sesame genome.

Genomic DNA was extracted from the leaves of *S. indicum* (Masekin cultivar) using Nucleon Phytopure for Plant Extraction Kit (Amersham) according to the protocol recommended by the manufacturer. After 20 μg of the genomic DNA extracted was digested with EcoRV, XhoI, NcoI, KpnI or SpeI, the digestion products were separated by electrophoresis using agarose gel. This agarose gel was hydrolyzed in 0.25M HCl for 15 minutes, then denatured with a solution of 1.5M NaCl/0.5M NaOH (30 minutes) and neutralized in a denaturing solution (20 minutes) by adding 1.5M NaCl-containing Tris-HCl (pH 7.5). Next, the genomic DNA in the agarose gel was transferred to membrane (Hybribond-N, Amersham) in 20×SSC solution. The membrane-transferred genomic DNA was bound to membrane by UV irradiation and prehybridized at 42° C. for an hour using a hybridization buffer (High SDS buffer: Roche) composed of 7% SDS, 50% formamide, 5×SSC, 2% blocking agent, 0.1% lauroylsarcosine, 50 mM sodium phosphate buffer (pH 7.0).

Using pSPB2631 or pSPB2633 as a template, PCR was performed, respectively, using primer pairs of SEQ ID NO: 75 (NcoI-SiGT8-FW) and SEQ ID NO: 76 (KpnI-SiGT8-RV) or SEQ ID NO: 77 (NcoI-SiGT10-FW) and SEQ ID NO: 78 (KpnI-SiGT10-RV) to prepare DIG-labeled hybridization probes. A PCR solution comprised of 1 ng of the SiGT8 or SiGT10-containing plasmid described above, 1×PCR buffer (Takara Bio Inc.), 2.5 mM DIG-dNTP mixture (PCR DIG labeling Mix, Roche), 0.2 μmol of each primer and 1 U rTaq polymerase (Takara Bio Inc.). PCR was carried out by repeating 30 cycles of a reaction at 95° C. for 30 seconds, 53° C. for 30 seconds and 72° C. for 2 minutes. The PCR product purified on Sephadex G-50 column-Fine (Boehringer) was used as the hybridization probe. After this probe was heat denatured, 15 μl of the probe was added to the prehybridization solution, which was incubated at 42° C. overnight.

After hybridization, the membrane was washed under high stringent conditions (washing twice with a solution containing 0.2×SSC and 0.1% SDS at 65° C. for 30 minutes). Hybridization signals were detected using DIG Labeling & Detection Kit (Roche) according to the protocol recommended by the manufacturer.

Figure 5:
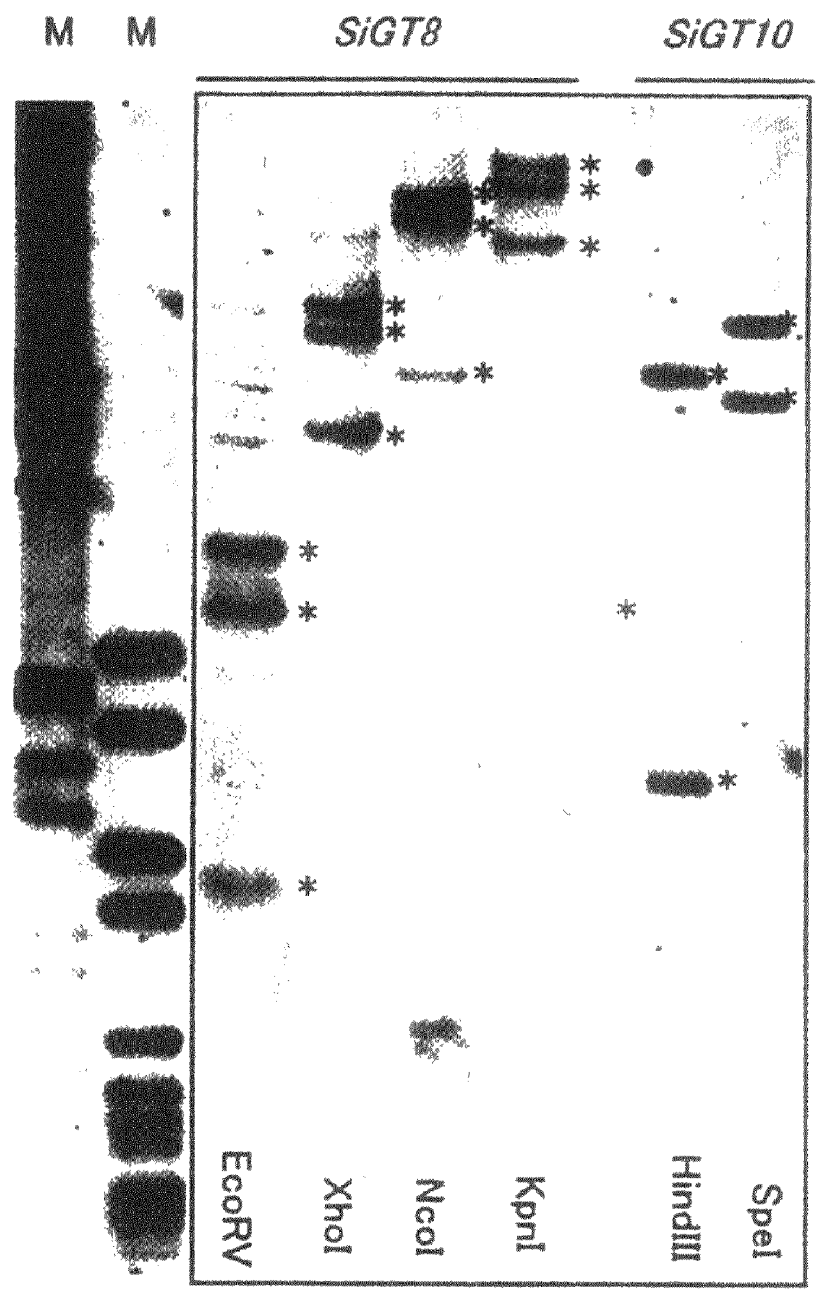
FIG. 5 is a graph showing the results of lignan glycosidase gene by Southern analysis.

The Southern analysis revealed that at least one SiGT gene having an extremely high homology to SiGT8 was encoded in the sesame genome, in addition to SiGT8 (FIG. 5). On the other hand, SiGT10 was shown to be present in the sesame genome as a single gene (FIG. 5).

Example 11

Isolation of SiGT8 Homolog from African Sesame (*Sesamum radiatum*)

In order to elucidate that the function of the SiGT8 gene product is conserved in various species, it was attempted to isolate the counterpart gene (SrSiGT8) of SiGT8 from *Sesamum radiatum* cytogenetically different from African sesame (*Sesamum indicum*) as a domesticated sesame variety.

*S. radiatum* is a sesame plant existing in Africa and India, considered to have the chromosome number of 2n=64 by cytogenetic analysis, and phylogenetically different from *S. indicum* (2n=26) of domesticated sesame variety (reference: Mitsuo Namiki, Teisaku Kobayashi, "Goma-no-Kagaku" (Science of Sesame), Asakura Publishing Co.). However, the seed of *S. radiatum* has been reported for the analysis of lignan contents, indicating that sesamin is accumulated therein (reference: Bedigian, D. et al., Biochemical Systematics and Ecology 13: 133-139 (1985)). It is thus expected that a gene corresponding to SiGT8 of *S. indicum* would be contained in the genome of *S. radiatum*.

As in EXAMPLE 4, cDNA of *S. radiatum* seed was synthesized. Using the primer pairs of SiGT8-BamHI-FW (SEQ ID NO: 79) and SiGT8-KpnI-RV (SEQ ID NO: 80), PCR was performed using 1 µl of this cDNA.

A PCR solution was composed of 1 µl of cDNA, 0.2 µmol/µl of each primer, 1×KOD plus buffer (TOYOBO), 0.2 mM dNTPs, 1 mM MgSO$_4$, and 1 U KOD plus polymerase. PCR was performed as follows. After reacting at 94° C. for 5 minutes, 30 cycles of the reaction at 94° C. for 1 minute, 50° C. for 1 minute and 72° C. for 2 minutes was carried out, and finally maintained at 72° C. for 3 minutes. As a result, about 1.4 kb fragment of the fragment predicted to contain the SiGT8 gene (SrSiGT8) of *S. radiatum* was amplified. This fragment was inserted into a multicloning site in pCR2Blunt-TOPO vector (Invitrogen) according to the protocol recommended by the manufacturer to obtain SrSiGT8/pCR2Blunt-TOPO (pSPB2656).
SiGT8-BamHI-FW: 5'-tttggatccatgtcggcggaccaaaaattaacca-3' (SEQ ID NO: 79)
SiGT8-KpnI-RV: 5'-tttggtacctcaagaaatgttattcacgacattct-3' (SEQ ID NO: 80).

The primer walking method was performed to determine the base sequence (and the amino acid sequence) of SrSiGT8 contained in pSPB2656 (SEQ ID NO: 81 and SEQ ID NO: 82). The SrSiGT8 gene showed 92% sequence identity in the nucleic acid sequence and 91% sequence identity in the amino acid sequence, to the SiGT8 gene. To assess the sequence identity, the Clustal W alignment program (Mac Vector ver. 7.2.2 (Symantec Corporation)) was used on default settings.

About 1.4 kb DNA fragment containing the full-length SrSiGT8 was excised from pSPB2656 with BamHI/KpnI and then ligated to the BamHI/KpnI site of pQE30 vector (QIAGEN), which was an expression vector for *Escherichia coli*, to obtain SrSiGT8/pQE30 (pSPB2657). This pSPB2657 expresses recombinant protein (His-SrSiGT8) with His tag consisting of 6 histidine residues fused to SrSiGT8 at the N terminus.

*Escherichia coli* transformed with pSPB2657 was incubated as in EXAMPLE 7 to express a recombinant protein. The following experiment was all carried out on ice or at 4° C., unless otherwise indicated.

After the cells were dissolved in 5 ml of lysis buffer (20 mM sodium phosphate buffer, 30 mM imidazole, 500 mM NaCl, 5 mM β-mercaptoethanol and 100 µM APSMF) per 1 g, the cells were lysed by ultrasonication, followed by centrifugation at 4000 rpm for 10 minutes. The supernatant obtained was recovered as the crude enzyme solution.

Next, the His-SrSiGT8 recombinant protein was purified through a Ni column. Chelating Sepharose FF resin (Amersham Bioscience) was packed in the column and 0.1M NiSO$_4$ in a volume equal to the resin was added to the resin. Subsequently, the column was washed with water in a volume twice the volume of the resin and then with 20% ethanol in a volume 3 times the volume of the resin.

Then, the column was equilibrated with a lysis buffer in a volume 5 times the volume of the resin and a sample obtained by diluting 5 mL of the crude enzyme solution described above with the lysis buffer to 10-fold was loaded on the column. After the sample naturally dropped by the gravity, the sample was washed 3 times with the lysis buffer in a volume 5 times the volume of the resin and then eluted using 5 ml of an elution buffer (20 mM sodium phosphate buffer, 500 mM imidazole, 500 mM NaCl, 5 mM β-mercaptoethanol and 100 µM APSMF)

Figure 6A:
FIG. 6A shows photographs of SDS-PAGE gel confirming the expression of *Sesamum radiatum*-derived SrSiGT8.
Figure 6B:
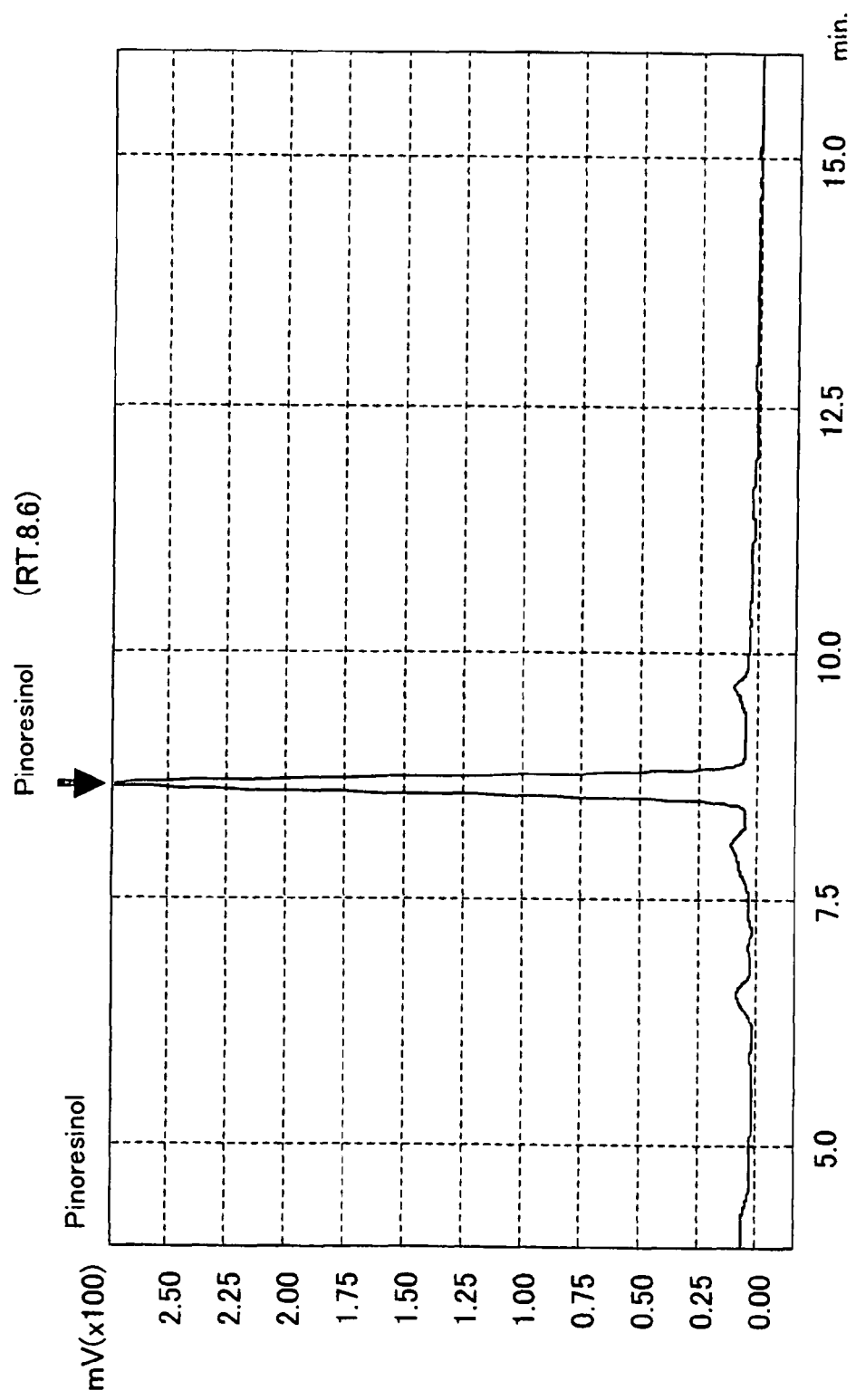
FIG. 6B is a graph showing the results obtained by assaying the pinoresinol glycosidation activity of *Sesamum radiatum*-derived SrSiGT8.

The eluate, 10 µl, was applied to SDS-PAGE and it was confirmed by CBB staining that the His-SrSiGT8 recombinant protein was expressed in a size of about 60 kDa (FIG. 6A).

Subsequently, the eluted fraction containing the His-SrSiGT8 recombinant protein as almost a single band was packed in a cellulose tube (DIALYSIS TUBING, SIGMA) and dialyzed in a dialysis buffer (30 mM sodium phosphate buffer, 30 mM NaCl, 5 mM β-mercaptoethanol and 100 µM APSMF) overnight.

To 300 µl of the dialyzed sample, 20 µl of the substrate solution (1 mg/ml) and 3 µl of 20 mM UDP-glucose were added to react at 30° C. for an hour. The reaction product was analyzed in a manner similar to EXAMPLE 8.

Figure 6C:
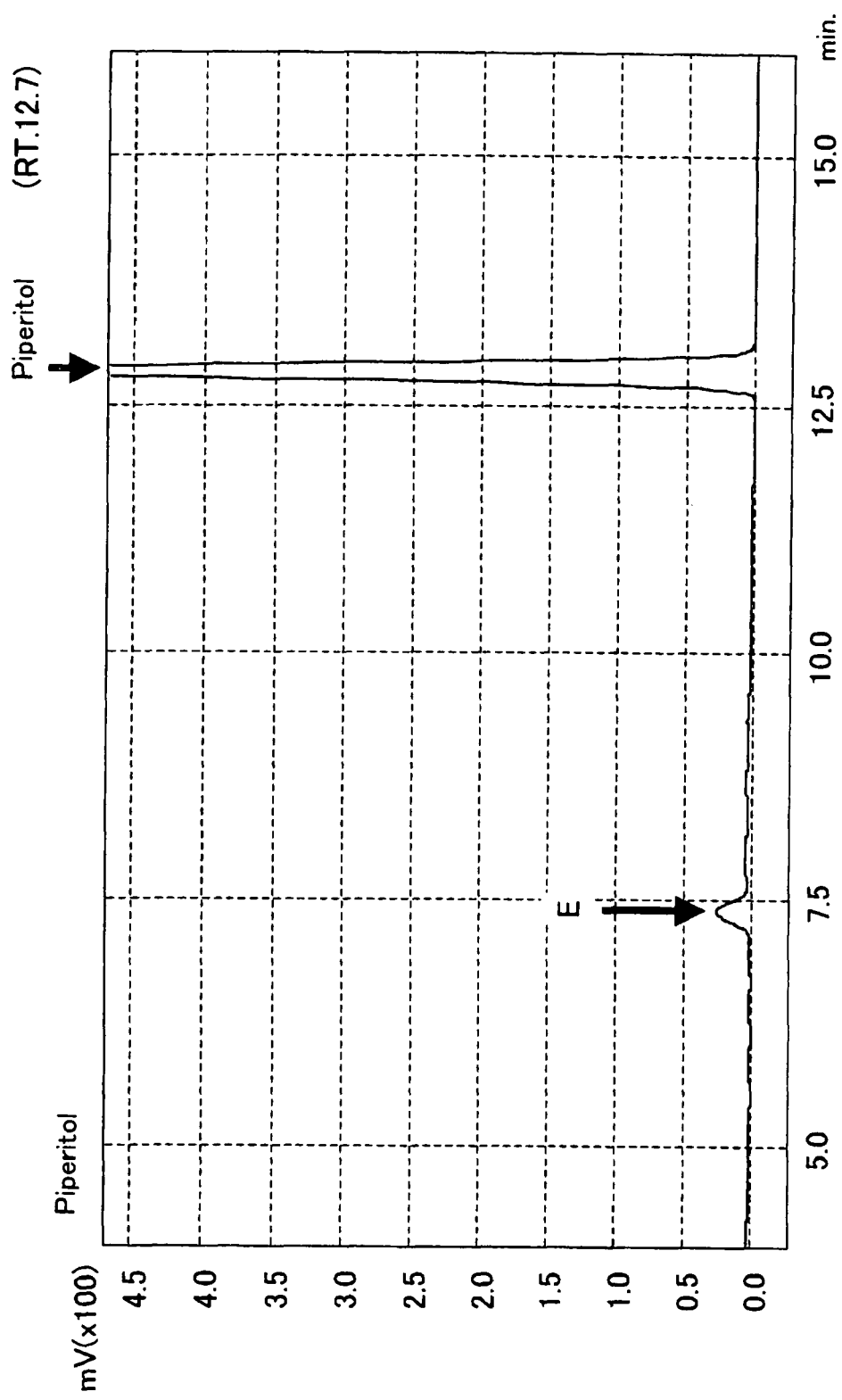
FIG. 6C is a graph showing the results obtained by assaying the piperitol glycosidation activity of *Sesamum radiatum*-derived SrSiGT8.
Figure 6D:
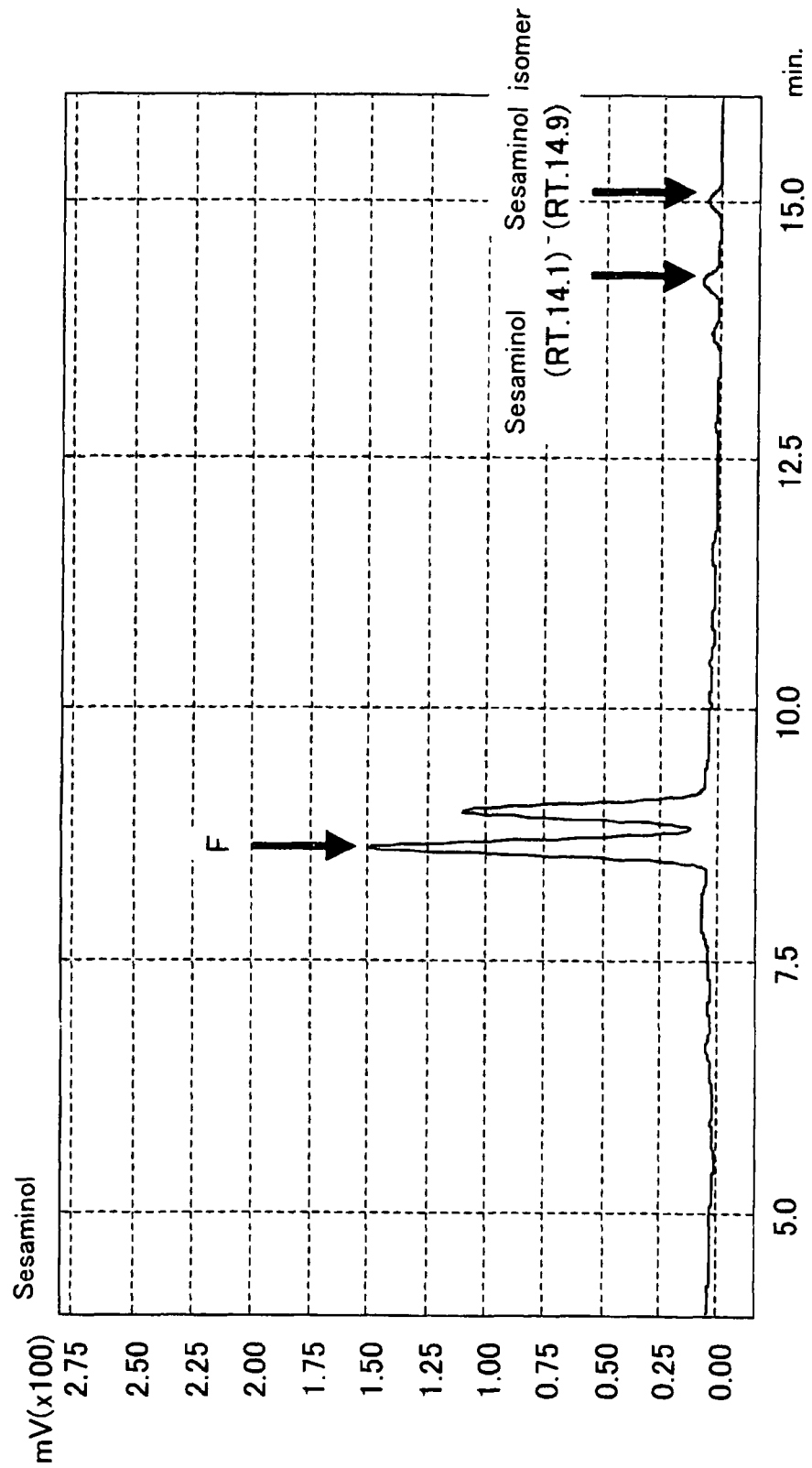
FIG. 6D is a graph showing the results obtained by assaying the sesaminol glycosidation activity of *Sesamum radiatum*-derived SrSiGT8.
Figure 6E:
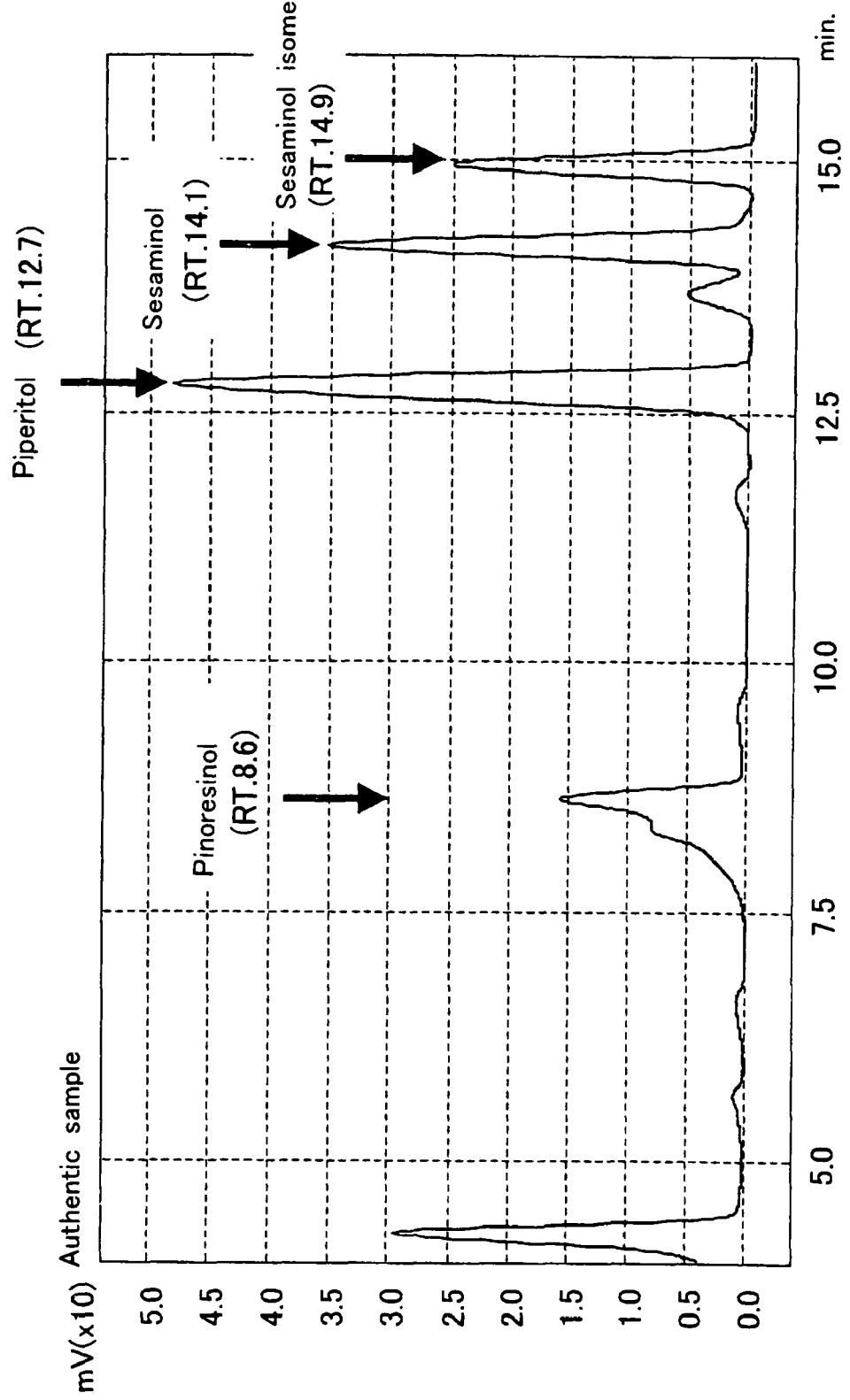
FIG. 6E is a graph showing the peaks of various authentic lignans.
Figure 6F:
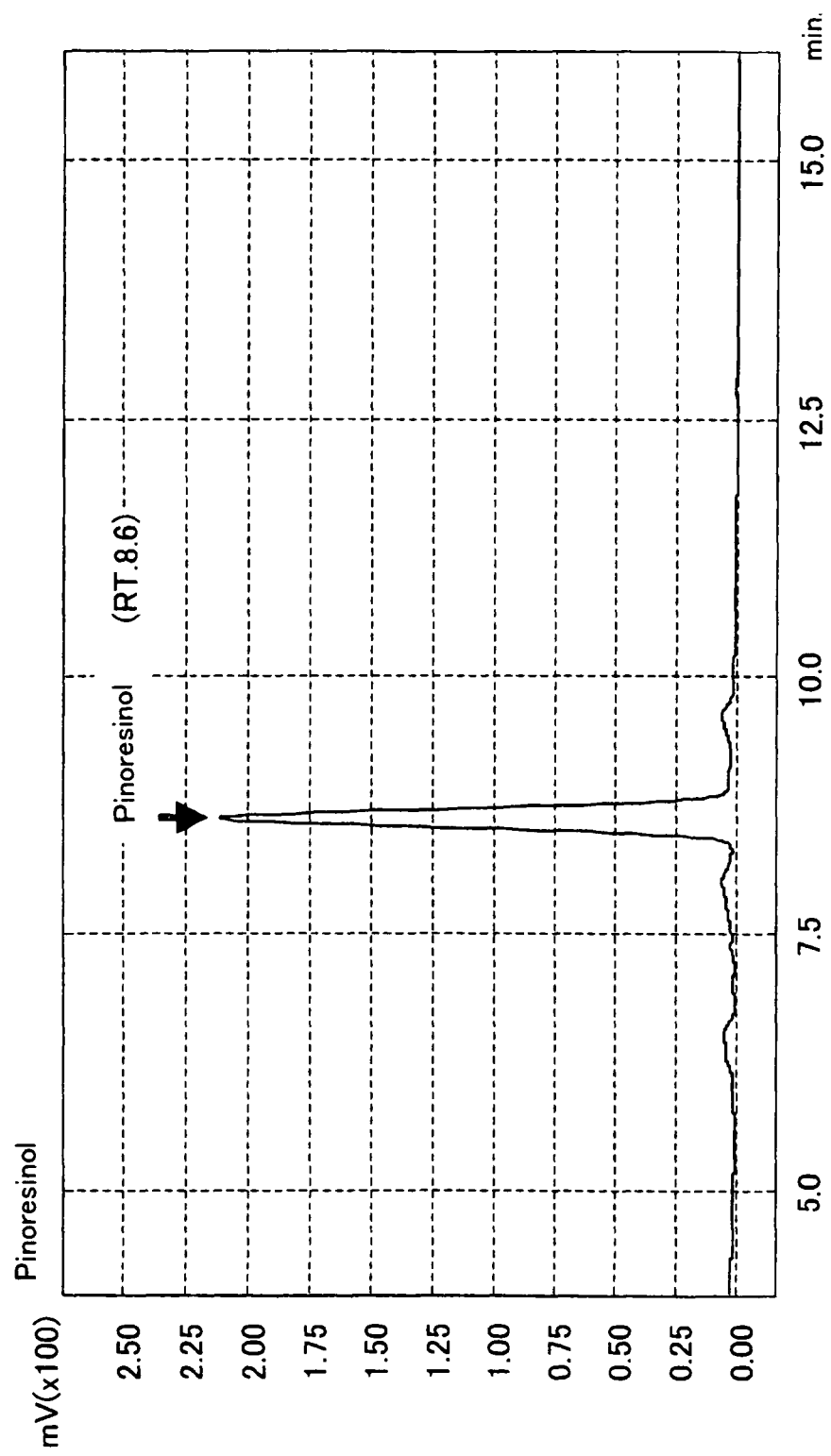
FIG. 6F is a graph showing the pinoresinol glycosidation activity of *Sesamum radiatum*-derived SrSiGT8 where UDP-glucose is removed from the enzyme reaction solution.
Figure 6G:
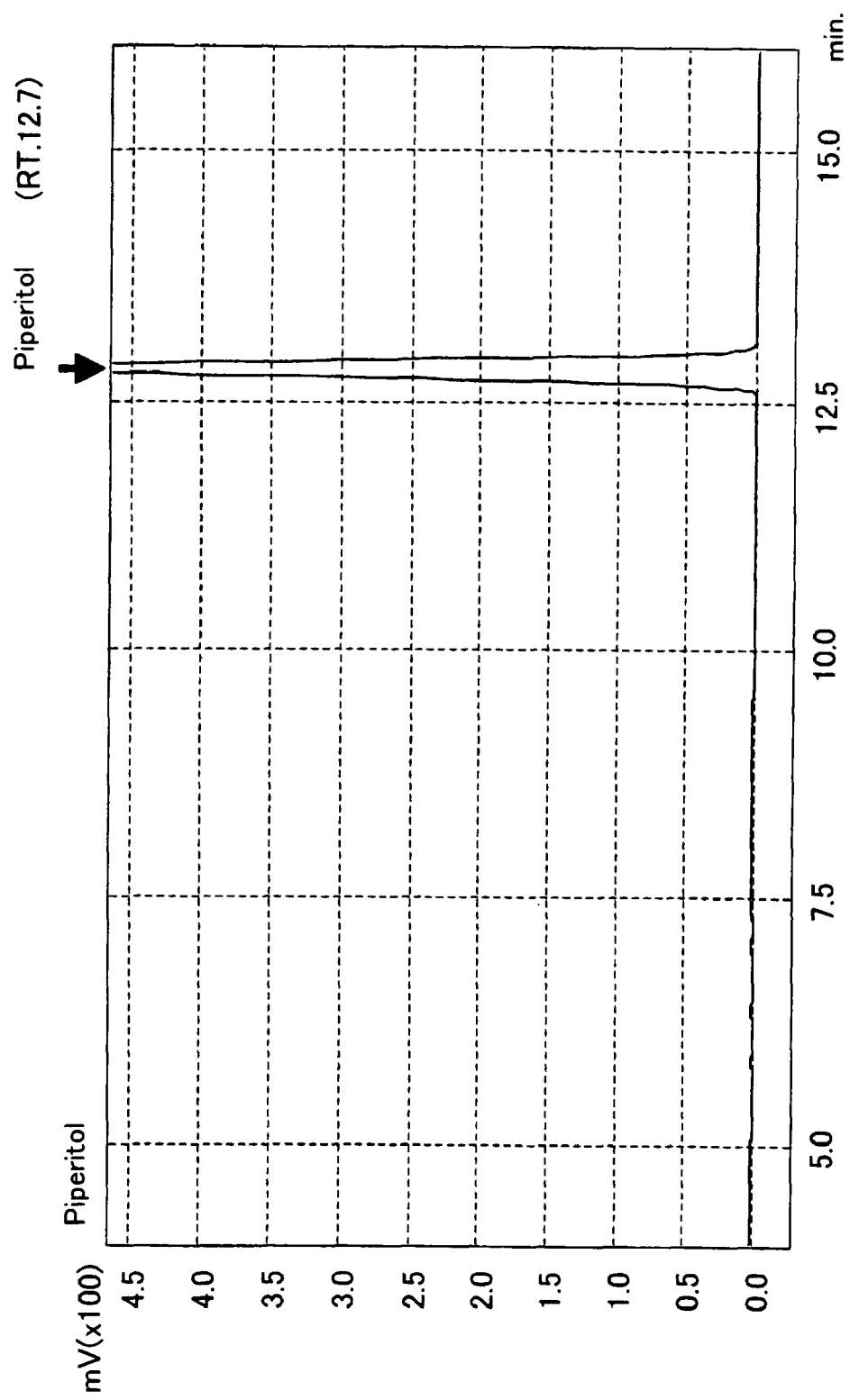
FIG. 6G is a graph showing the piperitol glycosidation activity of *Sesamum radiatum*-derived SrSiGT8 where UDP-glucose is removed from the enzyme reaction solution.
Figure 6H:
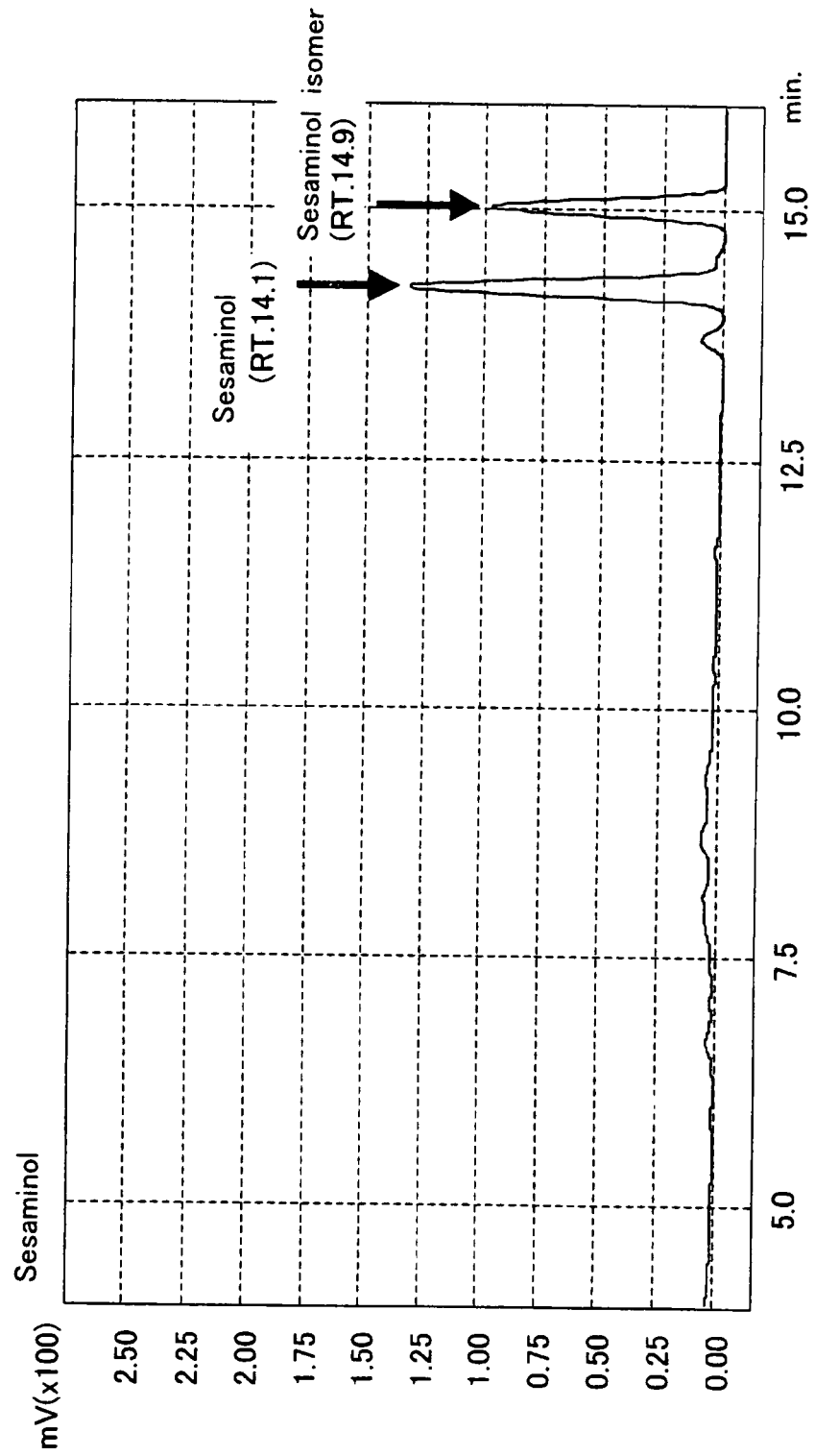
FIG. 6H is a graph showing the sesaminol glycosidation activity of *Sesamum radiatum*-derived SrSiGT8 where UDP-glucose is removed from the enzyme reaction solution.
Figure 7A:
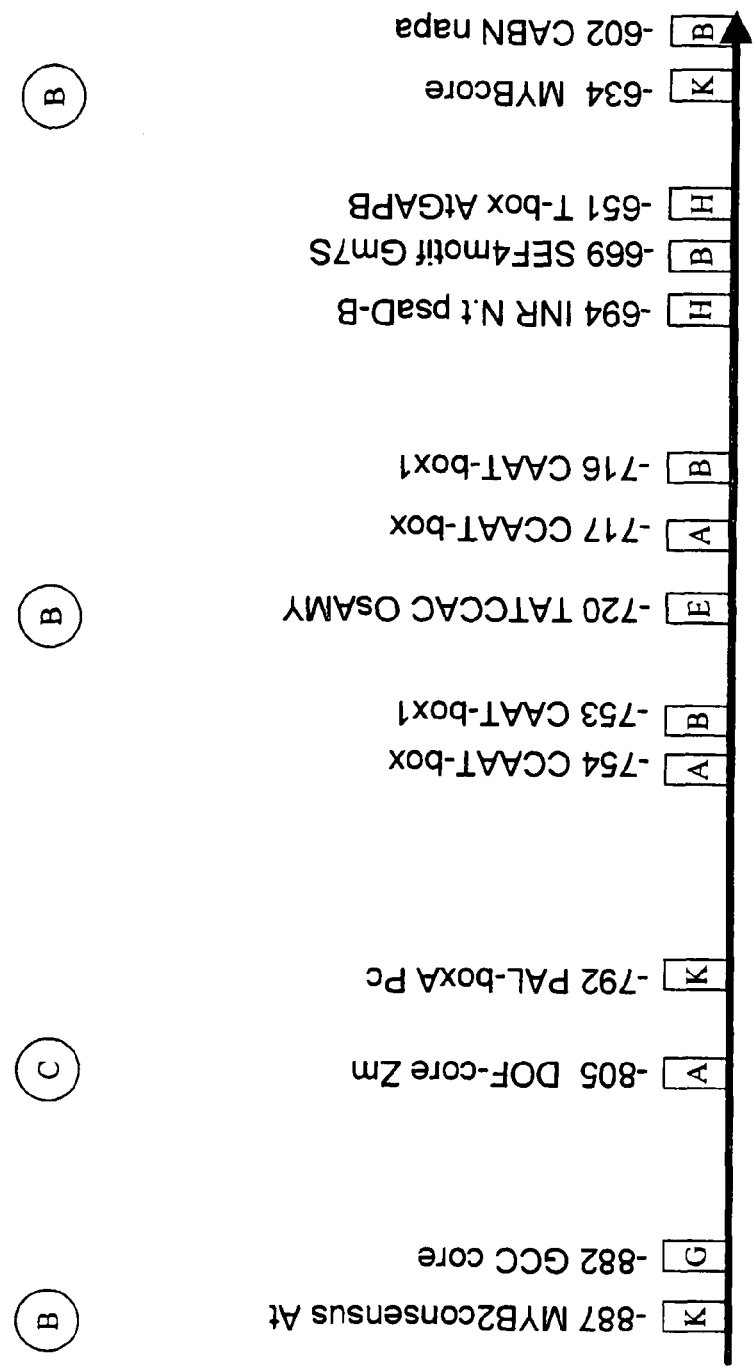
FIG. 7A is a graph showing the results of expression regulatory-element analysis of the SiGT8 gene.
Figure 7B:
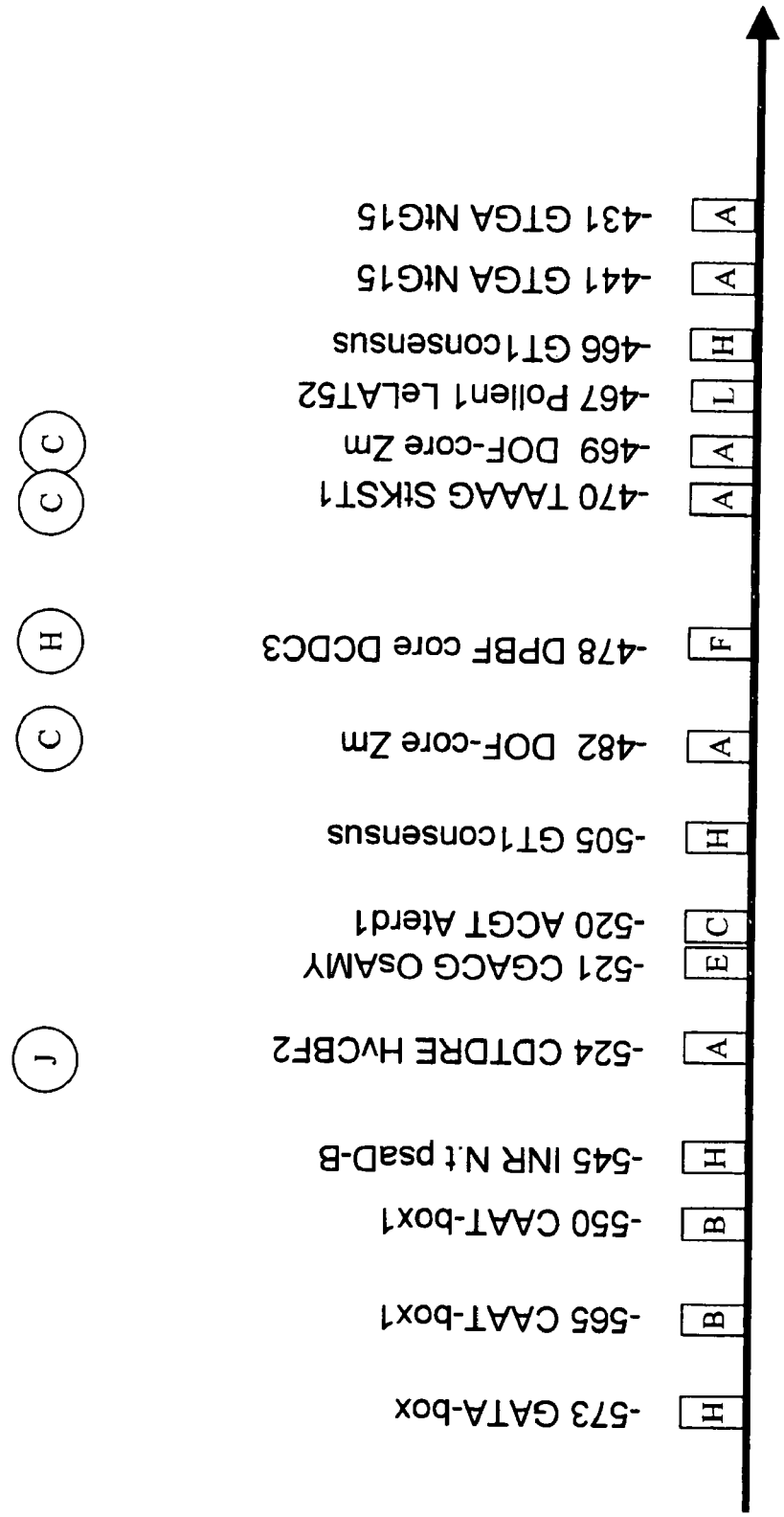
FIG. 7B continues from FIG. 7A and is a graph showing the results of expression regulatory-element analysis of the SiGT8 gene.
Figure 7C:
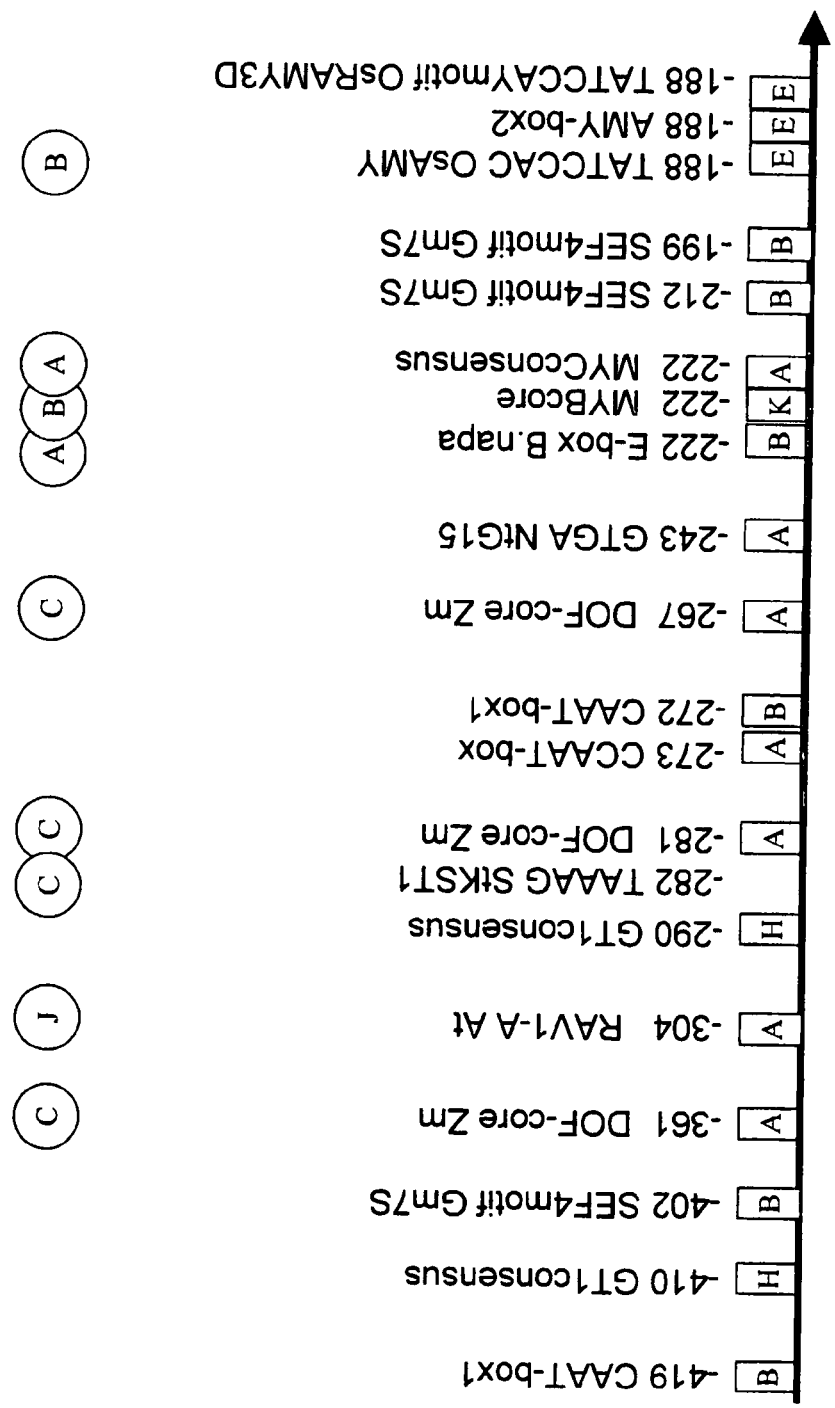
FIG. 7C continues from FIG. 7B and is a graph showing the results of expression regulatory-element analysis of the SiGT8 gene.
Figure 7D:
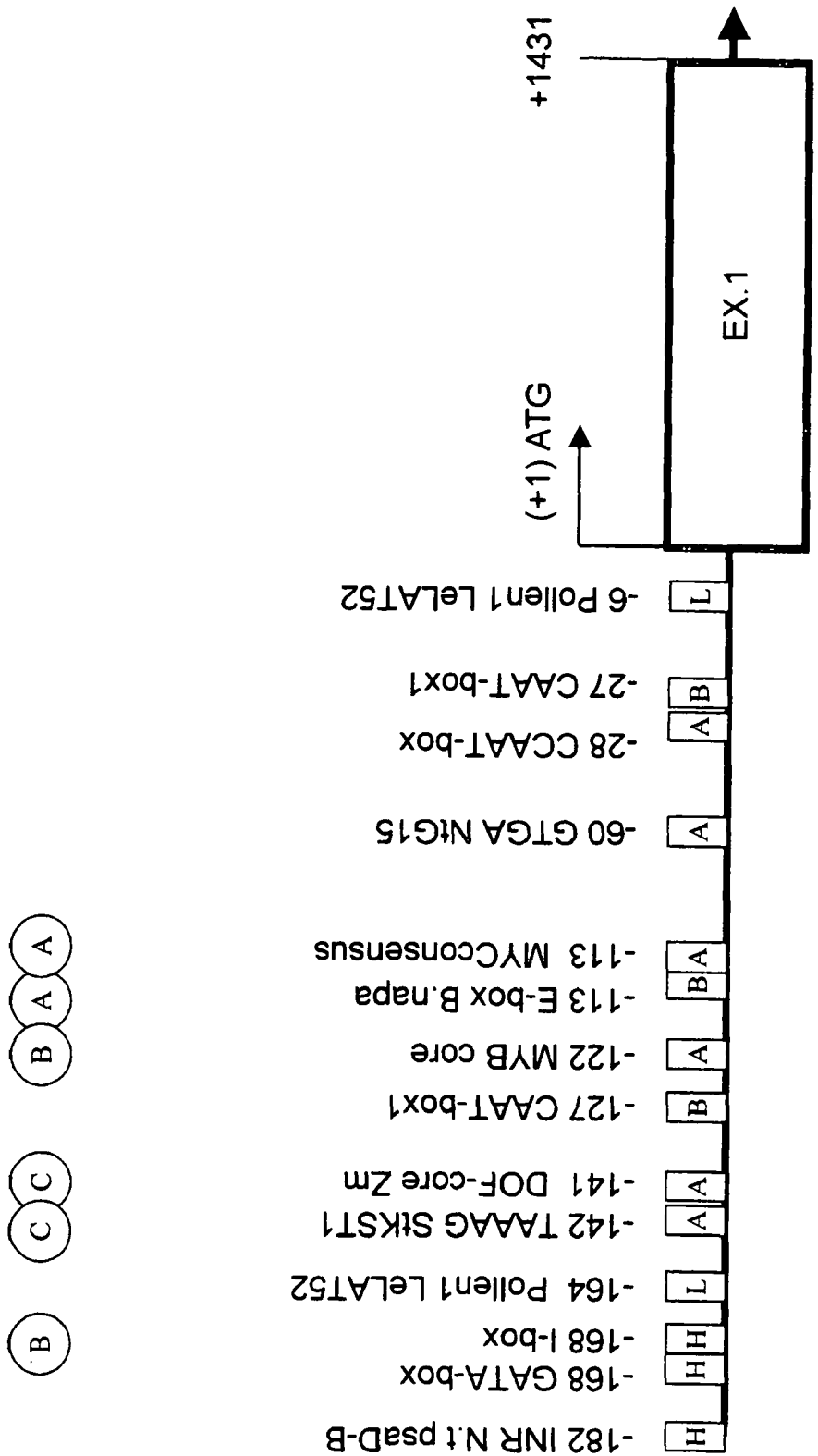
FIG. 7D continues from FIG. 7C and is a graph showing the results of expression regulatory-element analysis of the SiGT8 gene.
Figure 8A:
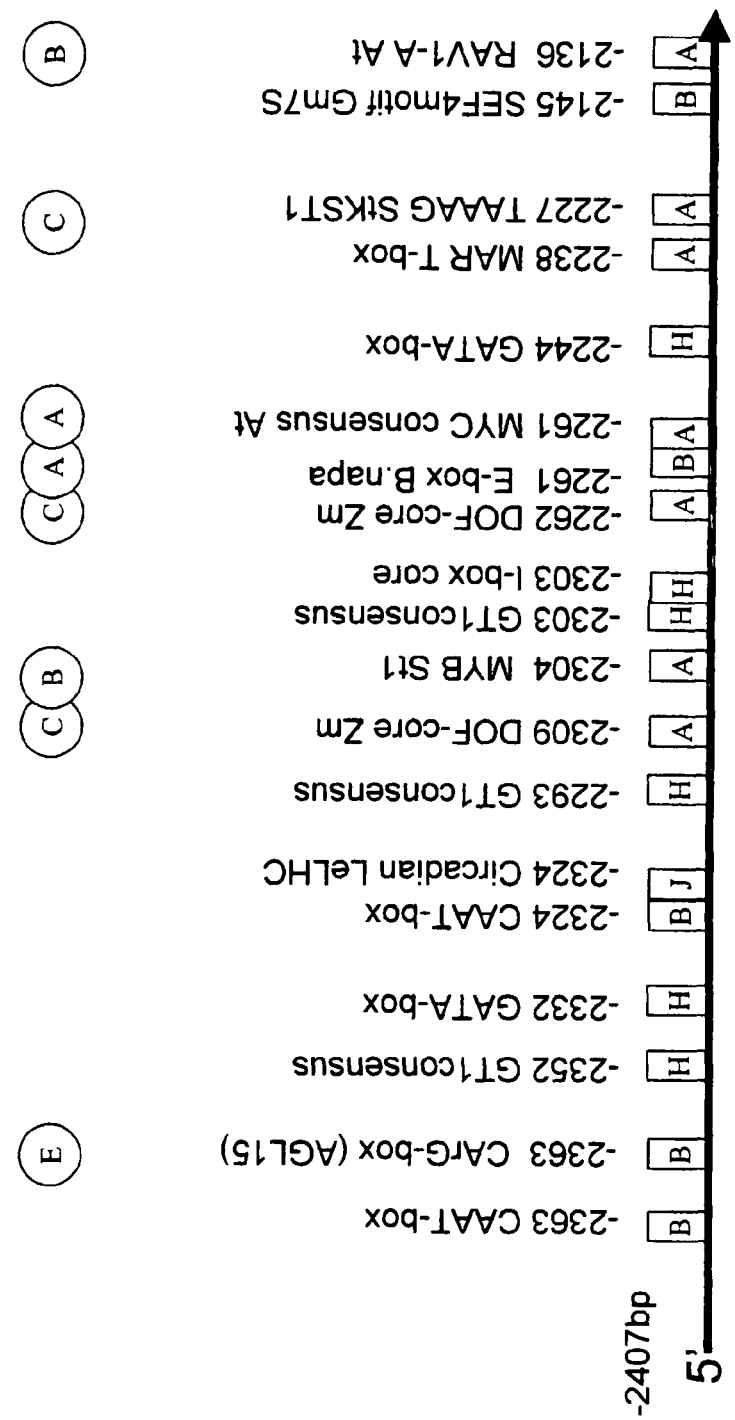
FIG. 8A is a graph showing the results of expression regulatory-element analysis of the SiGT10 gene.
Figure 8B:
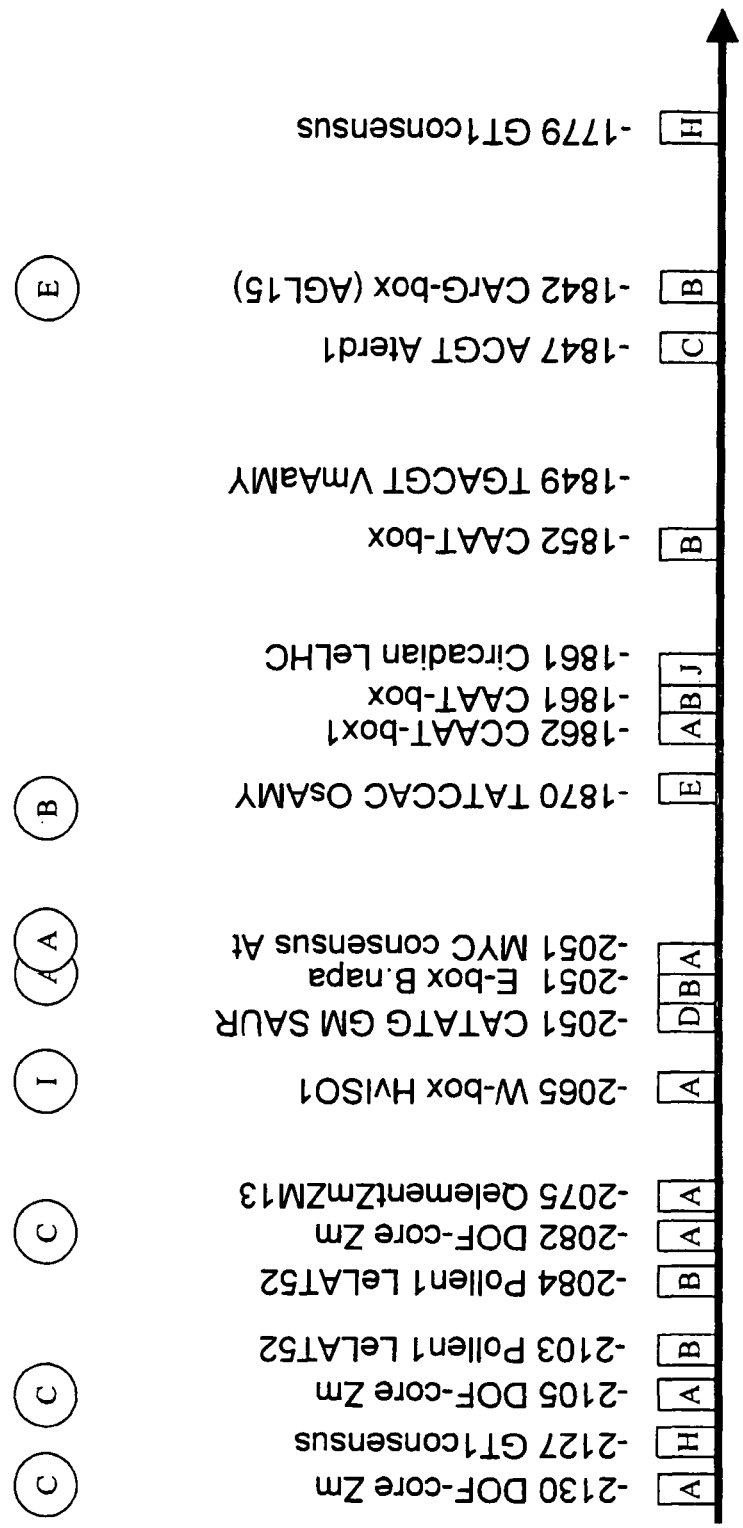
FIG. 8B continues from FIG. 8A and is a graph showing the results of expression regulatory-element analysis of the SiGT10 gene.
Figure 8C:
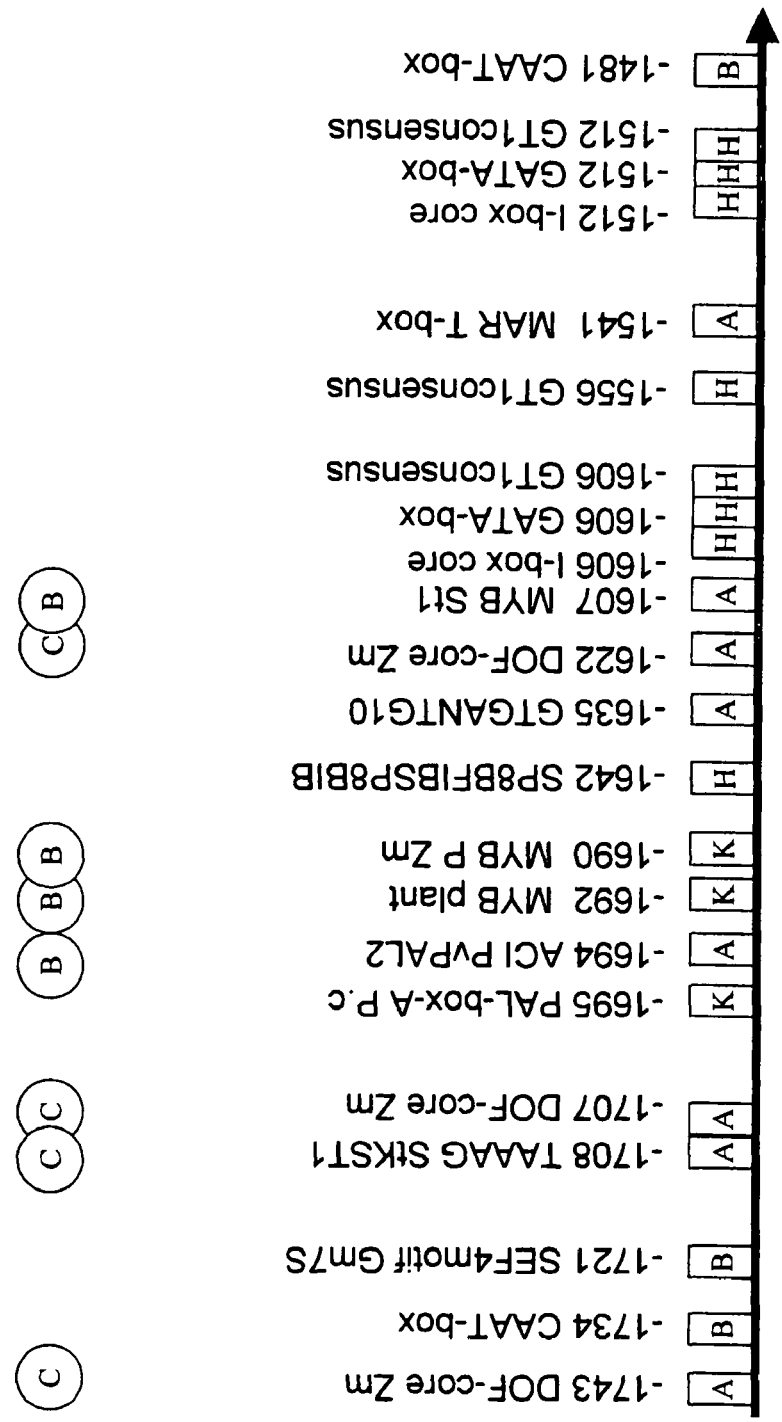
FIG. 8C continues from FIG. 8B and is a graph showing the results of expression regulatory-element analysis of the SiGT10 gene.
Figure 8D:
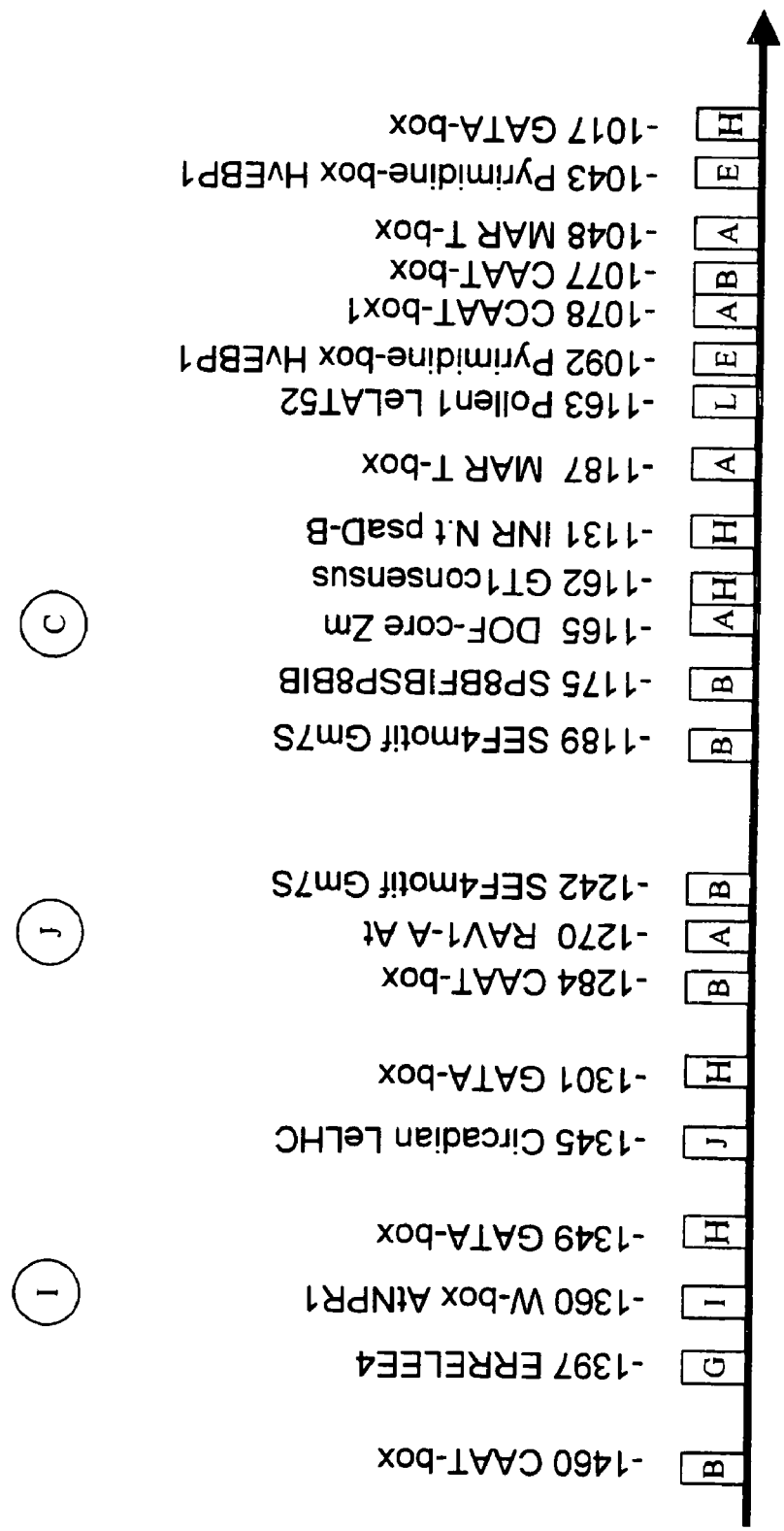
FIG. 8D continues from FIG. 8C and is a graph showing the results of expression regulatory-element analysis of the SiGT10 gene.
Figure 8E:
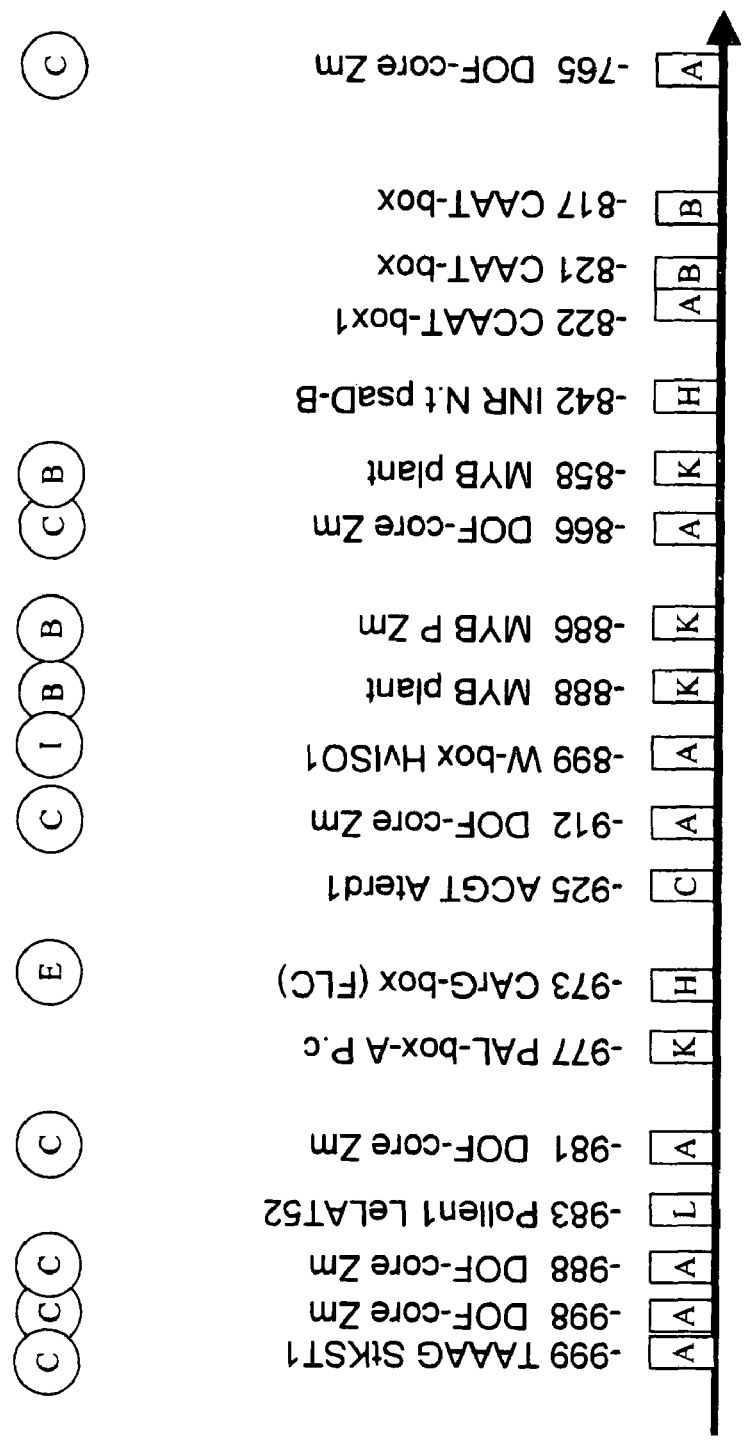
FIG. 8E continues from FIG. 8D and is a graph showing the results of expression regulatory-element analysis of the SiGT10 gene.
Figure 8G:
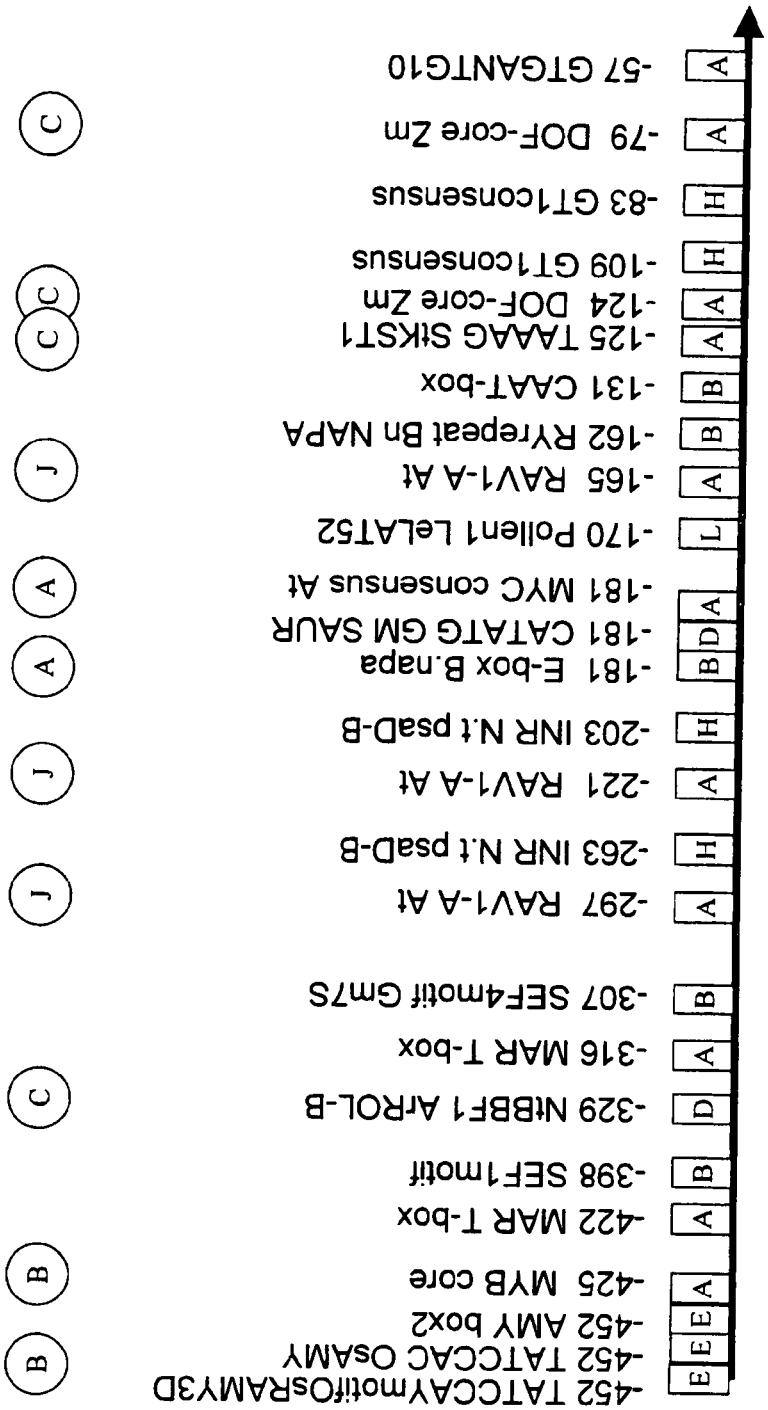
FIG. 8G continues from FIG. 8F and is a graph showing the results of expression regulatory-element analysis of the SiGT10 gene.
Figure 8H:
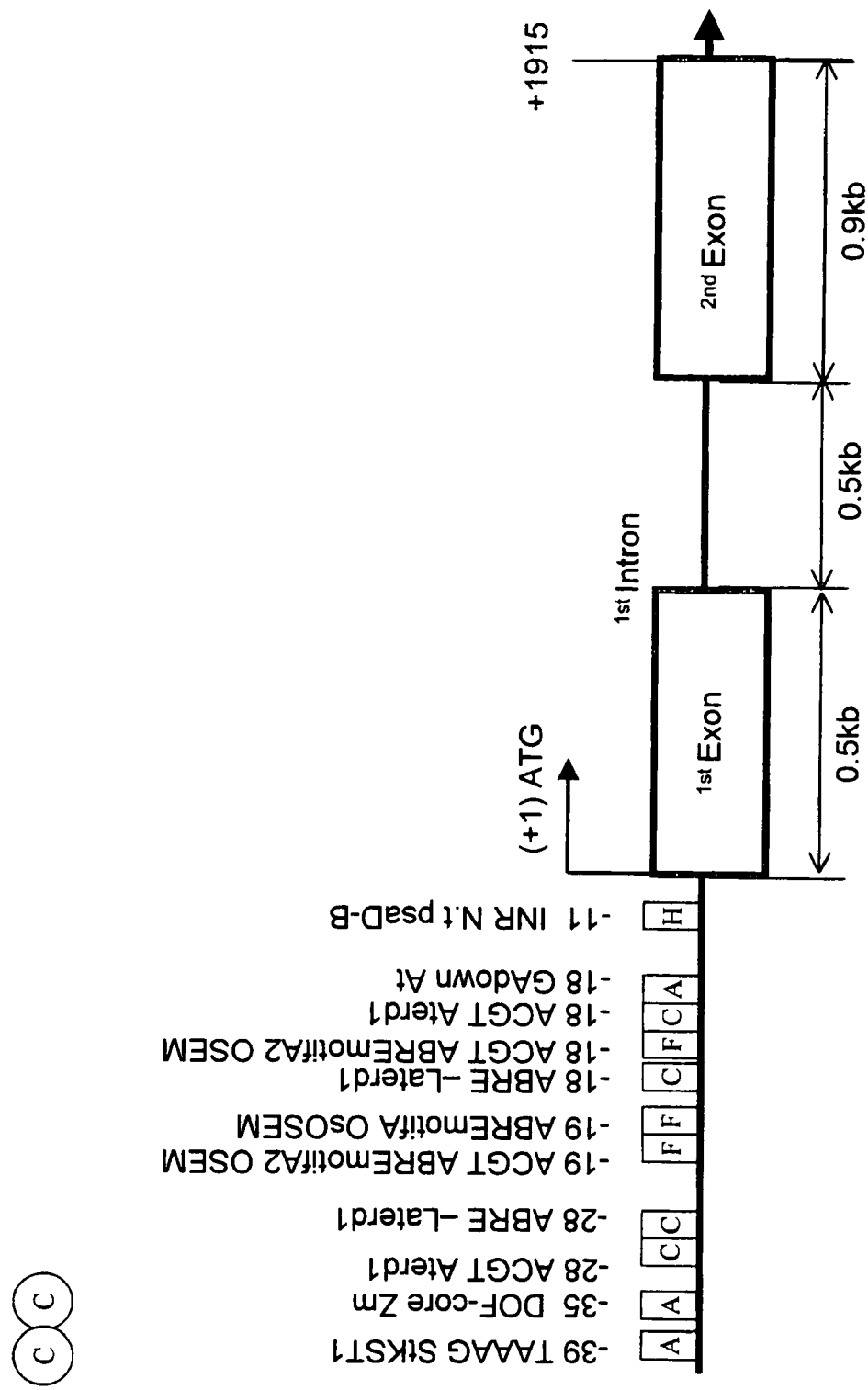
FIG. 8H continues from FIG. 8G and is a graph showing the results of expression regulatory-element analysis of the SiGT10 gene.

As a result of HPLC analysis, any peak with a spectrum for any new lignan was detected in the reaction solution of the SrSiGT8 recombinant protein and pinoresinol. However, peak E having a new spectrum for lignan showing the retention time of about 7.4 minutes was detected in the reaction solution of the SrSiGT8 recombinant protein and piperitol (FIG. 6C). In addition, peak F having a new spectrum for lignan showing the retention time of about 8.2 minutes was detected in the reaction solution of the SiGT8 recombinant protein and sesaminol (FIG. 6D). These products shown by peaks E and F were not produced when UDP-glucose was removed from the enzyme reaction solution (FIG. 6G and FIG. 6H), strongly suggesting that they would be the lignan glycosides added as the substrates. Peak E coincided in retention time with peak D for piperitol glycoside shown in EXAMPLE 8, and was found to be the monoglucoside of piperitol. Peak F coincided in retention time with peaks B and C in EXAMPLE 8, and was found to be the monoglucoside of sesaminol.

The foregoing results revealed that SrSiGT8 isolated from *Sesamum radiatum* had the activity to transfer sugars to lignans.

Example 12

Identification of Expression Regulatory Region of SiGT8 and SiGT10

In order to examine the mechanism of expression regulation of the SiGT8 gene and SiGT10 gene, genomic clones of these genes were isolated.

Genomic DNA library (ca. 250,000 pfu) derived from domesticated sesame (*S. indicum*) was screened using about 1.4 kb (SiGT8 probe) of ORF region in the SiGT8 gene amplified by the primer consisting of the base sequence represented by SEQ ID NO: 75 and the primer consisting of the base sequence represented by SEQ ID NO: 76 or about 1.4 kb (SiGT10 probe) of ORF region in the SiGT10 gene amplified by the primer consisting of the base sequence represented by SEQ ID NO: 77 and the primer consisting of the base sequence represented by SEQ ID NO: 78. Sesame genomic library was prepared from domesticated sesame (*S. indicum*) genomic DNA using λBlueSTAR™ Vector system (NOVAGEN).

First, 200 μg of sesame genomic DNA was partially digested with restriction enzyme Sau3AI to about 20 kb in fragment size, followed by 10-40% sucrose density gradient centrifugation at 10° C. at 25000 rpm for 24 hours (SW28 rotar, Beckman). The centrifuged sample was fractionated by 1 ml each using AUTOMATIC LIQUID CHARGER (Advantech) and Micro Tube Pump (EYELA). The fragment size of the fractionated sample was confirmed by pulse field electrophoresis. Pulse field electrophoresis was performed in 0.5× TBE buffer (CHEF MAPPER, Invitrogen) under the conditions of 120°/1 sec.-1 sec. and 6 V/cm, using a gel composed of 1% Agarose NA (Amersham bioscience) and 0.5×TBE. Using fractions containing an average fragment size of about 20 kb, genomic library was prepared according to the protocol recommended by the manufacturer. The library prepared had a titer of 1.5×10$^6$ pfu/500 μl.

After the secondary screening, 5 positive clones were acquired, respectively, by the SiGT8 probe and the SiGT1 probe. Next, PCR was carried out on these positive clones, using the primer consisting of the base sequence represented by SEQ ID NO: 76 or the primer consisting of the base sequence represented by SEQ ID NO: 78 and STAR-LF1 (SEQ ID NO: 83) and STAR-LR1 (SEQ ID NO: 84), which were phage arm primers, determine a positional relationship to the SiGT8 gene or to the SiGT10 gene.

```
                                          (SEQ ID NO: 83)
STAR-LF1: 5'-acgaagttatgcggccaattaaccc-3'

(SEQ ID NO: 84)
STAR-LR1: 5'-ccacctgacgtcgcggcctaatacg-3'.
```

The results suggested that the SiGT8-positive clone gSiGT8#13 contained about 1 kb of 5' gene expression regulatory region. On the other hand, it was suggested that the SiGT10-positive clone gSiGT10#37 contained about 1.5 kb of 5' gene expression regulatory region.

Next, using the phage of gSiGT8#13 or gSiGT10#37 as the template, the inserted fragment was amplified by LA-PCR using a combination of T7 primer (SEQ ID NO: 85) and the primer consisting of the base sequence represented by SEQ ID NO: 76 or the primer consisting of the base sequence represented by SEQ ID NO: 78. A phage solution comprised of 1 μl or 1×LA-PCR buffer (TaKaRa), 0.2 mM dNTPs, 2.5 mM MgCl$_2$, 0.2 μmol/μl of each primer and 1.25 U of LA-Taq polymerase. After reacting at 94° C. for 5 minutes, 32 cycles of the reaction at 94° C. for 1 minute, 53° C. for 1 minute and 72° C. for 4 minutes was carried out, and finally maintained at 72° C. for 7 minutes.

```
T7: 5'-taatacgactcactataggg-3'.    (SEQ ID NO: 85)
```

Electrophoresis of the fragments obtained gave the amplified fragments of about 2.4 kb and about 3.0 kb, respectively. These fragments were inserted into the multicloning site of pCR-XL-TOPO vector (Invitrogen) according to the protocol recommended by the manufacturer to give pSPB2659 and pSPB2660.

The full-length base sequence of the fragment inserted into pSPB2659 was determined by the primer walking method to obtain the base sequence predicted to contain the 5' expression regulatory region of SiGT8 gene.

```
gSiGT8#13:
                                          (SEQ ID NO: 86)
ACTAGTAACGGCCGCCAGTGTGCTGGAATTCGCCCTTGTAATACGACTCA

CTATAGGGCGACCGCGGATCTTCACTATCACTACTTCAAAGGACGGGCAA

CCGTCCGCATCCGCTACTTATCGTCCTGATCGATTATACCAATTCTTATT

GAGGATCGGGTTCCACAAATACTATCCAATTTAATTTTTTATCTGCTTTT

CACTTTTTTTATAAATATTATTTATTTTTAATTTTTCTACAACTTTGAAC

TTTCTCTGTTAAAATGATTTACCTAAAATTAAAATTTTCCCAAACACTCC

TAGTATGTCAGAATCTTTTGATATCTACAATAGATTGAATTACAATTTTC

ACTCTATTATTATAAGGCGTCGACGTTTATTGTTCTAGGAAAATAAAATC

TGGTACCTAAAAAGACACTAGTTAAAGAAAAATAAAAATTGGTAGATTGA

AGTGAATTTCTGTGAAGATTCTACAATTTGCTGGAAATTGATTTTTGATT

TGGGATTTTATATGTTGGTTATTTAAACTGAAAAGTGGAGCATTTCATCA

TTCATGTTTTGCTTAATTGGATTGCATATAGGTCTGATCAACATGTTTTG

TCGGAAAATTTAAAGTTTCCCAATCAAAGATTGATTGGCCCAGCTTTCGG

TGAAATTTGTCGTCAGCTCGCAGTTGAATTGTTTTTAATTACTGTTTTTA

ATATTATCCATTCATTTTTTACAAGATAAGAAATGTCATTTCCTTATTTG

TAAAGGATCAAATTGCAATTAAACCATCTCAAATGCATAGCATTACACGC

CTGCGTATGTGTATGTCTGATCTCAAGAATCAGTGAGACTCTTGTGTCAT

ATCGTCTTTCCCTTCCAATTTCCTGAATTCAGCACCAGAAAAC.
```

In order to identify the expression regulatory element located upstream at the 5' end of this SiGT8 gene, the sequence shown by SEQ ID NO: 86 was subjected to the PLACE analysis (HYPERLINK "http://www.dna.affrc.go.jp/PLACE/" http://www.dna.affrc.go.jp/PLACE/). By the PLACE analysis, many expression regulatory elements in response to the specific binding sites of transcription factor family and specific signals present in the SiGT8 promoter were identified, suggesting that these expression regulatory elements would affect expression of the SiGT8 gene (FIG. 7).

The full-length base sequence of the fragment inserted into pSPB2660 was determined by the primer walking method to obtain the base sequence predicted to contain the 5' expression regulatory region of SiGT10 gene.

gSiGT10#37:

(SEQ ID NO: 87)
AATTTATGTAATAGACAGTGTCAATTTGGATTGTTTGTTATAAATTTGAA

AACATGATTAATTCAAATTATGTTCTATCAAATTAAAATTATTTATTTGA

CAGACATGATACAAATTTATCTATAGGTATAGGATTGTTATATATTATTC

ATAATGATATTTGTCATGTAATCAATTAATTAATTTCAACATAAAACTTG

TGTAATTGGATCTTGTTTTTAATTTTTTCTTAAATTAAAATATATAAATT

GCGTGTATATAGTATTTATTTTTATTATTTATACTATTACAAAAGAAAAT

TTATTGATCCCATTTTACTTTTTCGTTCATTTTATTTTGTTTTTTAATTA

TTTTATAATTACATTTTTTTCCTCTCACCCAATACTCCATTTCTCTTTCT

CATGTTCTTTATATTTTTTCCTCTCACAAATATGAAATAGATAGTTTAGA

GGTAGTTTAAAGCAGCATAAAGTAGAAAGCCGTCCTATTTAGGTTGTTGG

AATTGAAGGAGGAAGGAAGGGCAAATCCATTACGTCAGTCAAAAAAAGAA

GCTTTTATGACTGATGAACACCAACCGGTCTACCAGGAGCAAAGAGCTCA

CCTAACCTAGAGAATTCACTCCCTGGATGTAAGTCCAATCAATCAGTAGC

GGTAGAATAGTCCGATTTCCTAGCTTCGGAAGCCCTCTCGAAAAGCCCCC

TTCCAATGACCCTAAGCGCTAAAATCAACCCTTGTAATGTCACTGAACGA

AAGTCTTAGAGCAGTAATAAGGAACACAACAAACCCAACAACAAAATCGG

CTAGGCTGAGTTTGAAAGTTGCGATTTTCGATACGTTTTTCCTTTTTTGT

AAAAAAGAGAAAAATCCCTGTAGATAGAGATCCGCTTCTCTAGATGGCCC

GGCGTACAGCCCTACATTTCTCAATTCACAACAAGACCTCTGAGAAAAAG

AATTTAGATCGAGUCGTCGAAGCGAGCTTAGCAACCCTAAGCGAAGTCTT

CCCCTATCCATAATTTTAATAAATCCTATTACAGTTATTTTTTCTCTCA

CATTTATCATATTTATTTTTCGTACAAATTTTCATATTTTTAATGAACT

CTAAATTGTAATTCTTTCGTCTTTTTTACTTTATCCCATATTTTTTTTT

ATCACCTCACAACATTATGTGTTTTTCTATAATATTTTTTTCTTCATTT

CACAGTATAATTTTTCATATATATAATTGCATAAACAACATATATTTTTT

CTCTTCATTTCATAGTATAATTTTTCATATGATCGCAGAAACAACATGCA

ACGACCACTAATAAAAATAATGAATCAATATTAAAGTGCTAAAACATGAA

AATTGTAGTGGAGTTGTTGAAGTGGAAAAAGCCACACACACTGAAGTAGG

TGAAGACCAAACTGTATAAATAAAGGTTACGTGTTGCTACGTGTCTTCAC

TCTTCAC.

Further in order to identify the expression regulatory element located upstream at the 5' end of this SiGT10 gene, the gSiGT-seq-RV4 primer (SEQ ID NO: 88) extending toward upstream at the 5' end was designed based on the base sequence of SEQ ID NO: 87. Using this primer and T7 primer (SEQ ID NO: 85), LA-PCR was performed using as templates the 5 positive clones obtained by the genomic screening of SiGT10. The conditions for LA-PCR were as given above. gSiGT-seq-RV4: 5'-gaagacttcgcttagggttgctaa-3' (SEQ ID NO: 88).

Electrophoresis of the fragment obtained gave the amplified fragment of about 2.0 kb when the gSiGT10#43 clone was used as the template. This fragment was then inserted into the multicloning site of pCR-TOPO-XL vector (Invitrogen) according to the protocol recommended by the manufacturer to give pSPB2662.

The full-length base sequence of the fragment inserted into pSPB2662 was determined by the primer walking method and ligated to the previously identified fragment (SEQ ID NO: 87) to obtain the base sequence predicted to contain the 5' expression regulatory region of SiGT10 gene.

gSiGT10#43:

(SEQ ID NO: 89)
GTAATACGACTCACTATAGGGGGACCGCGGATCATATTTTTTTCAATAAA

ATGTGAAAAATATAAAAAATTATTGATAGGGGCAATTTTATCTATACAAA

GAGGATAAATATTGAAAATGCATAAAAAAAAAATCATTTCATTCGCATGT

GCAGTGCGTGTAGATATATTTTTTTTTTATAAAGAGAATCTTTTTTACAG

ACATTTATAATTACATAATGTCTGTCTTGATTATTTAATTAATACAAGTA

AGTATTTAATAATTTTTGTACAACACAAAGGTAATATGTAATTTTCCATA

AAAAGAAATAAGACAAAATCGGAGAAAGGTTAGGTCATGGCTGACTTCAC

ATATACATATGTCTTAATCGGATTAGACGCTGCCGGCTCTTACTTTTCGA

ATTCCTCACATATACATATATGTCTTGAATTTGGACCATCTTACCAGACA

TAAATCGGATTTGTCGCCGGCGGCTCTTACTTTTCGAATTCTGTGTAACT

CACATTCAAACTTATTAATTTGTACACTAATATATTTATCCAGGCCAATT

AAATCAATGACGTACTATAAAATGATTACATAATTATATTTCTTAAAATT

TGTAAATATATTATAATTAATTAAAATGAAAATTTTGTGTTTGTCCACCA

CCTTTGCAAATACAAAGACGAACAATAGCGTTCCGGTTTTTGTTCATGTA

AAGTGTCAAGTCCCCACCTACCTCATCACTCATTAATCTTGTCATTTCTT

TTGCCCCTACTTGCTACTATTGTGATTATATACAAAAGACTATATTTATG

GATAATTTACATATACTTTTATGGACTATGTTCTAACTTATAATAATGCT

GGAAATCTAAACTTTTTATTTTATTTTCTTTTCTTTTTGTATATGATAAA

TATGCTCTTGCAGTCTTTACTTCCTCAATCACATTATTAGTTCGGTCAAT

AATTTATGTAATAGACAGTGTCAATTTGGATTGTTTGTTATAAATTTGAA

AACATGATTAATTCAAATTATGTTCTATCAAATTAAAATTATTTATTTGA

CAGACATGATACAAATTTATCTATAGGTATAGGATTGTTATATATTATTC

ATAATGATATTTGTCATGTAATCAATTAATTAATTTCAACATAAAACTTG

TGTAATTGGATCTTGTTTTTAATTTTTTCTTAAATTAAAATATATAAATT

GCGTGTATATAGTATTTATTTTTATTATTTATACTATTACAAAAGAAAAT

TTATTGATCCCATTTTACTTTTTCGTTCATTTTATTTTGTTTTTTAATTA

TTTTATAATTACATTTTTTTCCTCTCACCCAATACTCCATTTCTCTTTCT

CATGTTCTTTATATTTTTTCCTCTCACAAATATGAAATAGATAGTTTAGA

GGTAGTTTAAAGCAGCATAAAGTAGAAAGCCGTCCTATTTAGGTTGTTGG

AATTGAAGGAGGAAGGAAGGGCAAATCCATTACGTCAGTCAAAAAAAGAA

GCTTTTATGACTGATGAACACCAACCGGTCTACCAGGAGCAAAGAGCTCA

CCTAACCTAGAGAATTCACTCCCTGGATGTAAGTCCAATCAATCAGTAGC

GGTAGAATAGTCCGATTTCCTAGCTTCGGAAGCCCTCTCGAAAAGCCCCC

TTCCAATGACCCTAAGCGCTAAAATCAACCCTTGTAATGTCACTGAACGA

AAGTCTTAGAGCAGTAATAAGGAACACAACAAACCCAACAACAAAATCGG

CTAGGCTGAGTTTGAAAGTTGCGATTTTCGATACGTTTTTCCTTTTTTGT

-continued

```
AAAAAAGAGAAAAATCCCTGTAGATAGAGATCCGCTTCTCTAGATGGCCC
GGCGTACAGCCCTACATTTCTCAATTCACAACAAGACCTCTGAGAAAAAG
AATTTAGATCGAGGCGTCGAAGCGAGCTTAGCAACCCTAAGCGAAGTCTT
CCCCTATCCATAATTTTAATAAATCCTATTACAGTTATTTTTTCTCTCA
CATTTATCATATTTATTTTTTCGTACAAATTTTCATATTTTTAATGAACT
CTAAATTGTAATTCTTTCGTCTTTTTTACTTTATCCCATATTTTTTTTT
ATCACCTCACAACATTATGTGTTTTTCTATAATATTTTTTTTCTTCATTT
CACAGTATAATTTTTCATATATATAATTGCATAAACAACATATATTTTTT
CTCTTCATTTCATAGTATAATTTTTCATATGATCGCAGAAACAACATGCA
ACGACCACTAATAAAAATAATGAATCAATATTAAAGTGCTAAAACATGAA
AATTGTAGTGGAGTTGTTGAAGTGGAAAAAGCCACACACACTGAAGTAGG
TGAAGACCAAACTGTATAAATAAAGGTTACGTGTTGCTACGTGTCTTCAC
TCTTCAC.
```

As in the SiGT8 gene described above, the sequence shown by SEQ ID NO: 89 was subjected to the PLACE analysis. By the PLACE analysis, many expression regulatory elements in response to the specific binding sites of transcription factor family and specific signals present in the SiGT10 promoter were identified, suggesting that these expression regulatory elements would affect expression of the SiGT10 gene (FIG. 8).

The full-length ORF of SiGT10 was contained in the inserted fragment of pSPB2660. The base sequencing revealed that in SiGT10, one intron of 525 bp was present at the site of 497 bp downstream at the 3' end from the initiation codon. The full-length ORF of SiGT8 was contained in the fragment inserted into pSPB2659 but no intron was identified by the base sequencing.

Based on the foregoing results, the SiGT8 gene and the SiGT10 gene both encode the enzyme to transfer sugars to lignans but the results of alignment on the Clustal W alignment (Mac Vector ver. 7.2.2, Symantec Corporation) indicate that the sequence identity in ORF between the two genes was as low as 42% on the DNA level and 22% on the amino acid level, and the gene structures were also different depending upon the intron insertion. Phrased differently, the results indicate that in the enzymes having the activity to transfer sugars to lignans, the sequence identity and the conserved gene structure do not necessarily harmonize with the function of enzyme. More specifically, sequence information of the SiGT8 gene could be used to clone its counterpart gene, i.e., the SrSiGT8 gene from *Sesamum radiatum* but it is easy to suppose that it is extremely difficult to isolate the SrSiGT1 gene. By first demonstrating clearly the two lignan glycosyltransferases having low sequence homology, the present invention disclosed for the first time that at least two lignan glycosyltransferases function in sesame.

Example 13

Isolation of SiGT8-Like Gene from *S. alatum*

*S. alatum* is a sesame species native of Africa and, also in a morphological aspect significantly, differs from domesticated *S. indicum* (Namiki et al., "Goma-no-Kagaku" (Science of Sesame), Asakura Publishing Co.). The chromosome number is the same 2n=26 as in *S. indicum*, and geographically verified in Nigeria, Sudan and Mozambique of Africa.

The counterpart gene (SaSiGT8) of SiGT8 from *S. alatum* was isolated using the procedures as in EXAMPLE 4. In a manner similar to EXAMPLE 4, cDNA was prepared from the seeds of *S. alatum* and PCR was performed as in EXAMPLE 11 to give the amplified fragment of 1.4 kb. This amplified fragment was subcloned onto pCR-TOPO-blunt4 (Invitrogen) to give pSPB2697. The base sequence of the 1.4 kb insert into pSPB2697 was determined by primer walking. The base sequence of SaSiGT8 is shown by SEQ ID NO: 90 and the amino acid sequence of SaSiGT8 is shown by SEQ ID NO: 91.

SaSiGT8:
(Base sequence)
(SEQ ID NO: 90)
```
ATGTCGGCGGACCAAAAATTAACCAGCCTAGTCTTCGTTCCTTTCCCTAT
AATGAGTCACCTGGCAACAGCAGTGAAGACGGCGAAGCTCCTGGCCGACA
GAGACGAACGCCTCTCGATCACAGTCCTCGTGATGAAGCTACCAATTGAT
ACGCTGATCAGTTCTTACACTAAGAACTCGCCTGACGCCCGAGTAAAAGT
AGTCCAACTGCCCGAAGACGAGCCCACCTTTACAAAGCTGATGAAATCTT
CCAAGAACTTCTTCTTTCGATACATCGAGAGCCAGAAAGGCACTGTCAGG
GACGCTGTGGCTGAGATTATGAAGAGTTCGAGGTCGTGTAGGCTTGCAGG
ATTTGTAATCGACATGTTCTGCACAACCATGATTGATGTCGCCAACGAGC
TTGGAGTCCCGACTTACATGTTCTTCAGTTCGGGTTCAGCAACGCTCGGG
CTCATGTTCCATCTCCAGAGTCTCAGAGATGACAATAATGTGGACGTCAT
GGAGTACAAGAATTCAGATGCTGCGATATCAATACCCACATACGTTAACC
CCGTTCCTGTTGCGGTATGGCCTTCCCAGGTGTTTGAGGAGGACAGTGGT
TTCCTTGACTTTGCCAAAAGGTTTAGAGAAACCAAAGGGATTATTGTGAA
CACATTCCTCGAATTCGAAACCCACCAGATTAGGTCATTGTCTGATGACA
AGAAAATCCCACCAGTTTATCCTGTGGGGCCAATACTTCAAGCTGATGAG
AACAAAATTGAGCAGGAAAAGGAAAAGCACGCGGAAATCATGAGGTGGCT
CGACAAGCAACCTGATTCTTCTGTAGTGTTTCTTTGCTTTGGTACGCATG
GATGTTTGGAAGGGGATCAGGTGAAGGAGATTGCTGTGGCCCTGGAAAAC
AGTGGACATCGGTTTTTGTGGTCCCTGAGGAAGCCGCCTCCGAAAGAAAA
GGTTGAGTTTCCAGGAGAGTATGAGAATTCAGAAGAAGTTTTACCAGAAG
GGTTCCTGGGACGAACTACTGACATGGGTAAAGTTATCGGATGGGCGCCT
CAAATGGCAGTGTTATCTCACCCTGCGGTGGGAGGATTTGTGTCGCACTG
TGCGTGGAACTCTGTGTTGGAAAGTGTGTGGTGTGGGGTGCCGATGGCCG
TGTGGCCGTTGTCTGCAGAGCAGCAGGCCAATGCATTCTTGCTAGTAAAG
GAGTTTGAAATGGCAGTTGAGATTAAGATGGATTATAAGAAAAATGCTAA
CGTGATTGTGGGCACAGAGACGATAGAGGAAGCAATCAGACAGCTAATGG
ACCCAGAGAATGAAATTCGGGTTAAGGTGAGAGCATTGAAAGAAAAGAGC
AGAATGGCCCTAATGGAAGGAGGGTCTTCGTACAATTACTTGAAACGTTT
CGTCGAGAATGTCGTGAATAACATTTCTTGA.
```

-continued (Amino acid sequence (SaSiGT8))
(SEQ ID NO: 91)
MSADQKLTSLVFVPFPIMSHLATAVKTAKLLADRDERLSITVLVMKLPID

TLISSYTKNSPDARVKVVQLPEDEPTFTKLMKSSKNFFFRYIESQKGTVR

DAVAEIMKSSRSCRLAGFVIDMFCTTMIDVANELGVPTYMFFSSGSATLG

LMIFHLQSLRDDNNVDVMEYKNSDAAISIPTYVNPVPVAVWPSQVFEEDS

GFLDFAKRFRETKGIIVNTFLEFETHQIRSLSDDKKIPPVYPVGPILQAD

ENKIEQEKEKHAEIMRWLDKQPDSSVVFLCFGTHGCLEGDQVKEIAVALE

NSGHRFLWSLRKPPPKEKVEFPGEYENSEEVLPEGFLGRTTDMGKVIGWA

PQMAVLSHPAVGGFVSHCGWNSVLESVWCGVPMAVWPLSAEQQANAFLLV

KEFEMAVEIKMDYKKNANVIVGTETIEEAIRQLMDPENEIRVKVRALKEK

SRMALMEGGSSYNYLKRFVENVVNNIS.

The SaSiGT8 obtained showed 98% sequence identity to the SiGT8 gene derived from S. indicum and 92% sequence identity to the SrSiGT8 gene derived from S. radiatum, in the amino acid level. In addition to this high sequence identity, SaSiGT8 was expressed in the seed. Since it was thus predicted that SaSiGT8 would retain the lignan glycosidation activity, it was next analyzed if the activity of recombinant SaSiGT8 protein was conserved.

Figure 9:
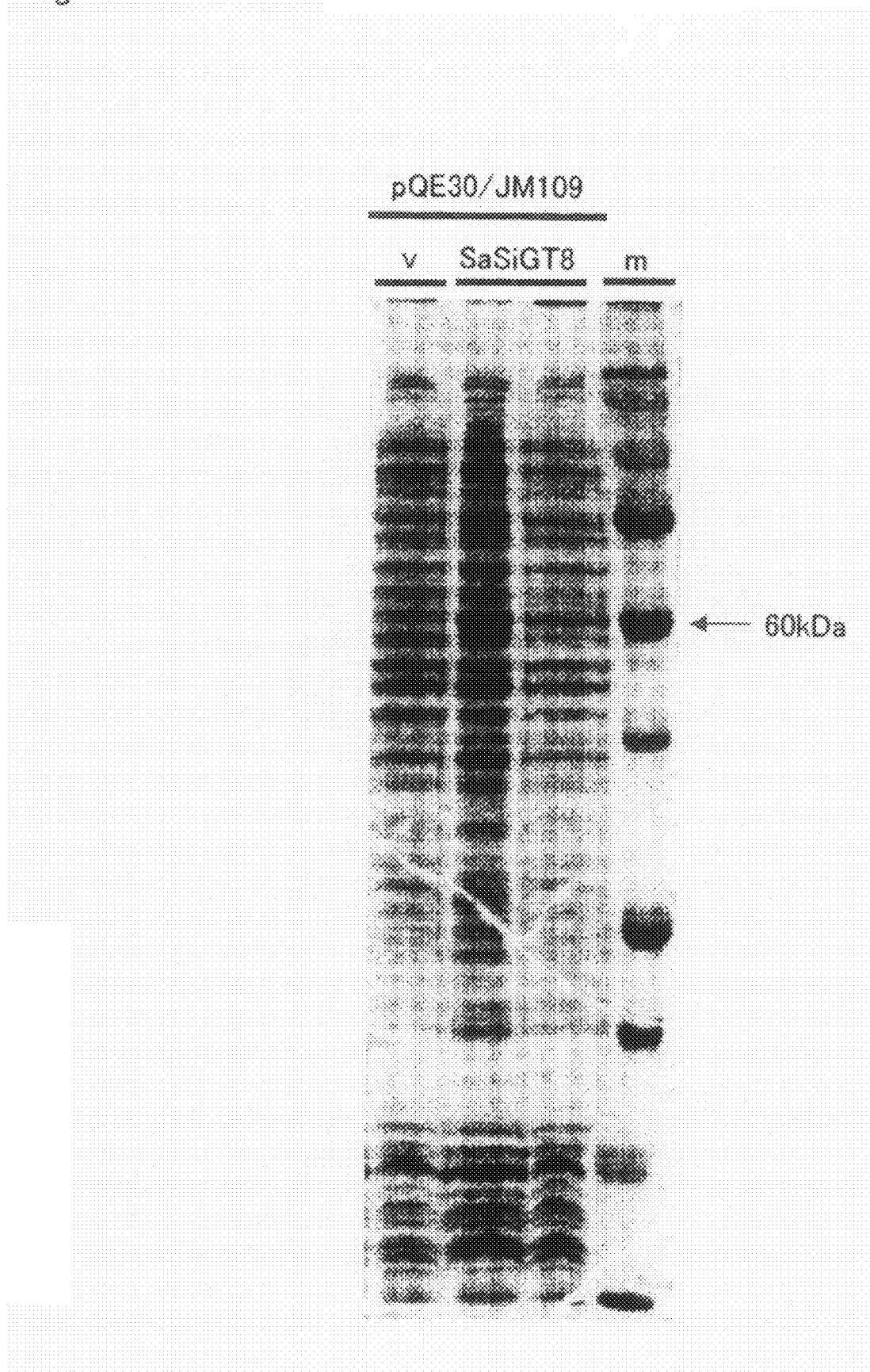
FIG. 9 is a photograph showing gels stained with CBB after recombinant SaSiGT8 protein (SaLGT1) was applied on SDS-PAGE.
Figure 10A:
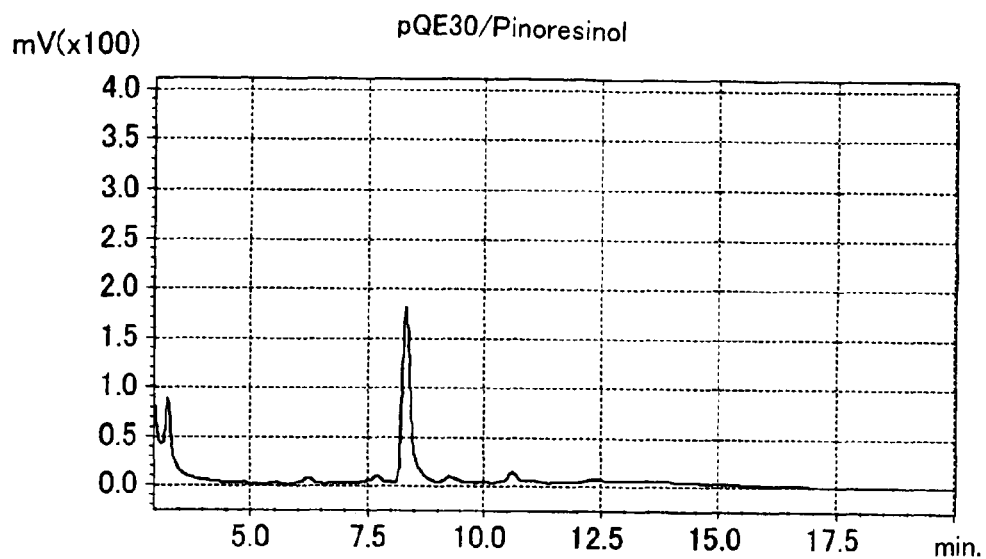
FIG. 10A is graphs showing the pinoresinol glycosidation activity in cells wherein only an empty vector for producing SaSiGT8 recombinant protein (SaLGT1) was introduced and in cells wherein an expression vector was introduced.
Figure 10A:
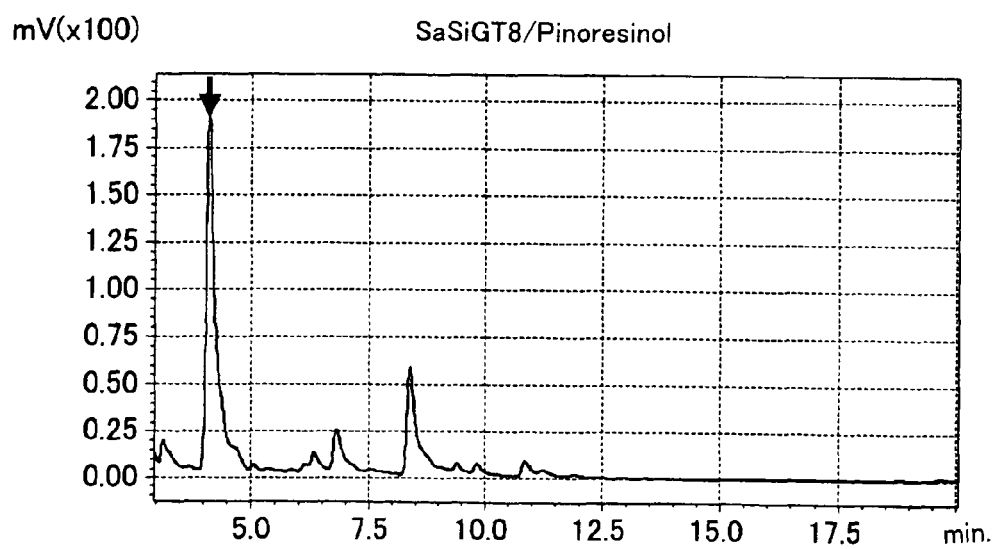
Figure 10B:
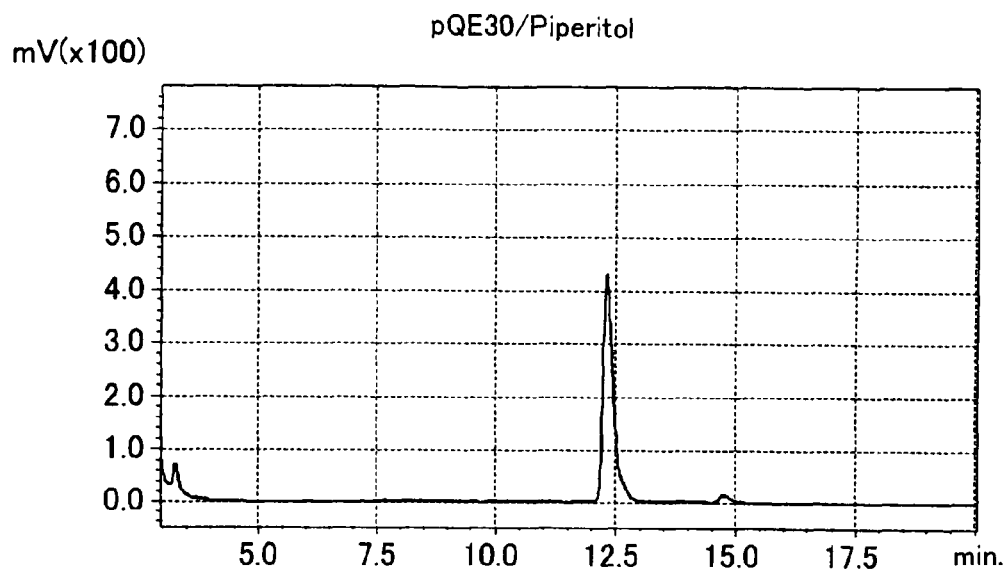
FIG. 10B is graphs showing the piperitol glycosidation activity in cells wherein only an empty vector for producing SaSiGT8 recombinant protein (SaLGT1) was introduced and in cells wherein an expression vector was introduced.
Figure 10B:
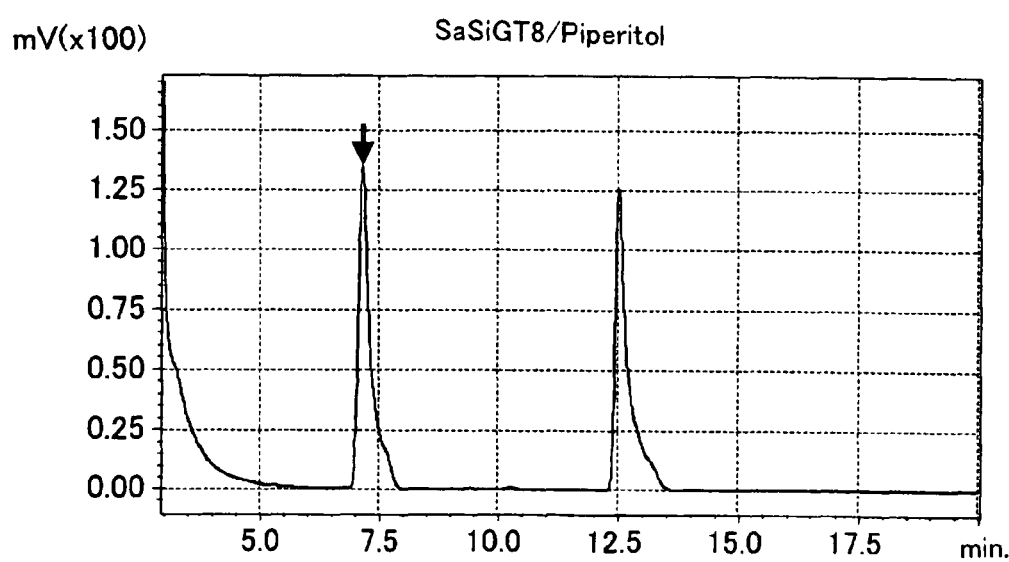
Figure 10C:
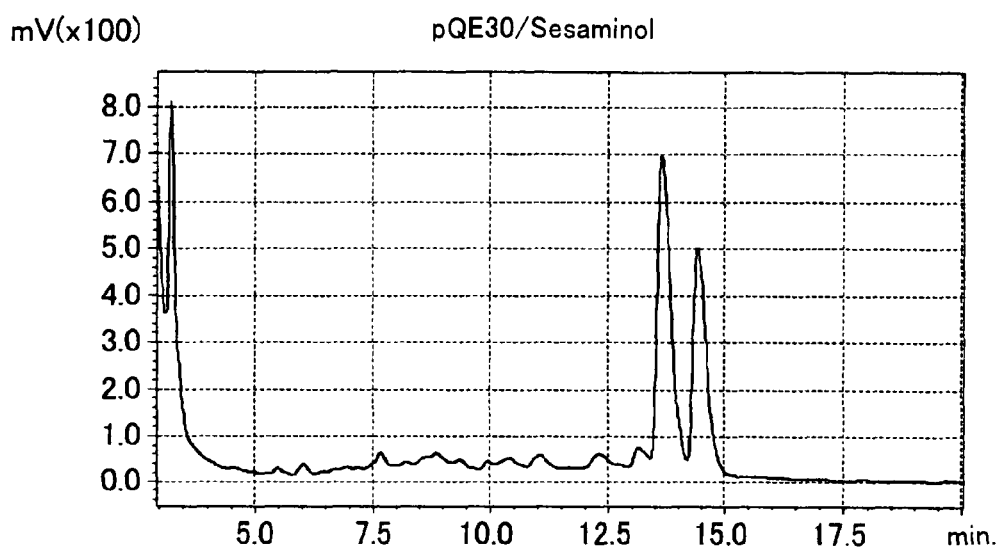
FIG. 10C is graphs showing the sesaminol glycosidation activity in cells wherein only an empty vector for producing SaSiGT8 recombinant protein (SaLGT1) was introduced and in cells wherein an expression vector was introduced.
Figure 10C:
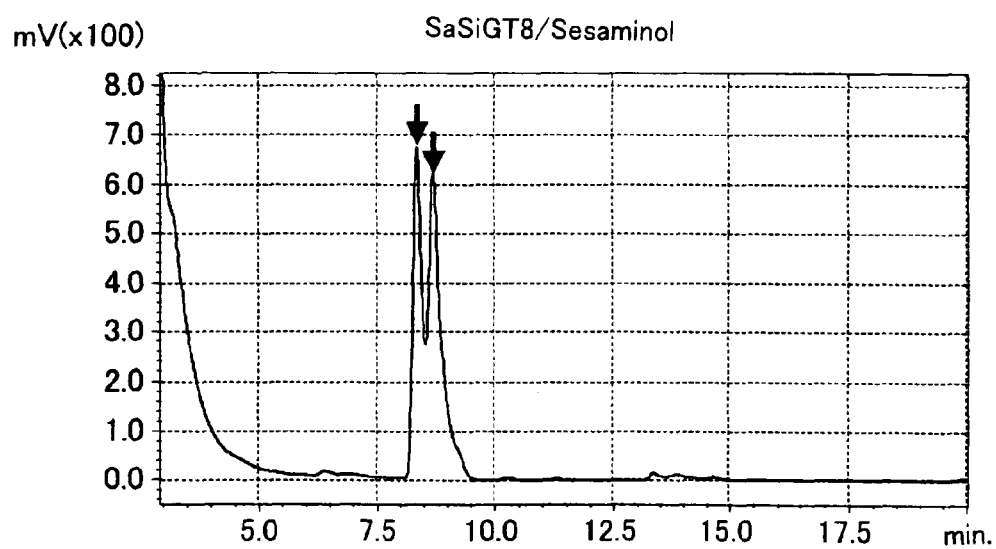
Figure 10D:
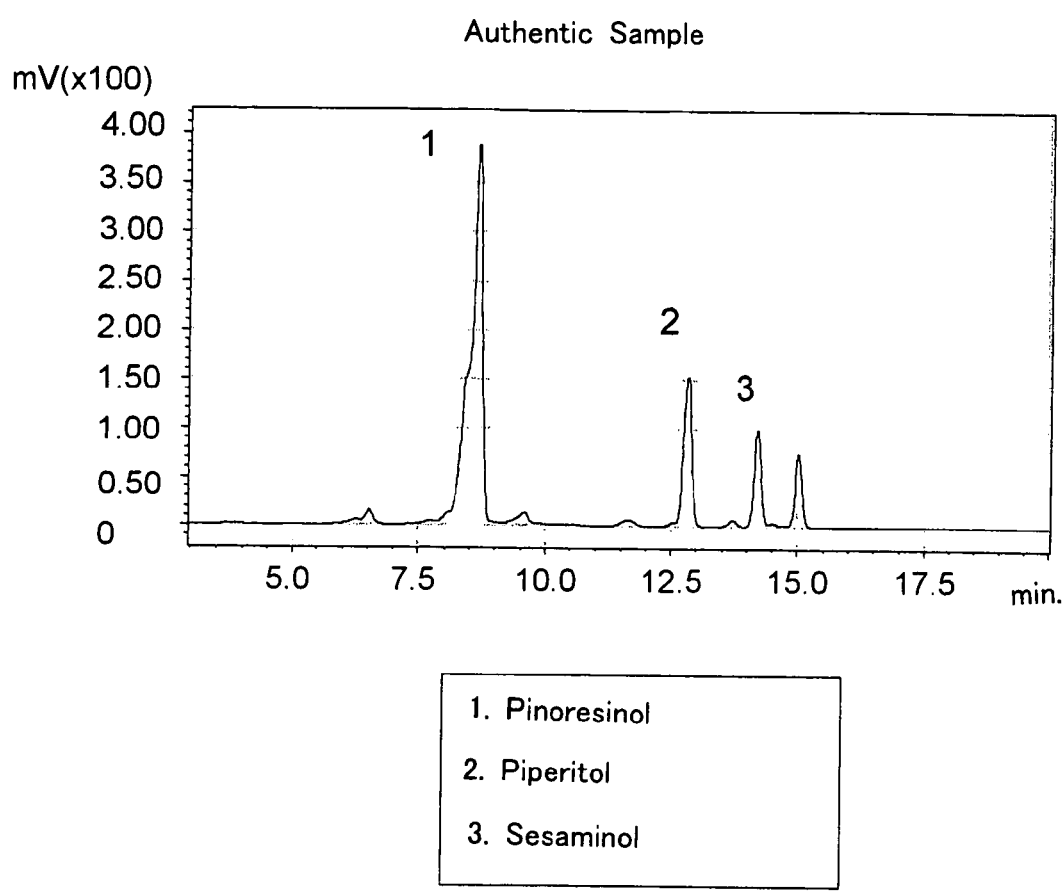
FIG. 10D shows peaks of various authentic lignans.

The fragment containing ORF of SaSiGT8 was excised from pSPB2697 with BamHI and KpnI and inserted into the BamHI and KpnI sites of Escherichia coli expression vector pQE30 to give the expression vector pSPB2698. The recombinant SaSiGT8 protein (SaLGT1) was expressed as in EXAMPLE 11 to confirm that the protein had the lignan glycosidation activity. It was also confirmed by SDS-PAGE that the recombinant SaSiGT8 protein (ca. 60 kDa) was present in the lysis supernatant of transgenic Escherichia coli expressing the SaSiGT8 gene (FIG. 9).

As a result of the HPLC analysis (FIG. 10), the SaSiGT8 recombinant protein produced the respective monoglucosides showing retention times of about 4, 7.4 and 8.2 minutes in the reaction solutions of pinoresinol, piperitol and sesaminol, as in the SiGT8 recombinant protein.

The foregoing results demonstrated that SaSiGT8 encode the lignan glycosidases as in SiGT8. The results further demonstrated that the SrSiGT8 and SaSiGT8 genes showing high sequence identity to SiGT8 isolated from S. radiatum and S. alatum are functionally conserved throughout the evolutionary process.

The present invention is not limited to the embodiments described above but it is intended to cover various modifications that are within the scope defined by the claims. That is, embodiments obtained by suitable combinations of technical means suitably arranged within the scope defined by the claims are also included in the technical scope of the present invention

INDUSTRIAL APPLICABILITY

As described above, the polypeptide and polynucleotide in accordance with the present invention are useful in producing lignan glycosides. Also, the transformant or cell, in which the polynucleotide in accordance with the present invention is introduced to be capable of expressing the same, is extremely useful in producing lignan glycosides or products using the same, in the food sector and a variety of industry sectors. Where the transformant above is a plant, the plant itself can be used as foodstuffs and is thus very useful in the agriculture sector, etc.

Moreover, by using the polypeptide and polynucleotide in accordance with the present invention in combination with the other enzymes (piperitol and sesamin synthase SiP189) discovered by the present inventors, the production system of not only sesame but also particular lignan molecular species can be established so that the production volumes of particular lignan and lignan glycosides can be expanded. Accordingly, the present invention is widely utilized in agriculture, food industry and drug industry as well as industries related thereto.

The invention claimed is:

1. An isolated polynucleotide encoding a polypeptide having a lignan glycosidation activity, which is either (a) or (b):
   (a) a polynucleotide consisting of the nucleotide sequence of any one of SEQ ID NO: 1, 81, or 90; or
   (b) a polynucleotide consisting of a nucleotide sequence which has at least 90% sequence identity to SEQ ID NO: 1, 81, or 90.

2. A vector comprising the polynucleotide of claim 1.

3. A method for producing a polypeptide having lignan glycosidation activity, which comprises:
   (a) transforming a host cell with the vector of claim 2;
   (b) culturing the host cell; and
   (c) isolating the polypeptide from the cell culture.

4. An isolated host cell transformed with the polynucleotide of claim 1.

5. The host cell-according to claim 4, wherein content ratios of lignan and a lignan glycoside are modified.

6. A method for producing a polypeptide having lignan glycosidation activity, which comprises culturing the host cell of claim 4 and isolating the polypeptide from the cell culture.

7. An isolated cell comprising the vector according to claim 2.

8. The isolated polynucleotide of claim 1, wherein in (b) the polynucleotide consists of a nucleotide sequence which has at least 95% sequence identity to SEQ ID NO: 1, 81, or 90.

* * * * *

SEQUENCE LISTING

<160> NUMBER OF SEQ ID NOS: 91

<210> SEQ ID NO 1
<211> LENGTH: 1431
<212> TYPE: DNA
<213> ORGANISM: Sesamun indicum

<400> SEQUENCE: 1

```
atgtcggcgg accaaaaatt aaccagccta gtcttcgttc ctttccctat aatgagtcac      60
ctggcaacag cagtgaagac ggcgaagctc ctggccgaca gagacgaacg cctctcaatc     120
acagtcctcg tgatgaagct accaattgat acgctgatca gttcttacac taagaactcg     180
cctgacgccc gagtaaaagt agtccaactg cccgaagacg agcccacctt tacaaagctg     240
atgaaatctt ccaagaactt cttctttcga tacatcgaga gccagaaagg cactgtcagg     300
gacgctgtgg ctgagattat gaagagttcg aggtcgtgta ggattgcagg atttgtaatc     360
gacatgttct gcacacccat gattgatgtc gctaacgagc ttggagtccc gacttacatg     420
ttcttcagtt cgggttcagc aacgctcggg ctcatgttcc atctccagag tctcagagat     480
gacaataatg tggacgtgat ggagtacaag aattcagatg ctgcgatttc aatacccaca     540
```

-continued

```
tacgttaacc cgttcctgt tgcggtatgg ccttccccag tgtttgagga ggacactggt    600
ttccttgact tcgccaaaag gtttagagaa accaaaggga ttattgtgaa cacattcctc    660
gagttcgaaa cccaccagat taggtcattc tctgatgata agaaaatccc accagtttat    720
cctgtggggc caatacttca agctgatgag aacaaaattg agcaggaaaa ggaaaagcac    780
gcggaaatca tgaggtggct cgacaagcaa cctgattctt ctgtagtgtt tctttgcttt    840
ggtacgcatg gatgtttgga aggggatcag gtgaaggaga ttgctgtggc cctggaaaac    900
agtggacatc ggttttttgtg gtccctgagg aagccgcctc cgaaagaaaa ggttgagttt    960
ccaggagagt atgagaattc agaagaagtt ttaccagaag ggttcctggg acgaactact   1020
gacatgggta agttatcgg atgggcgcct caaatggcag tgttatctca ccctgcggtg    1080
ggaggatttg tgtcgcactg tgggtggaac tctgtgttgg aaagtgtgtg gtgtggggtg   1140
ccgatggccg tgtggccgtt gtctgcagag cagcaggcca atgcattctt gctagtaaag   1200
gagtttgaaa tggcagttga gattaagatg gattataaga aaaatgctta cccgattgtg   1260
ggcacagaga cgatagagga agcaatcaga cagctaatgg acccagagaa tgaaattcgg   1320
gttaaggtga gagcattgaa agaaaagagc agaatggccc taatggaagg agggtcttcg   1380
tacaattact tgaaacgttt cgtcgagaat gtcgtgaata acatttcttg a             1431
```

<210> SEQ ID NO 2
<211> LENGTH: 476
<212> TYPE: PRT
<213> ORGANISM: Sesamun indicum

<400> SEQUENCE: 2

```
Met Ser Ala Asp Gln Lys Leu Thr Ser Leu Val Phe Val Pro Phe Pro
  1               5                  10                  15

Ile Met Ser His Leu Ala Thr Ala Val Lys Thr Ala Lys Leu Leu Ala
             20                  25                  30

Asp Arg Asp Glu Arg Leu Ser Ile Thr Val Leu Val Met Lys Leu Pro
         35                  40                  45

Ile Asp Thr Leu Ile Ser Ser Tyr Thr Lys Asn Ser Pro Asp Ala Arg
     50                  55                  60

Val Lys Val Val Gln Leu Pro Glu Asp Glu Pro Thr Phe Thr Lys Leu
 65                  70                  75                  80

Met Lys Ser Ser Lys Asn Phe Phe Arg Tyr Ile Glu Ser Gln Lys
                 85                  90                  95

Gly Thr Val Arg Asp Ala Val Ala Glu Ile Met Lys Ser Ser Arg Ser
            100                 105                 110

Cys Arg Ile Ala Gly Phe Val Ile Asp Met Phe Cys Thr Pro Met Ile
        115                 120                 125

Asp Val Ala Asn Glu Leu Gly Val Pro Thr Tyr Met Phe Phe Ser Ser
    130                 135                 140

Gly Ser Ala Thr Leu Gly Leu Met Phe His Leu Gln Ser Leu Arg Asp
145                 150                 155                 160

Asp Asn Asn Val Asp Val Met Glu Tyr Lys Asn Ser Asp Ala Ala Ile
                165                 170                 175

Ser Ile Pro Thr Tyr Val Asn Pro Val Pro Val Ala Val Trp Pro Ser
            180                 185                 190

Pro Val Phe Glu Glu Asp Thr Gly Phe Leu Asp Phe Ala Lys Arg Phe
        195                 200                 205

Arg Glu Thr Lys Gly Ile Ile Val Asn Thr Phe Leu Glu Phe Glu Thr
    210                 215                 220
```

```
His Gln Ile Arg Ser Phe Ser Asp Asp Lys Lys Ile Pro Pro Val Tyr
225                 230                 235                 240

Pro Val Gly Pro Ile Leu Gln Ala Asp Glu Asn Lys Ile Glu Gln Glu
            245                 250                 255

Lys Glu Lys His Ala Glu Ile Met Arg Trp Leu Asp Lys Gln Pro Asp
        260                 265                 270

Ser Ser Val Val Phe Leu Cys Phe Gly Thr His Gly Cys Leu Glu Gly
    275                 280                 285

Asp Gln Val Lys Glu Ile Ala Val Ala Leu Glu Asn Ser Gly His Arg
290                 295                 300

Phe Leu Trp Ser Leu Arg Lys Pro Pro Lys Glu Lys Val Glu Phe
305                 310                 315                 320

Pro Gly Glu Tyr Glu Asn Ser Glu Glu Val Leu Pro Glu Gly Phe Leu
            325                 330                 335

Gly Arg Thr Thr Asp Met Gly Lys Val Ile Gly Trp Ala Pro Gln Met
            340                 345                 350

Ala Val Leu Ser His Pro Ala Val Gly Gly Phe Val Ser His Cys Gly
    355                 360                 365

Trp Asn Ser Val Leu Glu Ser Val Trp Cys Gly Val Pro Met Ala Val
370                 375                 380

Trp Pro Leu Ser Ala Glu Gln Gln Ala Asn Ala Phe Leu Leu Val Lys
385                 390                 395                 400

Glu Phe Glu Met Ala Val Glu Ile Lys Met Asp Tyr Lys Lys Asn Ala
            405                 410                 415

Tyr Pro Ile Val Gly Thr Glu Thr Ile Glu Glu Ala Ile Arg Gln Leu
            420                 425                 430

Met Asp Pro Glu Asn Glu Ile Arg Val Lys Val Arg Ala Leu Lys Glu
            435                 440                 445

Lys Ser Arg Met Ala Leu Met Glu Gly Gly Ser Ser Tyr Asn Tyr Leu
    450                 455                 460

Lys Arg Phe Val Glu Asn Val Val Asn Asn Ile Ser
465                 470                 475

<210> SEQ ID NO 3
<211> LENGTH: 1389
<212> TYPE: DNA
<213> ORGANISM: Sesamun indicum

<400> SEQUENCE: 3
atggcgccgg cggcgagaac cgacccaatc atgacatgcc acgtggtggc cgtcccttat        60
cccggcaggg gccacgtcaa ccccatgatg aacctctgca agctactcac caattccaag       120
cccgatctcc tcatcaccgt cgtagtcacg gaggagtggc tcggcatcat cggctccgag       180
gagaagccgc aggtatttg cttcgcctcc atcccgaacg tcttgccgtc ggagttggtt       240
cgcgcctccg acatgccgac cttcgtgggg gctacccaga ctaagatgga ggagccgttt       300
gagctgctgc tcgaccggct cgacgcgccg gttaattta taattgccga tacgttcttg       360
tactgggcgg ttgaggttgg gaagcggagg aatattccgg tagcgtcact ctggccgatg       420
cccgcatcgg tgttctcggt attttaccat tttgatctcc tcgaacggaa cggccatcac       480
cccttcgaat atctgaaag aggggaagaa cgagtggagt acatccctgg aatcccttcg       540
attcgtttgg cggatactcc ctcccttgcc cacatgaagg atcaacgact gcttcgtcta       600
gtccgtagaa ttttccaaa cgtatccaag gcacaatatc tgttgattc ttccatcttt       660 gagctagaac acaagttat agaagctctg aagcaagaat tctcattccc tgtacacacg       720
```

-continued

```
tttggccctg ccatacctta cttcaatctc agaaaagcta cttctttctt gactagtcag    780
aatgatcacg accatcacta ttttgagtgg ttgaactctc aacctccatg ttcggttcta    840
tatgtgtcgt tgggaagctt cctctcggtt tcaagtgccc aaatggatga atttgctgat    900
ggattgcgta aaagtggcgt taggttcttg tgggtggctc gtggggaggc cacgaggctg    960
caagaacgat gtggggacgt ggggagagtg gtgccttggt gtgagcagct gaaggtgttg   1020
tgccactcgt cggttggtgg attctggaca cactgcgggt ggaattcgac gatggaagct   1080
atttttgctg gtgtgccggt aatagctttt cctctaacaa tggatcagac caccatccgt   1140
aagcatgttg ttgaggactg gaagatgggg tgggatgcta agaaagggtt ggaggctggg   1200
aatttgttga ggagtgcgag aattgctgag cttgttaaga agttgatgga tttggaatgc   1260
gtcgagcgga aggagatcgc tgcgagggct aaagaactgc agaaggtgac tttacaagca   1320
gtttcagaag gagggtcgtc caaggcgaat ctcacttctt tcctcgatga tattgcatcg   1380
tttagctga                                                          1389
```

<210> SEQ ID NO 4
<211> LENGTH: 462
<212> TYPE: PRT
<213> ORGANISM: Sesamun indicum

<400> SEQUENCE: 4

```
Met Ala Pro Ala Ala Arg Thr Asp Pro Ile Met Thr Cys His Val Val
  1               5                  10                  15

Ala Val Pro Tyr Pro Gly Arg Gly His Val Asn Pro Met Met Asn Leu
             20                  25                  30

Cys Lys Leu Leu Thr Asn Ser Lys Pro Asp Leu Leu Ile Thr Val Val
         35                  40                  45

Val Thr Glu Glu Trp Leu Gly Ile Ile Gly Ser Glu Glu Lys Pro Pro
     50                  55                  60

Gly Ile Cys Phe Ala Ser Ile Pro Asn Val Leu Pro Ser Glu Leu Val
 65                  70                  75                  80

Arg Ala Ser Asp Met Pro Thr Phe Val Gly Ala Thr Gln Thr Lys Met
                 85                  90                  95

Glu Glu Pro Phe Glu Leu Leu Leu Asp Arg Leu Asp Ala Pro Val Asn
            100                 105                 110

Phe Ile Ile Ala Asp Thr Phe Leu Tyr Trp Ala Val Glu Val Gly Lys
        115                 120                 125

Arg Arg Asn Ile Pro Val Ala Ser Leu Trp Pro Met Pro Ala Ser Val
    130                 135                 140

Phe Ser Val Phe Tyr His Phe Asp Leu Leu Glu Arg Asn Gly His His
145                 150                 155                 160

Pro Phe Glu Leu Ser Glu Arg Gly Glu Glu Arg Val Glu Tyr Ile Pro
                165                 170                 175

Gly Ile Pro Ser Ile Arg Leu Ala Asp Thr Pro Ser Leu Ala His Met
            180                 185                 190

Lys Asp Gln Arg Leu Leu Arg Leu Val Arg Arg Ile Phe Pro Asn Val
        195                 200                 205

Ser Lys Ala Gln Tyr Leu Leu Ile Ser Ser Ile Phe Glu Leu Glu Pro
    210                 215                 220

Gln Val Ile Glu Ala Leu Lys Gln Glu Phe Ser Phe Pro Val His Thr
225                 230                 235                 240

Phe Gly Pro Ala Ile Pro Tyr Phe Asn Leu Arg Lys Ala Thr Ser Phe
                245                 250                 255
```

-continued

```
Leu Thr Ser Gln Asn Asp His Asp His His Tyr Phe Glu Trp Leu Asn
            260                 265                 270
Ser Gln Pro Pro Cys Ser Val Leu Tyr Val Ser Leu Gly Ser Phe Leu
        275                 280                 285
Ser Val Ser Ser Ala Gln Met Asp Glu Phe Ala Asp Gly Leu Arg Glu
    290                 295                 300
Ser Gly Val Arg Phe Leu Trp Val Ala Arg Gly Glu Ala Thr Arg Leu
305                 310                 315                 320
Gln Glu Arg Cys Gly Asp Val Gly Arg Val Val Pro Trp Cys Glu Gln
                325                 330                 335
Leu Lys Val Leu Cys His Ser Ser Val Gly Gly Phe Trp Thr His Cys
            340                 345                 350
Gly Trp Asn Ser Thr Met Glu Ala Ile Phe Ala Gly Val Pro Val Ile
        355                 360                 365
Ala Phe Pro Leu Thr Met Asp Gln Thr Thr Ile Arg Lys His Val Val
    370                 375                 380
Glu Asp Trp Lys Met Gly Trp Asp Ala Lys Lys Gly Leu Glu Ala Gly
385                 390                 395                 400
Asn Leu Leu Arg Ser Ala Arg Ile Ala Glu Leu Val Lys Lys Leu Met
                405                 410                 415
Asp Leu Glu Cys Val Glu Arg Lys Glu Ile Ala Ala Arg Ala Lys Glu
            420                 425                 430
Leu Gln Lys Val Thr Leu Gln Ala Val Ser Glu Gly Gly Ser Ser Lys
        435                 440                 445
Ala Asn Leu Thr Ser Phe Leu Asp Asp Ile Ala Ser Phe Ser
    450                 455                 460
```

<210> SEQ ID NO 5
<211> LENGTH: 1458
<212> TYPE: DNA
<213> ORGANISM: Sesamun indicum

<400> SEQUENCE: 5

```
atggccgagt gtcaccgcaa gccgcacgct atcatgatct caatcccata ccagggccat    60
attaacccct tcgtcaatct agctctcaag attgcttcaa agggcttttc catcactttc   120
gttcatttcg aatctgttca ccacagggtg tctaaagccc accatctcca ttgcaataaa   180
acccaagtcg atatcttttc tgaagcacgg gaatcaggtc ttgacatacg ctacacgact   240
attagcgatg gcttgccggt ggaattcgat agatattcca actttgaaga gtactgggga   300
aggatattgc gtgattttcc agctcgtgta gatgaatttg tcggaaagat tatccagtct   360
gatccatatg tggactattt cttcgtagcc gacactttt tcccttaccc tgcaaccatt   420
gctgagaagt acaaccttgt caatgtctca ctctggactc aaccagcctt ggttttact   480
ctagcttacc acttggacct tctgagagag aatgggcatt tcccatgtaa agataacatc   540
cacgaggaag taaattatat tcctggagtc aagccgataa gtacaagaga cttggtttca   600
gttatgaagg aatcggaaca aggatatcac acaatgctca catctttatt catggcatct   660
gaccaagcga agaaggcaga ctttatactg cataacactg tgcatgaatt agaagccgat   720
acgctgtcag ctctaaacaa ataccagcct aactatgcaa ttggccctat taatttttt   780
aaaaatttgc ccacatatac tgtcagcaag aatttatggt ctgaatcgga ctgcactgag   840
tggctcaagt ccaagcttcc cggctcagtt ttgtacgtct cgttcgggag ctttgtgcac   900
actagcaggc aggtaattga agaaatagcc tatgggctgc ttcttagcca agtaaatttc   960
atttgggcca ttcgagaagg aattctgagt tccggtgata ctaatattat gcctaatgga  1020
```

```
tatgaggatg aggttgaaga taaagggttg ataattcctt ggtgtaatca aatcagggtt    1080
ctctctaatc cagccgttgg aggattcttg acacataacg ggtggaattc gacaatagag    1140
agcatgtggt gtgctgttcc gatgatttgc tatccatttt cgtatgatca acctaccaat    1200
aggaagctag tggtcgatga ttggaagtgt gggattagtc tttgtgatgg aacatctgtt    1260
gacaggaagg aagttgctga aagataaag agctttatga gtggagctgc tacaaaaagc    1320
tttaggcaag aggcagataa ggtgaagacg attctgcatc acgccttgga agttgatgga    1380
tcgtctgaga ggaatttcga tcaatttatc aaggatttga aggacaaaat tcattctaca    1440
actacaagta ttaaataa                                                   1458

<210> SEQ ID NO 6
<211> LENGTH: 485
<212> TYPE: PRT
<213> ORGANISM: Sesamun indicum

<400> SEQUENCE: 6
```

Met Ala Glu Cys His Arg Lys Pro His Ala Ile Met Ile Ser Ile Pro
1               5                   10                  15

Tyr Gln Gly His Ile Asn Pro Phe Val Asn Leu Ala Leu Lys Ile Ala
            20                  25                  30

Ser Lys Gly Phe Ser Ile Thr Phe Val His Phe Glu Ser Val His His
        35                  40                  45

Arg Val Ser Lys Ala His His Leu His Cys Asn Lys Thr Gln Val Asp
    50                  55                  60

Ile Phe Ser Glu Ala Arg Glu Ser Gly Leu Asp Ile Arg Tyr Thr Thr
65                  70                  75                  80

Ile Ser Asp Gly Leu Pro Val Glu Phe Asp Arg Tyr Ser Asn Phe Glu
                85                  90                  95

Glu Tyr Trp Gly Arg Ile Leu Arg Asp Phe Pro Ala Arg Val Asp Glu
            100                 105                 110

Phe Val Gly Lys Ile Ile Gln Ser Asp Pro Tyr Val Asp Tyr Phe Phe
        115                 120                 125

Val Ala Asp Thr Phe Phe Pro Tyr Pro Ala Thr Ile Ala Glu Lys Tyr
    130                 135                 140

Asn Leu Val Asn Val Ser Leu Trp Thr Gln Pro Ala Leu Val Phe Thr
145                 150                 155                 160

Leu Ala Tyr His Leu Asp Leu Leu Arg Glu Asn Gly His Phe Pro Cys
                165                 170                 175

Lys Asp Asn Ile His Glu Glu Val Asn Tyr Ile Pro Gly Val Lys Pro
            180                 185                 190

Ile Ser Thr Arg Asp Leu Val Ser Val Met Lys Glu Ser Glu Gln Gly
        195                 200                 205

Tyr His Thr Met Leu Thr Ser Leu Phe Met Ala Ser Asp Gln Ala Lys
    210                 215                 220

Lys Ala Asp Phe Ile Leu His Asn Thr Val His Glu Leu Glu Ala Asp
225                 230                 235                 240

Thr Leu Ser Ala Leu Asn Lys Tyr Gln Pro Asn Tyr Ala Ile Gly Pro
                245                 250                 255

Ile Asn Phe Phe Lys Asn Leu Pro Thr Tyr Thr Val Ser Lys Asn Leu
            260                 265                 270

Trp Ser Glu Ser Asp Cys Thr Glu Trp Leu Lys Ser Lys Leu Pro Gly
        275                 280                 285

Ser Val Leu Tyr Val Ser Phe Gly Ser Phe Val His Thr Ser Arg Gln

```
                290                  295                  300
Val Ile Glu Glu Ile Ala Tyr Gly Leu Leu Ser Gln Val Asn Phe
305                 310                 315                 320

Ile Trp Ala Ile Arg Glu Gly Ile Leu Ser Ser Gly Asp Thr Asn Ile
                325                 330                 335

Met Pro Asn Gly Tyr Glu Asp Glu Val Glu Asp Lys Gly Leu Ile Ile
                340                 345                 350

Pro Trp Cys Asn Gln Ile Arg Val Leu Ser Asn Pro Ala Val Gly Gly
                355                 360                 365

Phe Leu Thr His Asn Gly Trp Asn Ser Thr Ile Glu Ser Met Trp Cys
370                 375                 380

Ala Val Pro Met Ile Cys Tyr Pro Phe Ser Tyr Asp Gln Pro Thr Asn
385                 390                 395                 400

Arg Lys Leu Val Val Asp Asp Trp Lys Cys Gly Ile Ser Leu Cys Asp
                405                 410                 415

Gly Thr Ser Val Asp Arg Lys Glu Val Ala Glu Lys Ile Lys Ser Phe
                420                 425                 430

Met Ser Gly Ala Ala Thr Lys Ser Phe Arg Gln Glu Ala Asp Lys Val
                435                 440                 445

Lys Thr Ile Leu His His Ala Leu Glu Val Asp Gly Ser Ser Glu Arg
450                 455                 460

Asn Phe Asp Gln Phe Ile Lys Asp Leu Lys Asp Lys Ile His Ser Thr
465                 470                 475                 480

Thr Thr Ser Ile Lys
            485

<210> SEQ ID NO 7
<211> LENGTH: 1545
<212> TYPE: DNA
<213> ORGANISM: Sesamun indicum

<400> SEQUENCE: 7
atggcgtcaa tgccatccca agaacaaaac cctcacttcg tcttgcttcc tttcctggcc     60
caaggccaca tgattccaat ggtggatctt gccaggttgc tggccaagcg cggtttgacg    120
atcagcattc taacaacccc tcataatgcc gaccgatttc agtcggtcat cgaccgtgaa    180
atcggctctg gactcgacat tcgtatcatc cacctcaaat ttccatgtgc tgaagccggg    240
cttccagatg gctgtgagaa tttcgacatg ctcccgtcga tcgattgtgg agtgaaattc    300
ttcagagcta cagccatgct gaatgagcag gttgaggagt gctccggca gctgaagccc    360 tttcctcgct gcttcattgc tgatatgtgt tatccttggg ctacgaaggt tgctcggaag    420
ttgcacattc aagaattctt ttttcatggg acgtgttgtt tttctctctt atgcacgcac    480
atcatacgaa tttccaaaga tttggaaact atagcttctg atactgagta ctttgtcgtg    540
cctggattgc ctgatagaat tgagttaact agagctcagc ttagaggcac tccaaatgaa    600
cggaattctg attggaggga gctctgggat cagttggcag aggctgaggg agaagcattt    660
ggaacagttg ccaacagttt tgaagagctg aacctgatt acattaaaga atacatgaaa    720
gccacaggaa agaaggtgtg gtgtgttggt cctgtttcct tgtgcaacaa agtgactca    780 gacaagactg aaagaggaaa caaaacctct attggcggac aagaatgcct gaaatggctc    840
gacttgcagg aaccaggctc ggttatttac gtttgcctcg gaagcctatc ctgcctgcct    900
acttcacaac tgatcgagct cggcttagcg ttgaagcttc aaagagacc cttcatttgg    960 gttctccgaa atgcatctga agaattccaa acatggcttt tggaagaaaa attcgaggaa   1020
```

-continued

```
aggatcaagg acagggcat cttgatccgt ggatgggccc ctcaagtgct gatactttct    1080
catctgtcta taggaggatt cttgacgcat tgtggatgga actcgactct ggaaggaata    1140
acggcaggcg tgccgatgat aacatggccg cttttcgccg agcaatattg caatgagaag    1200
ttcattgtga aggtgataaa gacaggaata agagttggta ttgaaacgcc tgttgtgttt    1260
ggagaagagg agagtgtggg aacgctggtg aagagtgatg agattaagag tgttattgag    1320
aggttgatgg acggggggaga agaagggaat gagaggagaa aacgagctaa agagctggga    1380
gaaatgacga aaagggcagt ggaggaaggg ggttcctctt acctgaatat gactttgttc    1440
atagaagatg tcatggcgga acaagcaaac tctggagacc aatctgcaaa tcatgaaaat    1500
gcattggtag atcatgaaaa ttctgatgtt gtcatggtcc actga                    1545
```

<210> SEQ ID NO 8
<211> LENGTH: 514
<212> TYPE: PRT
<213> ORGANISM: Sesamun indicum

<400> SEQUENCE: 8

```
Met Ala Ser Met Ala Ile Gln Glu Gln Asn Pro His Phe Val Leu Leu
 1               5                  10                  15

Pro Phe Leu Ala Gln Gly His Met Ile Pro Met Val Asp Leu Ala Arg
            20                  25                  30

Leu Leu Ala Lys Arg Gly Leu Thr Ile Ser Ile Leu Thr Thr Pro His
        35                  40                  45

Asn Ala Asp Arg Phe Gln Ser Val Ile Asp Arg Glu Ile Gly Ser Gly
    50                  55                  60

Leu Asp Ile Arg Ile Ile His Leu Lys Phe Pro Cys Ala Glu Ala Gly
65                  70                  75                  80

Leu Pro Asp Gly Cys Glu Asn Phe Asp Met Leu Pro Ser Ile Asp Cys
                85                  90                  95

Gly Val Lys Phe Phe Arg Ala Thr Ala Met Leu Asn Glu Gln Val Glu
            100                 105                 110

Glu Leu Leu Arg Gln Leu Lys Pro Phe Pro Arg Cys Phe Ile Ala Asp
        115                 120                 125

Met Cys Tyr Pro Trp Ala Thr Lys Val Ala Arg Lys Leu His Ile Pro
    130                 135                 140

Arg Ile Leu Phe His Gly Thr Cys Cys Phe Ser Leu Leu Cys Thr His
145                 150                 155                 160

Ile Ile Arg Ile Ser Lys Asp Leu Glu Thr Ile Ala Ser Asp Thr Glu
                165                 170                 175

Tyr Phe Val Val Pro Gly Leu Pro Asp Arg Ile Glu Leu Thr Arg Ala
            180                 185                 190

Gln Leu Arg Gly Thr Pro Asn Glu Arg Asn Ser Asp Trp Arg Glu Leu
        195                 200                 205

Trp Asp Gln Leu Ala Glu Ala Glu Gly Glu Ala Phe Gly Thr Val Ala
    210                 215                 220

Asn Ser Phe Glu Glu Leu Glu Pro Asp Tyr Ile Lys Glu Tyr Met Lys
225                 230                 235                 240

Ala Thr Gly Lys Lys Val Trp Cys Val Gly Pro Val Ser Leu Cys Asn
                245                 250                 255

Lys Ser Asp Ser Asp Lys Thr Glu Arg Gly Asn Lys Thr Ser Ile Gly
            260                 265                 270

Gly Gln Glu Cys Leu Lys Trp Leu Asp Leu Gln Glu Pro Gly Ser Val
        275                 280                 285
```

```
Ile Tyr Val Cys Leu Gly Ser Leu Ser Cys Leu Pro Thr Ser Gln Leu
            290                 295                 300

Ile Glu Leu Gly Leu Ala Leu Glu Ala Ser Lys Arg Pro Phe Ile Trp
305                 310                 315                 320

Val Leu Arg Asn Ala Ser Glu Glu Phe Gln Thr Trp Leu Leu Glu Glu
                325                 330                 335

Lys Phe Glu Glu Arg Ile Lys Asp Arg Gly Ile Leu Ile Arg Gly Trp
            340                 345                 350

Ala Pro Gln Val Leu Ile Leu Ser His Leu Ser Ile Gly Gly Phe Leu
        355                 360                 365

Thr His Cys Gly Trp Asn Ser Thr Leu Glu Gly Ile Thr Ala Gly Val
370                 375                 380

Pro Met Ile Thr Trp Pro Leu Phe Ala Glu Gln Tyr Cys Asn Glu Lys
385                 390                 395                 400

Phe Ile Val Lys Val Ile Lys Thr Gly Ile Arg Val Gly Ile Glu Thr
                405                 410                 415

Pro Val Val Phe Gly Glu Glu Ser Val Gly Thr Leu Val Lys Ser
            420                 425                 430

Asp Glu Ile Lys Ser Val Ile Glu Arg Leu Met Asp Gly Gly Glu Glu
            435                 440                 445

Gly Asn Glu Arg Arg Lys Arg Ala Lys Glu Leu Gly Glu Met Thr Lys
450                 455                 460

Arg Ala Val Glu Glu Gly Gly Ser Ser Tyr Leu Asn Met Thr Leu Phe
465                 470                 475                 480

Ile Glu Asp Val Met Ala Glu Gln Ala Asn Ser Gly Asp Gln Ser Ala
                485                 490                 495

Asn His Glu Asn Ala Leu Val Asp His Glu Asn Ser Asp Val Val Met
            500                 505                 510

Val His

<210> SEQ ID NO 9
<211> LENGTH: 1407
<212> TYPE: DNA
<213> ORGANISM: Sesamun indicum

<400> SEQUENCE: 9
atgggcagct tgagcaatca acagagccaa catgatgatc atactagtat ggaacaagtt      60
gctgtgatca tggttccatt tgcagctcaa ggccatctga atcagctgat gcagctctca     120
tgcctgatat cttcatacgg gttgcctgtt ttctacatca gctctgccat ccacatccgt     180
caagccagag ttcgtgtgaa cggcttgaac cctctagacg tggctaaaat ccacttccac     240
gaaatccctg ttccgcattt cgcctctcct ccaccggacc ccaactcctc aagcaagttc     300
cctgaacagc tgcagccagc atggaatgcc tcattgagcc tacgacaacc atttgctgca     360
tatctacggg acatgtctga aagtttaaa agagtcgtag ttgttcacga ccctatgatg     420
gctgcggtgg ttcaggatgt catctcaatc cataatgcag agtcctatgc attcaactgc     480
attcccgcat tttctcaagc attttttcatt ggggaaggct tactcaattc atcagcagag     540
cgcctgaaag agttgcattc tttgcaagga tgtataccag aaaaggtgtt ggaatttgtt     600
gctatacacg cagagccatt gaggtacaga gctggagatt tatacaatac ctgcagattg     660
atagaagccc cttacctgga tttactggaa aaagaagaga gtggtgggaa caggaagacc     720
tgggcaatag gccgattct tcctaccaag ttatgtaccg ctgccaaacc tgcaaacaaa     780
tgcttagaat ggcttgatca acaggagcca aaatctgtca tctatgtaag ttttggaacg     840
```

-continued

```
acagtttcgc tatcagatga acagataaaa gagctggctt tggggctaga gcagagcaaa    900
gtgaagttca tttgggtact gagagatgcc gataaaggcg acatctttga cgggcaagtc    960
agaagggctg aactgccgga agggtttgaa gaaagggtga aggaagtggg aaaagtggta   1020
agagattggg cgccacagcc ggagatcttg gcccataaat caacaggtgg atttatgagc   1080
cactgtgggt ggaattcatg catagagagc attactatgg gagtgcctat agcagcctgg   1140
ccgatgcatt cagaccaacc aagaaacaca ttgttcgtaa cacaagtact gaaaatgggg   1200
attgttgtta tggaatggga acagaggacg gaacttgtga aagcgtcggc tattgagaat   1260
gcagtaagaa ggttaatggc gtcggaagaa ggaaatgagg tacggaagag gcagaggac    1320
ttggctgcca ccctgcgaca ggcgattgag cctggcggtg cttctcgact ggagttggat   1380
tcctttgttg cccatataat aagatag                                       1407
```

<210> SEQ ID NO 10
<211> LENGTH: 468
<212> TYPE: PRT
<213> ORGANISM: Sesamun indicum

<400> SEQUENCE: 10

```
Met Gly Ser Leu Ser Asn Gln Gln Ser Gln His Asp Asp His Thr Ser
  1               5                  10                  15

Met Glu Gln Val Ala Val Ile Met Val Pro Phe Ala Ala Gln Gly His
             20                  25                  30

Leu Asn Gln Leu Met Gln Leu Ser Cys Leu Ile Ser Ser Tyr Gly Leu
         35                  40                  45

Pro Val Phe Tyr Ile Ser Ser Ala Ile His Ile Arg Gln Ala Arg Val
     50                  55                  60

Arg Val Asn Gly Leu Asn Pro Leu Asp Val Ala Lys Ile His Phe His
 65                  70                  75                  80

Glu Ile Pro Val Pro His Phe Ala Ser Pro Pro Asp Pro Asn Ser
                 85                  90                  95

Ser Ser Lys Phe Pro Glu Gln Leu Gln Pro Ala Trp Asn Ala Ser Leu
            100                 105                 110

Ser Leu Arg Gln Pro Phe Ala Ala Tyr Leu Arg Asp Met Ser Glu Lys
        115                 120                 125

Phe Lys Arg Val Val Val His Asp Pro Met Met Ala Ala Val Val
    130                 135                 140

Gln Asp Val Ile Ser Ile His Asn Ala Glu Ser Tyr Ala Phe Asn Cys
145                 150                 155                 160

Ile Pro Ala Phe Ser Gln Ala Phe Phe Ile Gly Glu Gly Leu Leu Asn
                165                 170                 175

Ser Ser Ala Glu Arg Leu Lys Glu Leu His Ser Leu Gln Gly Cys Ile
            180                 185                 190

Pro Glu Lys Val Leu Glu Phe Val Ala Ile His Ala Glu Pro Leu Arg
        195                 200                 205

Tyr Arg Ala Gly Asp Leu Tyr Asn Thr Cys Arg Leu Ile Glu Ala Pro
    210                 215                 220

Tyr Leu Asp Leu Leu Glu Lys Glu Glu Ser Gly Gly Asn Arg Lys Thr
225                 230                 235                 240

Trp Ala Ile Gly Pro Ile Leu Pro Thr Lys Leu Cys Thr Ala Ala Lys
                245                 250                 255

Pro Ala Asn Lys Cys Leu Glu Trp Leu Asp Gln Gln Glu Pro Lys Ser
            260                 265                 270

Val Ile Tyr Val Ser Phe Gly Thr Thr Val Ser Leu Ser Asp Glu Gln
```

```
                275                 280                 285
Ile Lys Glu Leu Ala Leu Gly Leu Glu Gln Ser Lys Val Lys Phe Ile
        290                 295                 300

Trp Val Leu Arg Asp Ala Asp Lys Gly Asp Ile Phe Asp Gly Gln Val
305                 310                 315                 320

Arg Arg Ala Glu Leu Pro Glu Gly Phe Glu Glu Arg Val Lys Glu Val
                325                 330                 335

Gly Lys Val Val Arg Asp Trp Ala Pro Gln Pro Glu Ile Leu Ala His
            340                 345                 350

Lys Ser Thr Gly Gly Phe Met Ser His Cys Gly Trp Asn Ser Cys Ile
        355                 360                 365

Glu Ser Ile Thr Met Gly Val Pro Ile Ala Ala Trp Pro Met His Ser
370                 375                 380

Asp Gln Pro Arg Asn Thr Leu Phe Val Thr Gln Val Leu Lys Met Gly
385                 390                 395                 400

Ile Val Val Met Glu Trp Glu Gln Arg Thr Gly Leu Val Lys Ala Ser
                405                 410                 415

Ala Ile Glu Asn Ala Val Arg Arg Leu Met Ala Ser Glu Glu Gly Asn
            420                 425                 430

Glu Val Arg Lys Arg Ala Glu Asp Leu Ala Ala Thr Leu Arg Gln Ala
        435                 440                 445

Ile Glu Pro Gly Gly Ala Ser Arg Leu Glu Leu Asp Ser Phe Val Ala
    450                 455                 460

His Ile Ile Arg
465

<210> SEQ ID NO 11
<211> LENGTH: 21
<212> TYPE: DNA
<213> ORGANISM: Ipomoea nil

<400> SEQUENCE: 11
gaaatggtcg gattggctgg g                                           21

<210> SEQ ID NO 12
<211> LENGTH: 21
<212> TYPE: DNA
<213> ORGANISM: Ipomoea nil

<400> SEQUENCE: 12
acctccaccc caactttcag g                                           21

<210> SEQ ID NO 13
<211> LENGTH: 24
<212> TYPE: DNA
<213> ORGANISM: Gentiana scabra var. buergeri

<400> SEQUENCE: 13
gatgcataat ttggctagaa aagc                                        24

<210> SEQ ID NO 14
<211> LENGTH: 21
<212> TYPE: DNA
<213> ORGANISM: Petunia hybrida

<400> SEQUENCE: 14
ccaatttgcc aaacactttc c                                           21

<210> SEQ ID NO 15
```

```
<211> LENGTH: 21
<212> TYPE: DNA
<213> ORGANISM: Verbena hybrida

<400> SEQUENCE: 15
tgcctcgaat ggttgagcac g                                              21

<210> SEQ ID NO 16
<211> LENGTH: 18
<212> TYPE: DNA
<213> ORGANISM: Verbena hybrida

<400> SEQUENCE: 16
ctctcactct cacacccg                                                  18

<210> SEQ ID NO 17
<211> LENGTH: 21
<212> TYPE: DNA
<213> ORGANISM: Scutellaria baicalensis Georgi

<400> SEQUENCE: 17
cacgaatgct tagcatggct c                                              21

<210> SEQ ID NO 18
<211> LENGTH: 21
<212> TYPE: DNA
<213> ORGANISM: Scutellaria baicalensis Georgi

<400> SEQUENCE: 18
cttattgccc actgaaaccc c                                              21

<210> SEQ ID NO 19
<211> LENGTH: 21
<212> TYPE: DNA
<213> ORGANISM: Gentiana scabra var. buergeri

<400> SEQUENCE: 19
tgtctgaatt ggcttgattc c                                              21

<210> SEQ ID NO 20
<211> LENGTH: 21
<212> TYPE: DNA
<213> ORGANISM: Gentiana scabra var. buergeri

<400> SEQUENCE: 20
aacccacaga aacccctgtt c                                              21

<210> SEQ ID NO 21
<211> LENGTH: 21
<212> TYPE: DNA
<213> ORGANISM: Sesamun indicum

<400> SEQUENCE: 21
tagatgaatt tgtcggaaag a                                              21

<210> SEQ ID NO 22
<211> LENGTH: 21
<212> TYPE: DNA
<213> ORGANISM: Sesamun indicum

<400> SEQUENCE: 22
tataatgtta caaaatcaac t                                              21

<210> SEQ ID NO 23
```

```
<211> LENGTH: 22
<212> TYPE: DNA
<213> ORGANISM: Sesamun indicum

<400> SEQUENCE: 23
ggcagagttt tctatgggtt gt                                              22

<210> SEQ ID NO 24
<211> LENGTH: 21
<212> TYPE: DNA
<213> ORGANISM: Sesamun indicum

<400> SEQUENCE: 24
atagcagtgg ggctagaaag a                                               21

<210> SEQ ID NO 25
<211> LENGTH: 23
<212> TYPE: DNA
<213> ORGANISM: Sesamun indicum

<400> SEQUENCE: 25
cctgtaacta gaatggcgtc aat                                             23

<210> SEQ ID NO 26
<211> LENGTH: 24
<212> TYPE: DNA
<213> ORGANISM: Sesamun indicum

<400> SEQUENCE: 26
tttgacaaaa ccaaaaccac actt                                            24

<210> SEQ ID NO 27
<211> LENGTH: 24
<212> TYPE: DNA
<213> ORGANISM: Sesamun indicum

<400> SEQUENCE: 27
tttagctcgt tttctcctct catt                                            24

<210> SEQ ID NO 28
<211> LENGTH: 24
<212> TYPE: DNA
<213> ORGANISM: Sesamun indicum

<400> SEQUENCE: 28
ctacatgtta ttacatctac agaa                                            24

<210> SEQ ID NO 29
<211> LENGTH: 21
<212> TYPE: DNA
<213> ORGANISM: Sesamun indicum

<400> SEQUENCE: 29
catctcaatc cataatgcag a                                               21

<210> SEQ ID NO 30
<211> LENGTH: 24
<212> TYPE: DNA
<213> ORGANISM: Sesamun indicum

<400> SEQUENCE: 30
aacaagaact cacttgaaga taat                                            24

<210> SEQ ID NO 31
```

```
<211> LENGTH: 21
<212> TYPE: DNA
<213> ORGANISM: Sesamun indicum

<400> SEQUENCE: 31
gccattgaca ggtatgagtt a                                           21

<210> SEQ ID NO 32
<211> LENGTH: 24
<212> TYPE: DNA
<213> ORGANISM: Sesamun indicum

<400> SEQUENCE: 32
gatctaatgt ttacatagta tcct                                        24

<210> SEQ ID NO 33
<211> LENGTH: 21
<212> TYPE: DNA
<213> ORGANISM: Sesamun indicum

<400> SEQUENCE: 33
catcacccac ttcatttcca a                                           21

<210> SEQ ID NO 34
<211> LENGTH: 24
<212> TYPE: DNA
<213> ORGANISM: Sesamun indicum

<400> SEQUENCE: 34
attattatta tttttcaata atta                                        24

<210> SEQ ID NO 35
<211> LENGTH: 23
<212> TYPE: DNA
<213> ORGANISM: Sesamun indicum

<400> SEQUENCE: 35
tttatcctgt ggggccaata ctt                                         23

<210> SEQ ID NO 36
<211> LENGTH: 24
<212> TYPE: DNA
<213> ORGANISM: Sesamun indicum

<400> SEQUENCE: 36
tcttgccatt cacattcaga ttga                                        24

<210> SEQ ID NO 37
<211> LENGTH: 24
<212> TYPE: DNA
<213> ORGANISM: Sesamun indicum

<400> SEQUENCE: 37
acaactaagc ataagtcact taaa                                        24

<210> SEQ ID NO 38
<211> LENGTH: 21
<212> TYPE: DNA
<213> ORGANISM: Sesamun indicum

<400> SEQUENCE: 38
gccttcttcg cttggtcaga t                                           21

<210> SEQ ID NO 39
```

```
<211> LENGTH: 21
<212> TYPE: DNA
<213> ORGANISM: Sesamun indicum

<400> SEQUENCE: 39
gaagccgcca ggtatttgct t                                              21

<210> SEQ ID NO 40
<211> LENGTH: 21
<212> TYPE: DNA
<213> ORGANISM: Sesamun indicum

<400> SEQUENCE: 40
acaagataaa acataatcct a                                              21

<210> SEQ ID NO 41
<211> LENGTH: 24
<212> TYPE: DNA
<213> ORGANISM: Sesamun indicum

<400> SEQUENCE: 41
tttccagctc aaggccatat taat                                           24

<210> SEQ ID NO 42
<211> LENGTH: 24
<212> TYPE: DNA
<213> ORGANISM: Sesamun indicum

<400> SEQUENCE: 42
tacaaacgac acagagaaat agga                                           24

<210> SEQ ID NO 43
<211> LENGTH: 21
<212> TYPE: DNA
<213> ORGANISM: Sesamun indicum

<400> SEQUENCE: 43
aagtacaagt ggatggatat a                                              21

<210> SEQ ID NO 44
<211> LENGTH: 24
<212> TYPE: DNA
<213> ORGANISM: Sesamun indicum

<400> SEQUENCE: 44
acggcttatt ccaactatct aaca                                           24

<210> SEQ ID NO 45
<211> LENGTH: 21
<212> TYPE: DNA
<213> ORGANISM: Sesamun indicum

<400> SEQUENCE: 45
aggttttgag aactggagtt t                                              21

<210> SEQ ID NO 46
<211> LENGTH: 24
<212> TYPE: DNA
<213> ORGANISM: Sesamun indicum

<400> SEQUENCE: 46
taataaagct ggaaacttca ccaa                                           24

<210> SEQ ID NO 47
```

```
<211> LENGTH: 23
<212> TYPE: DNA
<213> ORGANISM: Sesamun indicum

<400> SEQUENCE: 47
ctagtggagc taggaaaact cat                                              23

<210> SEQ ID NO 48
<211> LENGTH: 21
<212> TYPE: DNA
<213> ORGANISM: Sesamun indicum

<400> SEQUENCE: 48
agattaagca cgtttccaca a                                                21

<210> SEQ ID NO 49
<211> LENGTH: 21
<212> TYPE: DNA
<213> ORGANISM: Sesamun indicum

<400> SEQUENCE: 49
tgatcaagtt gccgtggtaa t                                                21

<210> SEQ ID NO 50
<211> LENGTH: 21
<212> TYPE: DNA
<213> ORGANISM: Sesamun indicum

<400> SEQUENCE: 50
aacgtacaag aagtatatat t                                                21

<210> SEQ ID NO 51
<211> LENGTH: 21
<212> TYPE: DNA
<213> ORGANISM: Sesamun indicum

<400> SEQUENCE: 51
tttcttccga tgatagctca t                                                21

<210> SEQ ID NO 52
<211> LENGTH: 21
<212> TYPE: DNA
<213> ORGANISM: Sesamun indicum

<400> SEQUENCE: 52
gtcaacttat ctggaagatc a                                                21

<210> SEQ ID NO 53
<211> LENGTH: 21
<212> TYPE: DNA
<213> ORGANISM: Sesamun indicum

<400> SEQUENCE: 53
acgggaatca ggtcttgaca t                                                21

<210> SEQ ID NO 54
<211> LENGTH: 24
<212> TYPE: DNA
<213> ORGANISM: Sesamun indicum

<400> SEQUENCE: 54
gatgattgat caacagtgca tctt                                             24

<210> SEQ ID NO 55
```

```
<211> LENGTH: 21
<212> TYPE: DNA
<213> ORGANISM: Sesamun indicum

<400> SEQUENCE: 55
ccatcggaat taccatctga a                                              21

<210> SEQ ID NO 56
<211> LENGTH: 21
<212> TYPE: DNA
<213> ORGANISM: Sesamun indicum

<400> SEQUENCE: 56
ataatcaaag gtctctgcaa a                                              21

<210> SEQ ID NO 57
<211> LENGTH: 21
<212> TYPE: DNA
<213> ORGANISM: Sesamun indicum

<400> SEQUENCE: 57
tatgcttgtc tcaaagatta a                                              21

<210> SEQ ID NO 58
<211> LENGTH: 21
<212> TYPE: DNA
<213> ORGANISM: Sesamun indicum

<400> SEQUENCE: 58
aacatctaag ggcatcacag a                                              21

<210> SEQ ID NO 59
<211> LENGTH: 30
<212> TYPE: DNA
<213> ORGANISM: Sesamun indicum

<400> SEQUENCE: 59
ggatcctttt cagccaacat ggaagctgaa                                     30

<210> SEQ ID NO 60
<211> LENGTH: 33
<212> TYPE: DNA
<213> ORGANISM: Sesamun indicum

<400> SEQUENCE: 60
ctcgagaaaa agagcatcat ttaatcatac act                                 33

<210> SEQ ID NO 61
<211> LENGTH: 28
<212> TYPE: DNA
<213> ORGANISM: Sesamun indicum

<400> SEQUENCE: 61
gggaaatgcc cattctctct cagaaggt                                       28

<210> SEQ ID NO 62
<211> LENGTH: 21
<212> TYPE: DNA
<213> ORGANISM: Sesamun indicum

<400> SEQUENCE: 62
gtaagctaga gtaaaaacca a                                              21

<210> SEQ ID NO 63
```

-continued

```
<211> LENGTH: 30
<212> TYPE: DNA
<213> ORGANISM: Sesamun indicum

<400> SEQUENCE: 63
gcccaggtgt tcctgttccc accactctct                                    30

<210> SEQ ID NO 64
<211> LENGTH: 24
<212> TYPE: DNA
<213> ORGANISM: Sesamun indicum

<400> SEQUENCE: 64
aatctgcagg tattgtataa atct                                          24

<210> SEQ ID NO 65
<211> LENGTH: 33
<212> TYPE: DNA
<213> ORGANISM: Sesamun indicum

<400> SEQUENCE: 65
ccacagcaat ctccttcacc tgatcccctt cca                                33

<210> SEQ ID NO 66
<211> LENGTH: 27
<212> TYPE: DNA
<213> ORGANISM: Sesamun indicum

<400> SEQUENCE: 66
caaagcaaag aaacactaca gaagaat                                       27

<210> SEQ ID NO 67
<211> LENGTH: 30
<212> TYPE: DNA
<213> ORGANISM: Sesamun indicum

<400> SEQUENCE: 67
cctccgcttc caacctcaa ccgcccagta                                     30

<210> SEQ ID NO 68
<211> LENGTH: 24
<212> TYPE: DNA
<213> ORGANISM: Sesamun indicum

<400> SEQUENCE: 68
acgtatcggc aattataaaa ttaa                                          24

<210> SEQ ID NO 69
<211> LENGTH: 30
<212> TYPE: DNA
<213> ORGANISM: Sesamun indicum

<400> SEQUENCE: 69
aaacagcaaa cagaaaccat ggccgagtgt                                    30

<210> SEQ ID NO 70
<211> LENGTH: 51
<212> TYPE: DNA
<213> ORGANISM: Sesamun indicum

<400> SEQUENCE: 70
tttggtacca gatcttttgc agctagtcaa ctattattta atacttgtag t            51

<210> SEQ ID NO 71
```

```
<211> LENGTH: 33
<212> TYPE: DNA
<213> ORGANISM: Sesamun indicum

<400> SEQUENCE: 71
aaaaccatgg cgtcaatggc catccaagaa caa                                33

<210> SEQ ID NO 72
<211> LENGTH: 47
<212> TYPE: DNA
<213> ORGANISM: Sesamun indicum

<400> SEQUENCE: 72
aaaagatctg gtacctcagt ggaccatgac aacatcagaa ttttcat                 47

<210> SEQ ID NO 73
<211> LENGTH: 31
<212> TYPE: DNA
<213> ORGANISM: Sesamun indicum

<400> SEQUENCE: 73
aaaaccatgg gcagcttgag caatcaacag a                                  31

<210> SEQ ID NO 74
<211> LENGTH: 38
<212> TYPE: DNA
<213> ORGANISM: Sesamun indicum

<400> SEQUENCE: 74
aaaggtaccc tatcttatta tatgggcaac aaaggaat                           38

<210> SEQ ID NO 75
<211> LENGTH: 28
<212> TYPE: DNA
<213> ORGANISM: Sesamun indicum

<400> SEQUENCE: 75
aaaaccatgg cggcggacca aaaattaa                                      28

<210> SEQ ID NO 76
<211> LENGTH: 33
<212> TYPE: DNA
<213> ORGANISM: Sesamun indicum

<400> SEQUENCE: 76
aaaggtacct caagaaatgt tattcacgac att                                33

<210> SEQ ID NO 77
<211> LENGTH: 38
<212> TYPE: DNA
<213> ORGANISM: Sesamun indicum

<400> SEQUENCE: 77
aaaaccatgg cgccggcggc gagaaccgac ccaatcat                           38

<210> SEQ ID NO 78
<211> LENGTH: 39
<212> TYPE: DNA
<213> ORGANISM: Sesamun indicum

<400> SEQUENCE: 78
tttggtacct cagctaaacg atgcaatatc atcgaggaa                          39

<210> SEQ ID NO 79
```

```
<211> LENGTH: 34
<212> TYPE: DNA
<213> ORGANISM: Sesamun indicum

<400> SEQUENCE: 79
tttggatcca tgtcggcgga ccaaaaatta acca                              34

<210> SEQ ID NO 80
<211> LENGTH: 35
<212> TYPE: DNA
<213> ORGANISM: Sesamun indicum

<400> SEQUENCE: 80
tttggtacct caagaaatgt tattcacgac attct                             35

<210> SEQ ID NO 81
<211> LENGTH: 1428
<212> TYPE: DNA
<213> ORGANISM: Sesamun indicum

<400> SEQUENCE: 81
atgtcggcgg accaaaaatt aagcagccta gttttcgttc ctttccctat aatgagtcac   60
ctggcaacag cagtgaagac ggcgaagctc ctggccgaca gggacgaacg cctctcaatc  120
acagtcctcg cgatgaagct gccgattgat acgctgatca gttcttacac caagaactcg  180
cctgacgccc gggtgaaagt ggtcgaactg cccgcagacg agcccacctt tacaaagctg  240
atgaaatctt ccaagaactt cttctttcga tacatcgaga gccagaaagg cgctgtcagg  300
gacgctgttg ctgagataat gaagaattcg agatcgagca cgtttgcagg atttgtaatc  360
gacatgttct gcacgcccat gattgatgtc gccaacgagc tcggtgtccc gacttacatg  420
ttcttcagtt cgggctcagc aacgctcggg ctcatgttcc atcttcagag tctcagagat  480
gacagtaatg tggacctgat ggagtacaag aattcagatg ctgcgttatc aataccgacg  540
ttcgttcacc ccgttcctgt tgctgtgtgg ccttccgcgg tgtttgagga tagtgatttc  600
cttgactttg ctaaaaggtt tagagaaacc aaagggatta tcgtgaacac attccttgag  660
ttcgaaactc accagatcag gtcactctct gatgataaga acattccacc agttttttcct  720 gtcgggccaa tacttcaagc tgatgcgaac aaaattgagc aagaaaagca aaagcacggg  780
gaaatcatgg ggtggctcga caggcaacct gattcttccg tcgtgtttct ttgctttggt  840
acccatggat gtttggaagg ggatcaggtg aaggagattg ctgtggccct ggaaaacagt  900
ggacatcggt tttgtggtc cctgaggaag ccgcctccga agaaaaggt tgcgtttcca  960 ggagagtatg agaattccga agaagtatta ccggaagggt tcctggaacg aactgctgag 1020
atggggaaag tgatcgggtg ggcgccgcaa atggcagtgt tatctcatcc tgcagtggga 1080
ggattcgtgt cgcactgtgg gtggaactcg acgttggaaa gcgtgtggtg tggggtgccg 1140
atggccgtgt ggccgttgtc tgcagagcag caggccaatg cgttcttgct ggtgaaggag 1200
tttgaaatgg cagttgagat taagatggat tataataagg atagtaacgt gattgtgggc 1260
gcagagacca tagagaaagc aatcaggcag ctaatggacc cggagaatga gattcgggtt 1320
aaggtgagag cattgacaga gaagagcaga atggccttaa tggaaggagg gtcttcgtac 1380
aattacttga aacgtttcgt tgagaatgtc gtgaataaca tttcttga              1428

<210> SEQ ID NO 82
<211> LENGTH: 475
<212> TYPE: PRT
<213> ORGANISM: Sesamun indicum
```

<400> SEQUENCE: 82

```
Met Ser Ala Asp Gln Lys Leu Ser Ser Leu Val Phe Val Pro Phe Pro
  1               5                  10                  15

Ile Met Ser His Leu Ala Thr Ala Val Lys Thr Ala Lys Leu Leu Ala
             20                  25                  30

Asp Arg Asp Glu Arg Leu Ser Ile Thr Val Leu Ala Met Lys Leu Pro
         35                  40                  45

Ile Asp Thr Leu Ile Ser Ser Tyr Thr Lys Asn Ser Pro Asp Ala Arg
     50                  55                  60

Val Lys Val Val Glu Leu Pro Ala Asp Glu Pro Thr Phe Thr Lys Leu
 65                  70                  75                  80

Met Lys Ser Ser Lys Asn Phe Phe Arg Tyr Ile Glu Ser Gln Lys
                 85                  90                  95

Gly Ala Val Arg Asp Ala Val Ala Glu Ile Met Lys Asn Ser Arg Ser
                100                 105                 110

Ser Thr Phe Ala Gly Phe Val Ile Asp Met Phe Cys Thr Pro Met Ile
            115                 120                 125

Asp Val Ala Asn Glu Leu Gly Val Pro Thr Tyr Met Phe Phe Ser Ser
        130                 135                 140

Gly Ser Ala Thr Leu Gly Leu Met Phe His Leu Gln Ser Leu Arg Asp
145                 150                 155                 160

Asp Ser Asn Val Asp Leu Met Glu Tyr Lys Asn Ser Asp Ala Ala Leu
                165                 170                 175

Ser Ile Pro Thr Phe Val His Pro Val Pro Val Ala Val Trp Pro Ser
                180                 185                 190

Ala Val Phe Glu Asp Ser Asp Phe Leu Asp Phe Ala Lys Arg Phe Arg
            195                 200                 205

Glu Thr Lys Gly Ile Ile Val Asn Thr Phe Leu Glu Phe Glu Thr His
210                 215                 220

Gln Ile Arg Ser Leu Ser Asp Asp Lys Asn Ile Pro Pro Val Phe Pro
225                 230                 235                 240

Val Gly Pro Ile Leu Gln Ala Asp Ala Asn Lys Ile Glu Gln Glu Lys
                245                 250                 255

Gln Lys His Gly Glu Ile Met Gly Trp Leu Asp Arg Gln Pro Asp Ser
            260                 265                 270

Ser Val Val Phe Leu Cys Phe Gly Thr His Gly Cys Leu Glu Gly Asp
        275                 280                 285

Gln Val Lys Glu Ile Ala Val Ala Leu Glu Asn Ser Gly His Arg Phe
    290                 295                 300

Leu Trp Ser Leu Arg Lys Pro Pro Lys Glu Lys Val Ala Phe Pro
305                 310                 315                 320

Gly Glu Tyr Glu Asn Ser Glu Val Leu Pro Gly Phe Leu Glu
                325                 330                 335

Arg Thr Ala Glu Met Gly Lys Val Ile Gly Trp Ala Pro Gln Met Ala
            340                 345                 350

Val Leu Ser His Pro Ala Val Gly Gly Phe Val Ser His Cys Gly Trp
        355                 360                 365

Asn Ser Thr Leu Glu Ser Val Trp Cys Gly Val Pro Met Ala Val Trp
    370                 375                 380

Pro Leu Ser Ala Glu Gln Gln Ala Asn Ala Phe Leu Leu Val Lys Glu
385                 390                 395                 400

Phe Glu Met Ala Val Glu Ile Lys Met Asp Tyr Asn Lys Asp Ser Asn
                405                 410                 415
```

```
Val Ile Val Gly Ala Glu Thr Ile Glu Lys Ala Ile Arg Gln Leu Met
            420                 425                 430

Asp Pro Glu Asn Glu Ile Arg Val Lys Val Arg Ala Leu Thr Glu Lys
                435                 440                 445

Ser Arg Met Ala Leu Met Glu Gly Gly Ser Ser Tyr Asn Tyr Leu Lys
        450                 455                 460

Arg Phe Val Glu Asn Val Val Asn Asn Ile Ser
465                 470                 475

<210> SEQ ID NO 83
<211> LENGTH: 25
<212> TYPE: DNA
<213> ORGANISM: Sesamun indicum

<400> SEQUENCE: 83
acgaagttat gcggccaatt aaccc                                         25

<210> SEQ ID NO 84
<211> LENGTH: 25
<212> TYPE: DNA
<213> ORGANISM: Sesamun indicum

<400> SEQUENCE: 84
ccacctgacg tcgcggccta atacg                                         25

<210> SEQ ID NO 85
<211> LENGTH: 20
<212> TYPE: DNA
<213> ORGANISM: Sesamun indicum

<400> SEQUENCE: 85
taatacgact cactataggg                                               20

<210> SEQ ID NO 86
<211> LENGTH: 893
<212> TYPE: DNA
<213> ORGANISM: Sesamun indicum

<400> SEQUENCE: 86
actagtaacg gccgccagtg tgctggaatt cgcccttgta atacgactca ctagggcg     60
accgcggatc ttcactatca ctacttcaaa ggacgggcaa ccgtccgcat ccgctactta  120
tcgtcctgat cgattatacc aattcttatt gaggatcggg ttccacaaat actatccaat  180
ttaattttt atctgctttt cactttttt ataaatatta tttatttta attttctac     240
aactttgaac tttctctgtt aaaatgattt acctaaaatt aaaattttcc caaacactcc  300
tagtatgtca gaatcttttg atatctacaa tagattgaat tacaattttc actctattat  360
tataaggcgt cgacgtttat tgttctagga aaataaaatc tggtacctaa aaagacacta  420
gttaaagaaa aataaaaatt ggtagattga agtgaatttc tgtgaagatt ctacaatttg  480
ctggaaattg attttgatt tgggatttta tatgttggtt atttaaactg aaaagtggag  540
catttcatca ttcatgtttt gcttaattgg attgcatata ggtctgatca acatgttttg  600
tcggaaaatt taagttttcc caatcaaaga ttgattggcc cagctttcgg tgaaatttgt  660
cgtcagctcg cagttgaatt gtttttaatt actgttttta atattatcca ttcattttt   720
acaagataag aaatgtcatt tccttatttg taaaggatca aattgcaatt aaaccatctc  780
aaatgcatag cattacacgc ctgcgtatgt gtatgtctga tctcaagaat cagtgagact  840
cttgtgtcat atcgtctttc ccttccaatt tcctgaattc agcaccagaa aac          893
```

<210> SEQ ID NO 87
<211> LENGTH: 1457
<212> TYPE: DNA
<213> ORGANISM: Sesamun indicum

<400> SEQUENCE: 87

| | | | | | |
|---|---|---|---|---|---|
| aatttatgta | atagacagtg | tcaatttgga | ttgtttgtta | taaatttgaa | aacatgatta | 60 |
| attcaaatta | tgttctatca | aattaaaatt | atttatttga | cagacatgat | acaaatttat | 120 |
| ctataggtat | aggattgtta | tatattattc | ataatgatat | ttgtcatgta | atcaattaat | 180 |
| taatttcaac | ataaaacttg | tgtaattgga | tcttgttttt | aattttttct | taaattaaaa | 240 |
| tatataaatt | gcgtgtatat | agtatttatt | tttattattt | atactattac | aaaagaaaat | 300 |
| ttattgatcc | catttacttt | tttcgttcat | tttattttgt | ttttttaatta | ttttataatt | 360 |
| acatttttt | cctctcaccc | aatactccat | ttctctttct | catgttcttt | atattttttc | 420 |
| ctctcacaaa | tatgaaatag | atagtttaga | ggtagtttaa | agcagcataa | agtagaaagc | 480 |
| cgtcctattt | aggttgttgg | aattgaagga | ggaaggaagg | gcaaatccat | tacgtcagtc | 540 |
| aaaaaaagaa | gcttttatga | ctgatgaaca | ccaaccggtc | taccaggagc | aaagagctca | 600 |
| cctaacctag | agaattcact | ccctggatgt | aagtccaatc | aatcagtagc | ggtagaatag | 660 |
| tccgatttcc | tagcttcgga | agccctctcg | aaaagccccc | ttccaatgac | cctaagcgct | 720 |
| aaaatcaacc | cttgtaatgt | cactgaacga | aagtcttaga | gcagtaataa | ggaacacaac | 780 |
| aaacccaaca | acaaaatcgg | ctaggctgag | tttgaaagtt | gcgattttcg | atacgttttt | 840 |
| ccttttttgt | aaaaaagaga | aaaatccctg | tagatagaga | tccgcttctc | tagatggccc | 900 |
| ggcgtacagc | cctacatttc | tcaattcaca | acaagacctc | tgagaaaaag | aatttagatc | 960 |
| gaggcgtcga | agcgagctta | gcaaccctaa | gcgaagtctt | cccctatcca | taattttaat | 1020 |
| aaatcctatt | acagttattt | ttttctctca | catttatcat | attttatttt | tcgtacaaat | 1080 |
| tttcatattt | ttaatgaact | ctaaattgta | attctttcgt | cttttttact | ttatcccata | 1140 |
| tttttttttt | atcacctcac | aacattatgt | gtttttctat | aatattttt | ttcttcattt | 1200 |
| cacagtataa | ttttcatat | ataaattgc | ataaacaaca | tatatttttt | ctcttcattt | 1260 |
| catagtataa | tttttcatat | gatcgcagaa | acaacatgca | acgaccacta | ataaaaataa | 1320 |
| tgaatcaata | ttaaagtgct | aaaacatgaa | aattgtagtg | gagttgttga | agtggaaaaa | 1380 |
| gccacacaca | ctgaagtagg | tgaagaccaa | actgtataaa | taaaggttac | gtgttgctac | 1440 |
| gtgtcttcac | tcttcac | | | | | 1457 |

<210> SEQ ID NO 88
<211> LENGTH: 24
<212> TYPE: DNA
<213> ORGANISM: Sesamun indicum

<400> SEQUENCE: 88
gaagacttcg cttagggttg ctaa        24

<210> SEQ ID NO 89
<211> LENGTH: 2407
<212> TYPE: DNA
<213> ORGANISM: Sesamun indicum

<400> SEQUENCE: 89

| | | | | | |
|---|---|---|---|---|---|
| gtaatacgac | tcactatagg | gggaccgcgg | atcatatttt | tttcaataaa | atgtgaaaaa | 60 |
| tataaaaaat | tattgatagg | ggcaatttta | tctatacaaa | gaggataaat | attgaaaatg | 120 |

```
cataaaaaaa aaatcatttc attcgcatgt gcagtgcgtg tagatatatt ttttttttat    180
aaagagaatc ttttttacag acatttataa ttacataatg tctgtcttga ttatttaatt    240
aatacaagta agtatttaat aattttttgta caacacaaag gtaatatgta attttccata   300
aaaagaaata agacaaaatc ggagaaaggt taggtcatgg ctgacttcac atatacatat    360
gtcttaatcg gattagacgc tgccggctct tactttttcga attcctcaca tatacatata   420
tgtcttgaat ttggaccatc ttaccagaca taaatcggat ttgtcgccgg cggctcttac    480
ttttcgaatt ctgtgtaact cacattcaaa cttattaatt tgtacactaa tatatttatc    540
caggccaatt aaatcaatga cgtactataa aatgattaca taattatatt tcttaaaatt    600
tgtaaatata ttataattaa ttaaaatgaa attttgtgt ttgtccacca cctttgcaaa    660
tacaaagacg aacaatagcg ttccggtttt tgttcatgta aagtgtcaag tccccaccta    720
cctcatcact cattaatctt gtcatttctt ttgcccctac ttgctactat tgtgattata    780
tacaaaagac tatattttatg gataatttac atatactttt atggactatg ttctaactta   840
taataatgct ggaaatctaa acttttttatt ttattttctt ttcttttttgt atatgataaa   900
tatgctcttg cagtctttac ttcctcaatc acattattag ttcggtcaat aatttatgta    960
atagacagtg tcaatttgga ttgtttgtta taaatttgaa aacatgatta attcaaatta   1020
tgttctatca aattaaaatt atttatttga cagacatgat acaaatttat ctataggtat   1080
aggattgtta tatattattc ataatgatat ttgtcatgta atcaattaat taatttcaac   1140
ataaaacttg tgtaattgga tcttgttttt aattttttct taaattaaaa tatataaatt   1200
gcgtgtatat agtatttatt tttattattt atactattac aaaagaaaat ttattgatcc   1260
catttttactt tttcgttcat tttattttgt tttttaatta ttttataatt acattttttt   1320
cctctcaccc aatactccat ttctctttct catgttcttt atattttttc ctctcacaaa   1380
tatgaaatag atagtttaga ggtagtttaa agcagcataa agtagaaagc cgtcctattt   1440
aggttgttgg aattgaagga ggaaggaagg gcaaatccat tacgtcagtc aaaaaaagaa   1500
gcttttatga ctgatgaaca ccaaccggtc taccaggagc aaagagctca cctaacctag   1560
agaattcact ccctggatgt aagtccaatc aatcagtagc ggtagaatag tccgatttcc   1620
tagcttcgga agccctctcg aaaagccccc ttccaatgac cctaagcgct aaaatcaacc   1680
cttgtaatgt cactgaacga aagtcttaga gcagtaataa ggaacacaac aaacccaaca   1740
acaaaatcgg ctaggctgag tttgaaagtt gcgattttcg atacgttttt cctttttgt    1800
aaaaaagaga aaaatccctg tagatagaga tccgcttctc tagatggccc ggcgtacagc   1860
cctacatttc tcaattcaca acaagacctc tgagaaaaag aatttagatc gaggcgtcga   1920
agcgagctta gcaaccctaa gcgaagtctt cccctatcca taattttaat aaatcctatt   1980
acagttattt ttttctctca catttatcat atttatttttt tcgtacaaat tttcatattt   2040
ttaatgaact ctaaattgta attctttcgt cttttttact ttatcccata tttttttttt    2100
atcacctcac aacattatgt gtttttctat aatatttttt ttcttcattt cacagtataa   2160
tttttcatat atataattgc ataaacaaca tatattttt ctcttcattt catagtataa   2220
tttttcatat gatcgcagaa acaacatgca acgaccacta ataaaaataa tgaatcaata   2280
ttaaagtgct aaaacatgaa aattgtagtg gagttgttga agtggaaaaa gccacacaca   2340
ctgaagtagg tgaagaccaa actgtataaa taaaggttac gtgttgctac gtgtcttcac   2400
tcttcac                                                              2407
```

<210> SEQ ID NO 90

<211> LENGTH: 1431
<212> TYPE: DNA
<213> ORGANISM: Sesamun alatum

<400> SEQUENCE: 90

```
atgtcggcgg accaaaaatt aaccagccta gtcttcgttc ctttccctat aatgagtcac      60
ctggcaacag cagtgaagac ggcgaagctc ctggccgaca gagacgaacg cctctcgatc     120
acagtcctcg tgatgaagct accaattgat acgctgatca gttcttacac taagaactcg     180
cctgacgccc gagtaaaagt agtccaactg cccgaagacg agcccacctt tacaaagctg     240
atgaaatctt ccaagaactt cttctttcga tacatcgaga gccagaaagg cactgtcagg     300
gacgctgtgg ctgagattat gaagagttcg aggtcgtgta ggcttgcagg atttgtaatc     360
gacatgttct gcacaaccat gattgatgtc gccaacgagc ttggagtccc gacttacatg     420
ttcttcagtt cgggttcagc aacgctcggg ctcatgttcc atctccagag tctcagagat     480
gacaataatg tggacgtcat ggagtacaag aattcagatg ctgcgatatc aatacccaca     540
tacgttaacc ccgttcctgt tgcggtatgg ccttcccagg tgtttgagga ggacagtggt     600
ttccttgact tgccaaaaag gtttagagaa accaaaggga ttattgtgaa cacattcctc     660
gaattcgaaa cccaccagat taggtcattg tctgatgaca agaaaatccc accagtttat     720
cctgtgcggg caatacttca agctgatgag aacaaaattg agcaggaaaa ggaaaagcac     780
gcggaaatca tgaggtggct cgacaagcaa cctgattctt ctgtagtgtt tctttgcttt     840
ggtacgcatg gatgtttgga aggggatcag gtgaaggaga ttgctgtggc cctggaaaac     900
agtggacatc ggttttttgtg gtccctgagg aagccgcctc cgaaagaaaa ggttgagttt     960
ccaggagagt atgagaattc agaagaagtt ttaccagaag ggttcctggg acgaactact    1020
gacatgggta agttatcgg atgggcgcct caaatggcag tgttatctca ccctgcggtg    1080
ggaggatttg tgtcgcactg tgggtggaac tctgtgttgg aaagtgtgtg gtgtggggtg    1140
ccgatggccg tgtggccgtt gtctgcagag cagcaggcca atgcattctt gctagtaaag    1200
gagtttgaaa tggcagttga gattaagatg gattataaga aaaatgctaa cgtgattgtg    1260
ggcacagaga cgatagagga agcaatcaga cagctaatgg acccagagaa tgaaattcgg    1320
gttaaggtga gagcattgaa agaaaagagc agaatggccc taatggaagg agggtcttcg    1380
tacaattact tgaaacgttt cgtcgagaat gtcgtgaata acatttcttg a             1431
```

<210> SEQ ID NO 91
<211> LENGTH: 476
<212> TYPE: PRT
<213> ORGANISM: Sesamun alatum

<400> SEQUENCE: 91

```
Met Ser Ala Asp Gln Lys Leu Thr Ser Leu Val Phe Val Pro Phe Pro
  1               5                  10                  15

Ile Met Ser His Leu Ala Thr Ala Val Lys Thr Ala Lys Leu Leu Ala
                 20                  25                  30

Asp Arg Asp Glu Arg Leu Ser Ile Thr Val Leu Val Met Lys Leu Pro
             35                  40                  45

Ile Asp Thr Leu Ile Ser Ser Tyr Thr Lys Asn Ser Pro Asp Ala Arg
         50                  55                  60

Val Lys Val Val Gln Leu Pro Glu Asp Glu Pro Thr Phe Thr Lys Leu
 65                  70                  75                  80

Met Lys Ser Ser Lys Asn Phe Phe Phe Arg Tyr Ile Glu Ser Gln Lys
                 85                  90                  95
```

```
Gly Thr Val Arg Asp Ala Val Ala Glu Ile Met Lys Ser Ser Arg Ser
            100                 105                 110

Cys Arg Leu Ala Gly Phe Val Ile Asp Met Phe Cys Thr Thr Met Ile
        115                 120                 125

Asp Val Ala Asn Glu Leu Gly Val Pro Thr Tyr Met Phe Phe Ser Ser
    130                 135                 140

Gly Ser Ala Thr Leu Gly Leu Met Phe His Leu Gln Ser Leu Arg Asp
145                 150                 155                 160

Asp Asn Val Asp Val Met Glu Tyr Lys Asn Ser Asp Ala Ala Ile
                165                 170                 175

Ser Ile Pro Thr Tyr Val Asn Pro Val Ala Val Trp Pro Ser
            180                 185                 190

Gln Val Phe Glu Glu Asp Ser Gly Phe Leu Asp Phe Ala Lys Arg Phe
        195                 200                 205

Arg Glu Thr Lys Gly Ile Ile Val Asn Thr Phe Leu Glu Phe Glu Thr
        210                 215                 220

His Gln Ile Arg Ser Leu Ser Asp Asp Lys Lys Ile Pro Pro Val Tyr
225                 230                 235                 240

Pro Val Gly Pro Ile Leu Gln Ala Asp Glu Asn Lys Ile Glu Gln Glu
            245                 250                 255

Lys Glu Lys His Ala Glu Ile Met Arg Trp Leu Asp Lys Gln Pro Asp
            260                 265                 270

Ser Ser Val Val Phe Leu Cys Phe Gly Thr His Gly Cys Leu Glu Gly
        275                 280                 285

Asp Gln Val Lys Glu Ile Ala Val Ala Leu Glu Asn Ser Gly His Arg
        290                 295                 300

Phe Leu Trp Ser Leu Arg Lys Pro Pro Lys Glu Lys Val Glu Phe
305                 310                 315                 320

Pro Gly Glu Tyr Glu Asn Ser Glu Glu Val Leu Pro Glu Gly Phe Leu
            325                 330                 335

Gly Arg Thr Thr Asp Met Gly Lys Val Ile Gly Trp Ala Pro Gln Met
            340                 345                 350

Ala Val Leu Ser His Pro Ala Val Gly Gly Phe Val Ser His Cys Gly
        355                 360                 365

Trp Asn Ser Val Leu Glu Ser Val Trp Cys Gly Val Pro Met Ala Val
        370                 375                 380

Trp Pro Leu Ser Ala Glu Gln Gln Ala Asn Ala Phe Leu Leu Val Lys
385                 390                 395                 400

Glu Phe Glu Met Ala Val Glu Ile Lys Met Asp Tyr Lys Lys Asn Ala
            405                 410                 415

Asn Val Ile Val Gly Thr Glu Thr Ile Glu Glu Ala Ile Arg Gln Leu
            420                 425                 430

Met Asp Pro Glu Asn Glu Ile Arg Val Lys Val Arg Ala Leu Lys Glu
            435                 440                 445

Lys Ser Arg Met Ala Leu Met Glu Gly Gly Ser Ser Tyr Asn Tyr Leu
        450                 455                 460

Lys Arg Phe Val Glu Asn Val Val Asn Asn Ile Ser
465                 470                 475
```